United States Patent
Walsh et al.

(10) Patent No.: US 9,777,002 B2
(45) Date of Patent: Oct. 3, 2017

(54) INHIBITORS OF THE RENAL OUTER MEDULLARY POTASSIUM CHANNEL

(71) Applicant: Merck Sharp & Dohme Corp., Rahway, NJ (US)

(72) Inventors: Shawn P. Walsh, Bridgewater, NJ (US); Brian Cato, Secaucus, NJ (US); Jessica L. Frie, Harleysville, PA (US); Dooseop Kim, Seoul (KP); Alexander Pasternak, Princeton, NJ (US); Zhi-Cai Shi, Monmouth Junction, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/647,257

(22) PCT Filed: Nov. 22, 2013

(86) PCT No.: PCT/US2013/071369
§ 371 (c)(1),
(2) Date: May 26, 2015

(87) PCT Pub. No.: WO2014/085210
PCT Pub. Date: Jun. 5, 2014

(65) Prior Publication Data
US 2015/0299198 A1    Oct. 22, 2015

Related U.S. Application Data

(60) Provisional application No. 61/731,024, filed on Nov. 29, 2012.

(51) Int. Cl.
| | |
|---|---|
| C07D 471/10 | (2006.01) |
| C07D 405/14 | (2006.01) |
| A61K 45/06 | (2006.01) |
| A61K 31/401 | (2006.01) |
| A61K 31/404 | (2006.01) |
| A61K 31/41 | (2006.01) |
| A61K 31/4178 | (2006.01) |
| A61K 31/4184 | (2006.01) |
| A61K 31/4422 | (2006.01) |
| A61K 31/55 | (2006.01) |
| A61K 31/675 | (2006.01) |
| C07D 413/14 | (2006.01) |
| C07D 405/06 | (2006.01) |

(Continued)

(52) U.S. Cl.
CPC .......... *C07D 471/10* (2013.01); *A61K 31/401* (2013.01); *A61K 31/404* (2013.01); *A61K 31/41* (2013.01); *A61K 31/4178* (2013.01); *A61K 31/4184* (2013.01); *A61K 31/4353* (2013.01); *A61K 31/4422* (2013.01); *A61K 31/4439* (2013.01); *A61K 31/4468* (2013.01); *A61K 31/453* (2013.01); *A61K 31/454* (2013.01); *A61K 31/4525* (2013.01); *A61K 31/4535* (2013.01); *A61K 31/4545* (2013.01); *A61K 31/4725* (2013.01); *A61K 31/497* (2013.01); *A61K 31/501* (2013.01); *A61K 31/55* (2013.01); *A61K 31/675* (2013.01); *A61K 45/06* (2013.01); *C07D 211/58* (2013.01); *C07D 405/06* (2013.01); *C07D 405/12* (2013.01); *C07D 405/14* (2013.01); *C07D 409/14* (2013.01); *C07D 413/14* (2013.01); *C07D 417/14* (2013.01); *C07D 471/08* (2013.01)

(58) Field of Classification Search
CPC .. C07D 211/58; C07D 405/06; C07D 405/12; C07D 405/14; C07D 409/14; C07D 413/14; C07D 471/10; C07D 471/14; C07D 487/04
USPC .... 514/252.03, 255.05, 31 O, 315, 318, 320, 514/322, 339; 544/238, 405; 546/146, 546/194, 196, 199, 244, 276
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

Archibald et al. "antiinflammatory . . . " CA77:34355 (1972).*

(Continued)

*Primary Examiner* — Heidi Reese
(74) *Attorney, Agent, or Firm* — Baerbel R. Brown; Catherine D. Fitch

(57) ABSTRACT

The present invention provides compounds of Formula I

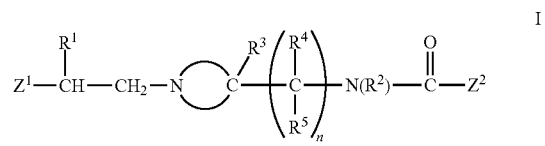

and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and conditions associated with excessive salt and water retention.

14 Claims, No Drawings

(51) Int. Cl.

| | |
|---|---|
| C07D 405/12 | (2006.01) |
| C07D 409/14 | (2006.01) |
| C07D 417/14 | (2006.01) |
| C07D 471/08 | (2006.01) |
| C07D 211/58 | (2006.01) |
| A61K 31/4353 | (2006.01) |
| A61K 31/4439 | (2006.01) |
| A61K 31/4468 | (2006.01) |
| A61K 31/4525 | (2006.01) |
| A61K 31/453 | (2006.01) |
| A61K 31/4535 | (2006.01) |
| A61K 31/454 | (2006.01) |
| A61K 31/4545 | (2006.01) |
| A61K 31/4725 | (2006.01) |
| A61K 31/497 | (2006.01) |
| A61K 31/501 | (2006.01) |

(56) References Cited

U.S. PATENT DOCUMENTS

| | | | |
|---|---|---|---|
| 3,632,608 A | | 1/1972 | Holub |
| 3,749,722 A | | 7/1973 | Holub |
| 4,046,767 A | * | 9/1977 | Cavalla ............... C07D 211/58 546/197 |
| 4,579,863 A | | 4/1986 | Horwell et al. |
| 4,806,536 A | | 2/1989 | Cross et al. |
| 4,992,547 A | | 2/1991 | Berner et al. |
| 5,070,094 A | * | 12/1991 | Fowler ............... C07D 451/04 514/304 |
| 5,145,885 A | | 9/1992 | Berner et al. |
| 5,215,989 A | | 6/1993 | Baldwin et al. |
| 5,614,526 A | | 3/1997 | Godel et al. |
| 5,736,546 A | | 4/1998 | Kawashima et al. |
| 6,258,813 B1 | | 7/2001 | Arlt et al. |
| 6,787,543 B2 | | 9/2004 | Take et al. |
| 8,673,920 B2 | * | 3/2014 | Pasternak ............ C07D 295/135 514/218 |
| 8,952,166 B2 | | 2/2015 | Ding et al. |
| 9,018,211 B2 | * | 4/2015 | Pasternak ............ C07D 295/135 514/249 |
| 2004/0110793 A1 | | 6/2004 | Lloyd et al. |
| 2004/0204404 A1 | | 10/2004 | Zelle et al. |
| 2005/0215526 A1 | | 9/2005 | Hulme et al. |
| 2005/0267121 A1 | | 12/2005 | Li et al. |
| 2006/0183739 A1 | | 8/2006 | Tsaklakidis et al. |
| 2006/0183742 A1 | | 8/2006 | Mederski et al. |
| 2006/0211692 A1 | | 9/2006 | Mederski et al. |
| 2007/0004750 A1 | | 1/2007 | Lorsbach et al. |
| 2007/0093472 A1 | | 4/2007 | Mederski et al. |
| 2008/0003214 A1 | | 1/2008 | Cezanne et al. |
| 2010/0286123 A1 | | 11/2010 | Pasternak et al. |

FOREIGN PATENT DOCUMENTS

| | | |
|---|---|---|
| EP | 1094063 A1 | 4/2001 |
| EP | 1939175 A1 | 7/2009 |
| FR | 2673182 | 8/1992 |
| FR | 2673182 A1 | 8/1992 |
| GB | 949088 A | 2/1964 |
| GB | 1575310 A | 9/1980 |
| GB | 2116967 | 7/1986 |
| JP | 10203986 | 8/1998 |
| WO | 9744329 | 11/1997 |
| WO | 0051611 A1 | 9/2000 |
| WO | 0204314 A1 | 6/2002 |
| WO | 0250061 A1 | 6/2002 |
| WO | 0232874 | 11/2003 |
| WO | 2004020422 A1 | 3/2004 |
| WO | 2004037817 A1 | 5/2004 |
| WO | 2004046110 | 6/2004 |
| WO | 2005037843 | 4/2005 |
| WO | 2005044797 | 5/2005 |
| WO | 2006034341 A2 | 3/2006 |
| WO | 2006034769 A1 | 4/2006 |
| WO | 2006098342 A1 | 9/2006 |
| WO | 2006129199 A1 | 12/2006 |
| WO | 2007075629 A2 | 7/2007 |
| WO | WO2008040057 * | 4/2008 |
| WO | 2008147864 | 12/2008 |
| WO | 2008147864 A2 | 12/2008 |
| WO | 2009149508 | 11/2009 |
| WO | 2012058116 A1 | 5/2012 |
| WO | 2012058134 A1 | 5/2012 |
| WO | 2013028474 A1 | 2/2013 |
| WO | 2013039802 A1 | 3/2013 |
| WO | WO2013039802 * | 3/2013 |
| WO | 2013062892 A1 | 5/2013 |
| WO | 2013062900 A1 | 5/2013 |
| WO | 2013066714 A1 | 5/2013 |
| WO | 2013066717 A1 | 5/2013 |
| WO | 2013066718 A2 | 5/2013 |
| WO | 2013090271 A1 | 6/2013 |
| WO | 2014018764 A1 | 1/2014 |
| WO | WO2014099633 A2 | 6/2014 |
| WO | WO2014150132 A1 | 9/2014 |
| WO | WO2015017305 A1 | 2/2015 |

OTHER PUBLICATIONS

Bhave et al. "Development of a select . . . " Molecular Pharm. 79(1) 42-50 (2011).*
Chemcats , 1179403-13-4, (2009).*
Hanson et al. UK-78282 . . . Brit. J. Pharmcol. 126, 1707-1716 (1999).*
Harper et al. "The chemistry and . . . " 62:2980 (1965).*
Patani et al. "Bioisosterism . . . " Chem. Rev. 96 3147-76 (1996).*
Parkin et al. "Structure of piperazine . . . " Acta Cryst B60 219-227 (2004).*
Improper Markush, Fed Reg. 76(27) 7162-7175, slide 1, 64-67 (2011).*
ACCF/AHA Practice Guideline, 2009 Focused update incorporated into the ACC/AHA 2005 guidelines . . . , Circulation, 2009, e391-e436, 119.
Baltzly, R., The preparation of N-mono-substituted and unsymmetrically disubstituted piperazines, J. Am. Chemoc., 1944, 263-266, 66.
Bhave, G., Small-molecule modulators of inward rectifier K+ channels: recent advances and future possibilities, Future Med Chem, 2010, 757-774, 2(5).
Bhave,G., Development of a selective small-molecule inhibitor Kir1.1, the renal outer medullary potassium channel, Mol. Pharmacol., 2011, 42-50, 79.
Brater et al., Diuretic Therapy, Drug Therapy, 1998, 387-395, 339.
Brewster et al., Antihypertensive 1,4-bis (2-indol-3-ylethyl)piperazines, Chimie Ther., 1973, 169-172 (English trans.), 2.
Cerkvenik-Flajs V, Determination of residues of azaperone in the kidneys by liquid chromatography with fluorescence, Anal. Chim. Acta., 2007, 374-382, 586.
Chemical Abstracts (2004), Abstract No. 697771-49-6, "1,3-Isobenzofurandione 5-[[4-[(5-chloro-2-methoxyphenyl) sulfonyl]-1- . . . "
Cheymol et al., Increase in the effects of epinephrine and acetylcholine . . . , Comptes Rendus des seances de la Societe de Biologie, 1951, 496-499 (English trans.), 145.
Dorwald, Side reactions in Organic Synthesis: A Guide to Successful Synthesis Design, 2005, Chapter 1.
Fallen, K., The Kir channel immunoglobuling domain is essential for Kir1.1 (ROMK) thermodynamic stability, trafficking and gating, Channels, 2009, 57-66, 3.
Felker et al, Diuretic strategies in patients with acute decompensated heart failure, New Eng. J. Med., 2011, 797-805, 364.
Frank, Managing hypertension using combination therapy, Am. Fam. Physician, 2008, 1279-1286, 77.

(56) References Cited

OTHER PUBLICATIONS

International Search Report and Written Opinion of the ISR for PCT/US2013/71369 mailed Mar. 27, 2014, 8 pages.
Kulkarni, YD, Possible antifertility agents, part III. Synthesis of 4-(substituted aminomethyl)-5,6,7-trimethoxy phthalid . . . (abstract)), Biol. Mem., 1987, 141-144, 13.
Lanyi et al., Piperazine-Derivatives II, Res. Lab. of Chinoin-Fabrik Chemisch-Pharma. Prod., 1968, 1431-1435 (English trans.), 18.
Lewis, L. M., High-throughput screening reveals a small-molecule inhibitor of the Renal Outer Medullary Potassium Channel and Kir7.1, Mol. Pharncol., 2009, 1094-1103, 76.
Lutz, R. E., Antimalarials. Some Piperazine Derivatives, J. Org. Chem., 1947, 771-775, 12, BO.
Miyake et al., Synthesis of 1-substituted isochroman . . . , Takeda Res. Lab., 1982, 24-40 (English trans.), 41.
Sica, D. A., Diuretic use in renal disease, Nature, 2012, 100-109, 8.
Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US13/071369 filed Nov. 22, 2013, which claims priority from U.S. Provisional Application Ser. No. 61/731,024, filed Nov. 29, 2012.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

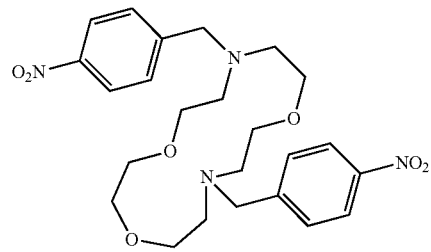

VU590

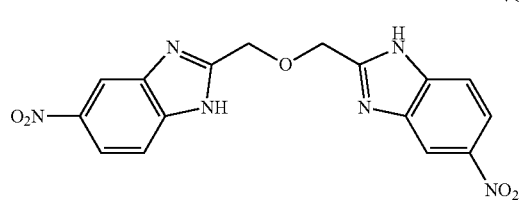

VU591

Patent application publication number WO2010/129379, published Nov. 11, 2010 having common representative Merck Sharp & Dohme Corp., (also published as US2010/0286123 on same date), describes ROMK inhibitors having the generic formula:

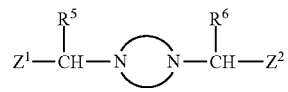

and, e.g., an embodiment

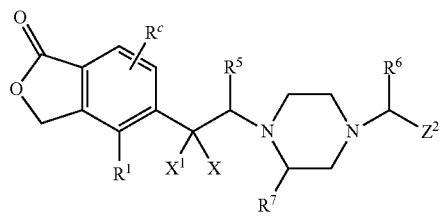

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$ alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

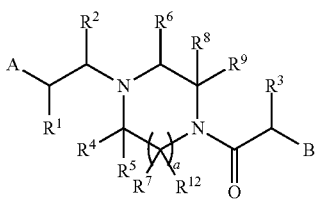

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to $R^{10b}$ to form a ring.

Patent application publication number WO2012/058116, published May 3, 2012, having common representative Merck Sharp & Dohme Corp., describes ROMK inhibitors having the generic formula:

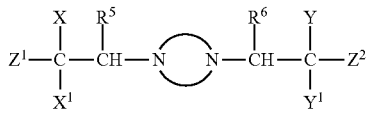

and, e.g., an embodiment

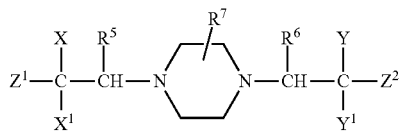

wherein $R^5$ and $R^6$ are independently —H, —$C_{1-6}$ alkyl or —$C(O)OC_{1-3}$alkyl; and X, $X^1$, Y and $Y^1$ are independently —H or —$C_{1-6}$alkyl; or $Y^1$ can be joined together with $Z^2$ to form a fused ring system.

However, continuing discovery of selective small molecule inhibitors of ROMK is still needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of structural Formula I

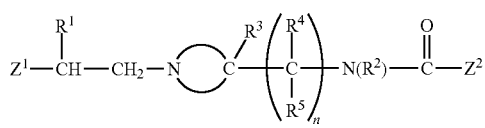

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

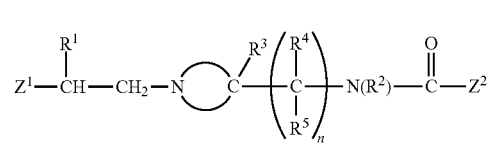

or a pharmaceutically acceptable salt thereof wherein:

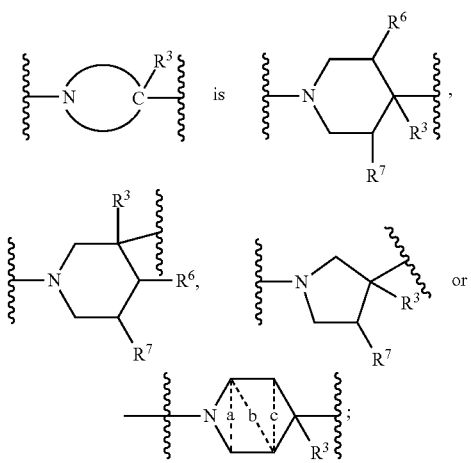

m is the integer zero or 1;
n is the integer zero or 1;
one of the dashed lines a, b or c represents a —$CH_2$— or —$CH_2$—$CH_2$— bridge, and the other dashed lines are absent;
$R^1$ is —H, —$OC_{1-3}$alkyl or —OH;
$R^2$ is —H or —$C_{1-3}$alkyl;
$R^3$ is —H, —F, —$C_{1-3}$alkyl or phenyl;

or, when n is zero, R² and R³ are joined together to represent —(CH₂)$_{(q)}$— and form a 4-6 member ring with the nitrogen and carbon to which each is attached;

q is the integer 2, 3 or 4;

R⁴ and R⁵ are each independently —H or —C$_{1-3}$alkyl, or R⁴ and R⁵ are joined together with the carbon to which they are attached to form C$_{3-6}$ cycloalkyl;

R⁶ is —H, —C$_{1-3}$alkyl, —OH, —OC$_{1-3}$alkyl or —F, or is di-fluoro that replaces two hydrogens on the carbon to which it is attached;

R⁷ is —H, —C$_{1-3}$alkyl, —OH, —OC$_{1-3}$alkyl or F, or is di-fluoro that replaces two hydrogens on the carbon to which it is attached;

Z¹ is

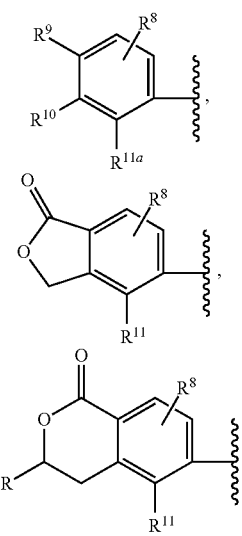

R is —H or —C$_{1-4}$alkyl;

R⁸ is —H, —F, —Cl, —C$_{1-6}$alkyl, —C$_{3-6}$cycloalkyl or —OC$_{1-6}$alkyl;

R⁹ is —H, —F, —Cl, —CN, —C$_{1-6}$alkyl, —C$_{3-6}$cycloalkyl or —OC$_{1-6}$alkyl; or when R¹⁰ is —H, then R⁹ can be 1H-tetrazol-1-yl;

R¹⁰ is —H, —Cl, —F, —CN, —C$_{1-6}$alkyl, —C$_{3-6}$cycloalkyl or —OC$_{1-4}$alkyl;

R¹¹ is —H, —Cl, —F, —CN, —C$_{1-4}$alkyl, —C$_{3-6}$cycloalkyl or —OC$_{1-4}$alkyl;

R¹¹ᵃ is —H, —Cl, —F, —CN, —C$_{1-4}$alkyl, —C$_{3-6}$cycloalkyl or —OC$_{1-4}$alkyl;

provided that R⁹ and R¹⁰ are not both H; and provided that one and only one of R⁹, R¹⁰ or R¹¹ᵃ is —CN;

Z² is

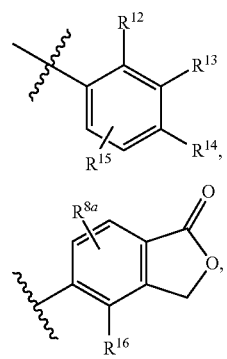

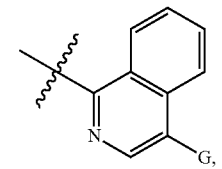

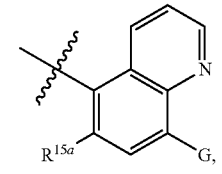

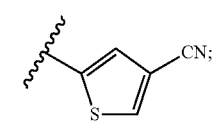

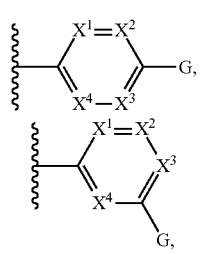

X¹, X², X³ and X⁴ are each independently C(Rᵃ) or N, provided that one or two of X¹, X², X³ and X⁴ must be N and the others are C(Rᵃ);

each Rᵃ is independently —H or —C$_{1-3}$alkyl;

G is —OC$_{1-3}$alkyl, —CN or a 5-membered heteroaryl;

R⁸ᵃ is —H, —F, —Cl, —C$_{1-6}$alkyl, —C$_{3-6}$cycloalkyl or —OC$_{1-6}$alkyl;

R¹² is —H, —C$_{1-3}$alkyl, —OC$_{1-3}$alkyl, —SO₂C$_{1-3}$alkyl or halo;

R¹³ is —H, —C$_{1-3}$alkyl, —OC$_{1-3}$alkyl, halo, —NO₂, —CN or a 5-membered heteroaryl;

R¹⁴ is —H, —C$_{1-3}$alkyl, —OC$_{1-3}$alkyl, halo, —NO₂, —CN or a 5-membered heteroaryl;

provided that only one of R¹³ and R¹⁴ is —CN, —NO₂ or the 5-membered heteroaryl and the other is —H, —C$_{1-3}$alkyl, —OC$_{1-3}$alkyl or halo;

R¹⁵ is —H, —C$_{1-3}$alkyl, —OC$_{1-3}$alkyl, —SO₂C$_{1-3}$alkyl or halo;

R¹⁵ᵃ is —H, —C$_{1-3}$alkyl, —OC$_{1-3}$alkyl, —SO₂C$_{1-3}$alkyl or halo;

or R² and R¹⁵ are joined together and represent —CH₂— to form the bicyclic fused ring system

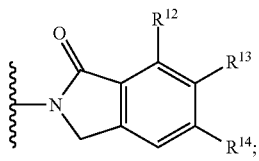

and $R^{16}$ is —H, —Cl, —F, —CN, —$C_{1-4}$alkyl, —$C_{3-6}$cycloalkyl or —$OC_{1-4}$alkyl.

In an embodiment of this invention are compounds of Formula I having structural Formula II and the pharmaceutically acceptable salts thereof:

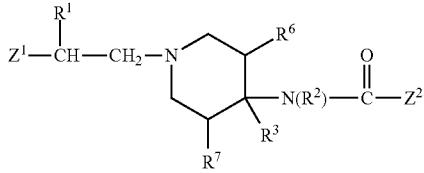

II wherein all variables therein are as defined in Formula I.

In a further embodiment are compounds of Formula II having structural Formula IIa,

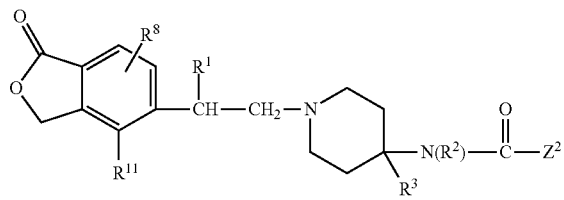

IIa and the pharmaceutically acceptable salts thereof, wherein: $R^1$ is —H or —OH, and particularly it is —OH; $R^2$ is —H or —$CH_3$, or $R^2$ and $R^{15}$ are joined together and represent —$CH_2$— to form the bicyclic fused ring system

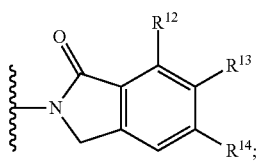

and $R^3$ is —H or —$C_{1-3}$alkyl. In a class of this embodiment are compounds wherein
$Z^2$ is

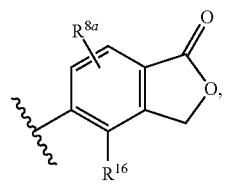

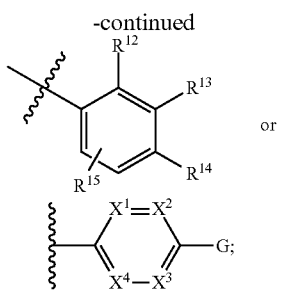

or

G is —CN or 1H-tetrazol-1-yl; when $R^2$ and $R^{15}$ are joined together and represent —$CH_2$— then $R^{14}$ is —NO2; and when $R^2$ and $R^{15}$ are not joined together, then one of $R^{13}$ and $R^{14}$ is —CN or the 5-membered heteroaryl and the other is —H, —$C_{1-3}$alkyl, —$OC_{1-3}$alkyl or halo; and all other variables therein are as defined in Formula I.

In another embodiment of this invention are compounds of Formula I having structural Formula III and the pharmaceutically acceptable salts thereof:

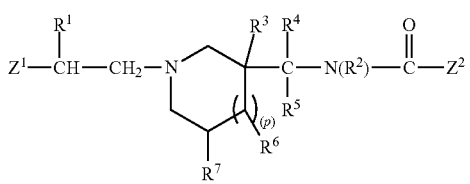

III wherein p is an integer selected from 0 (zero) or 1 (one); and all other variables therein are as defined in Formula I.

In a further embodiment are compounds of Formula III having structural Formula IIIa,

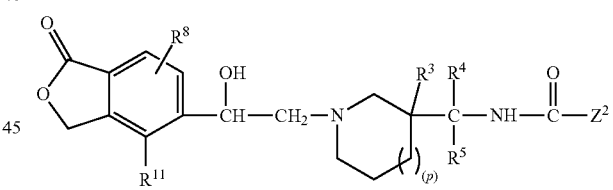

IIIa and the pharmaceutically acceptable salts thereof, wherein:
p is an integer selected from 0 (zero) or 1 (one);
$R^3$ is —H, —$C_{1-3}$alkyl or phenyl; and
$R^4$ and $R^5$ are each independently —H or —$C_{1-3}$alkyl, or $R^4$ and $R^5$ are joined together with the carbon to which they are attached to form $C_{3-6}$ cycloalkyl, or particularly $C_{3-4}$ cycloalkyl. In a class of this embodiment are compounds wherein
$Z^2$ is

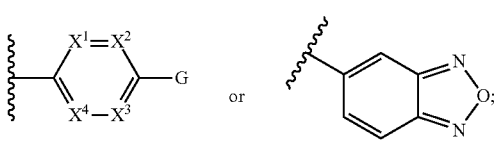

and G is 1H-tetrazol-1-yl;

and all other variables therein are as defined in Formula I.

In another embodiment of this invention are compounds of Formula I, II or III wherein $R^1$ is —H or —OH.

In another embodiment of this invention are compounds of Formula I, II, IIa or III wherein $R^2$ is —H or —CH$_3$, and more particularly it is —H.

In another embodiment of this invention are compounds of Formula I, II, or III wherein $R^3$ is —H, —C$_{1-3}$alkyl (particularly —CH$_3$) or phenyl.

In another embodiment of this invention are compounds of Formula I, III or IIIa wherein $R^4$ and $R^5$ are independently —H or —CH$_3$, or are joined together with the carbon to which they are attached to form C$_{3-6}$cycloalkyl, and particularly a C$_{3-4}$cycloalkyl.

In another embodiment of this invention are compounds of Formula I, II, or III wherein $R^6$ is —H, —F or —OCH$_3$.

In another embodiment of this invention are compounds of Formula I, II, or III wherein $R^7$ is —H, —F or —OCH$_3$.

In another embodiment of this invention are compounds of Formula I, II, IIa, III or IIIa wherein $R^8$ is —H, —F, —Cl, —CH$_3$ or —OCH$_3$.

In another embodiment of this invention are compounds of Formula I, II, IIa or III wherein $R^{8a}$ is —H, —F, —Cl, —CH$_3$ or —OCH$_3$.

In another embodiment of this invention are compounds of Formula I or II wherein one and only one of $R^9$ or $R^{10}$ is —CN and $R^{11a}$ is not —CN, and more particularly, $R^{10}$ is —CN, $R^9$ is —F and $R^{11a}$ is —C$_{1-4}$alkyl.

In another embodiment of this invention are compounds of Formula I, II, IIa or III wherein $R^{11}$ is —H or —CH$_3$.

In another embodiment of this invention are compounds of Formula I, II, IIa or III wherein $R^2$ and $R^{15}$ are not joined together; and one of $R^{13}$ and $R^{14}$ is —CN or the 5-membered heteroaryl and the other is —H, —C$_{1-3}$alkyl, —OC$_{1-3}$alkyl or halo.

In another embodiment of this invention are compounds of Formula I, II, IIa, III or IIIa wherein G is —CN or a 5-membered heteroaryl.

In another embodiment of this invention are compounds of Formula I, II, or III wherein $Z^1$ is

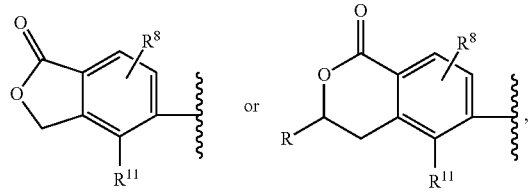

and more particularly wherein $R^8$ is —H and $R^{11}$ is —CH$_3$.

In another embodiment of this invention are compounds of Formula I, II, IIa or III wherein $Z^1$ is

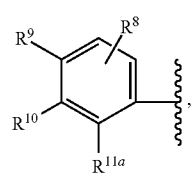

and more particularly wherein it is

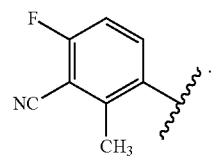

In another embodiment of this invention are compounds of Formula I, II, IIa, III or IIIa wherein $Z^2$ is

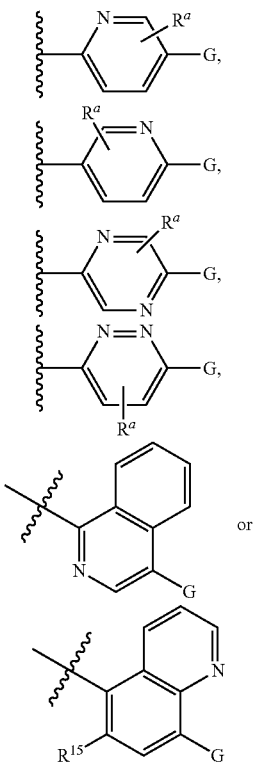

wherein $R^a$ is —H or —C$_{1-3}$alkyl, or particularly it is —H or —CH$_3$.

In another embodiment of this invention are compounds of Formula I, II, IIa, III or IIIa, or the above embodiment for $Z^2$ where G is present, wherein G is —OC$_{1-3}$alkyl, —CN or a 5-membered heteroaryl which is 1H-tetrazol-1-yl, 1H-pyrazol-1-yl, 1H-pyrazol-3-yl, isoxazol-3-yl, 1H-1,2,4-triazol-1-yl, 4-cyano-thiophene-2-yl or thiazol-2-yl; and particularly wherein the heteroaryl is 1H-tetrazol-1-yl, 1H-pyrazol-1-yl, or 1H-pyrazol-3-yl, and more particularly wherein G is 1H-tetrazol-1-yl.

In another embodiment of this invention are compounds of Formula I, II, IIa, III or IIIa wherein $Z^2$ is

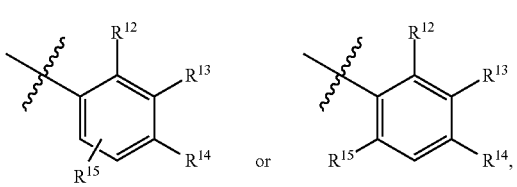

and particularly wherein one of $R^{13}$ and $R^{14}$ is —CN or a 5-membered heteroaryl and the other is —H, —CH$_3$, —OCH₃ or halo. In a class of this embodiment are compounds wherein the 5-membered heteroaryl is 1H-tetrazol-1-yl, 1H-pyrazol-1-yl, 1H-pyrazol-3-yl, isoxazol-3-yl, 1H-1,2,4-triazol-1-yl, 4-cyano-thiophene-2-yl or thiazol-2-yl; and particularly wherein it is 1H-tetrazol-1-yl, 1H-pyrazol-1-yl, or 1H-pyrazol-3-yl; and more particularly wherein it is 1H-tetrazol-1-yl.

In another embodiment of this invention are compounds of Formula I, II, IIa or III wherein $R^{16}$ is —H or —CH₃.

All structural Formulas and embodiments thereof described above include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). "Cycloalkyl" is a cyclized alkyl ring having the indicated number of carbon atoms. Examples of cycloalkyl include cyclopropyl, cyclobutyl, cyclopentyl and cyclohexyl.

"Halo" means —F, —Cl, —Br, or —I. Preferred halo groups are —F and —Cl, and particularly —F.

"Heteroaryl" unless otherwise indicated, means a mono- or bicyclic unsaturated or aromatic ring system comprised of one or more carbon atoms and at least one heteroatom selected from O, S and N. Each ring contains 5 to 10 atoms, unless the total number of atoms in a particular ring is specified. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, and the like. Heteroaryl includes bicyclic ring systems wherein a heteroaryl ring is fused to another ring which is non-aromatic, unsaturated or saturated comprised of carbon atoms and optionally one or more heteroatoms. Heteroaryl also includes such groups in charged form, e.g., pyridinium.

The 5-membered heteroaryl in the defintions of G, $R^{13}$ and $R^{14}$ herein means a mono-ring heteroaryl having five atoms in the ring comprised of one to four carbon atoms and at least one heteroatom selected from zero to four of N, zero to one of O and zero to one of S, wherein the heteroaryl is optionally substituted with —CN. The 5-membered heteroaryl is intended to include tetrazolyl, pyrazolyl, isoxazolyl, triazolyl, thienyl and thiazolyl, each one optionally substituted with —CN; and particularly 1H-tetrazol-1-yl, 1H-pyrazol-1-yl, 1H-pyrazol-3-yl, isoxazol-3-yl, 1H-1,2,4-triazol-1-yl, thiophene-2-yl (particularly 4-cyano-thiophene-2-yl) and thiazol-2-yl, as depicted below, respectively:

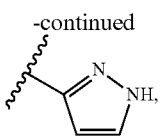

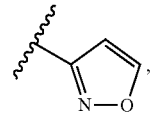

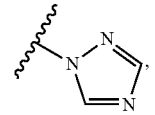

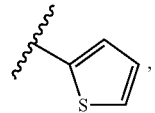

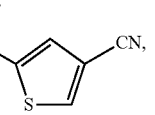

-continued

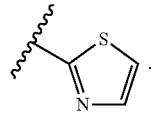

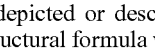

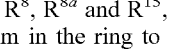

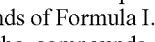

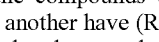

Unless expressly depicted or described otherwise, variables depicted in a structural formula with a "floating" bond, such as for example $R^8$, $R^{8a}$ and $R^{15}$, are permitted on any available carbon atom in the ring to which the variable is attached.

The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without a chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

Reference to the compounds of Formula I herein encompasses the compounds of Formulas I, II, IIa, III and IIIa and all embodiments and classes thereof. Reference to the compounds of this invention as those of a specific formula or embodiment, e.g., Formula I, II or III or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. The inhibition of ROMK by the compounds of Formula I can be examined, for example, in the Thallium Flux Assay and/or Electrophysiology Assay described below. Moreover, this invention also relates to the use of the compounds of Formula I or salts thereof to validate in vitro assays, for example but not limited to the Thallium Flux and Electrophysiology Assays described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, heart failure (both acute and chronic, the latter also known as congestive heart failure) and/or other conditions associated with excessive salt and water retention. Furthermore, the compounds of Formula I could be used in methods for treatment of, prevention of or reduction of risk for developing one or more disorders such as pulmonary arterial hypertension (PAH), cardiovascular disease, diabetes mellitus, diabetes insipidus, post-operative volume overload endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, glomerulonephritis, nephrotic syndrome, acute and chronic kidney insufficiency (also referred to as chronic kidney disease, or more generally as renal impairment), acute tubular necrosis, hypercalcemia, idiopathic edema, Dent's disease, Meniere's disease, edematous states, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) Thallium Flux Assay, 2) Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prohylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or *acacia*, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)-N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone prodrug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" susbtiuents in the Schemes correspond to the susbtituents defined in Formula I at the same positions on the structures.

Several methods for preparing the compounds of this invention are described in the following Schemes and Examples. Starting materials and intermediates are purchased, made from known procedures, or as otherwise illustrated. $Z^1$ and $Z^2$ groups and $R^1$, $R^2$ and $R^3$, $R^4$, $R^5$ and "n" shown in the schemes below are as previously defined in the text.

The preparation of the compounds I-1 is detailed in Scheme 1. Treatment of the aldehyde 1-1 with an appropriate mono-protected diamine 1-2 under standard reductive amination conditions (such as sodium triacetoxyborohydride, sodium borohydride, or sodium cyanoborohydride in alcoholic or nonpolar solvent) affords the ethylamine products 1-3. The Boc protecting group (Greene, T.; Wuts, P. G. M. *protective Groups in Organic Synthesis*, John Wiley and Sons, Inc., New York, N.Y. 1991) of 1-3 can be removed under acidic conditions, such as with TFA or HCl to make 1-4. Treatment of amine acid salt 1-4 with the appropriate electrophile 1-5 (such as where X—C(O)—$Z^2$ is a carboxylic acid, ester, or acid chloride) under standard amide bond forming conditions (such as EDC, HOBt, triethylamine) produces I-1.

SCHEME 1

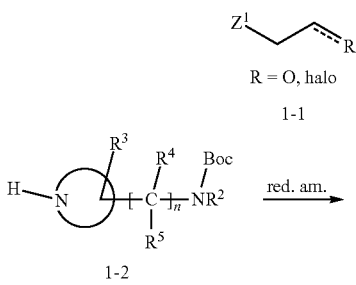

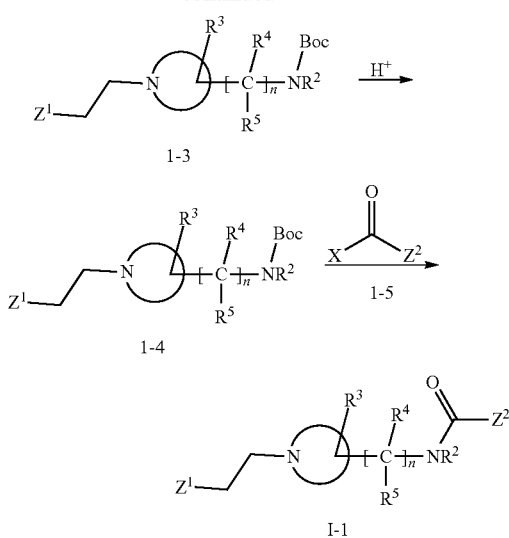

The preparation of the compounds I-2 is detailed in Scheme 2. Treatment of the epoxide 2-1 with an appropriate monoprotected diamine 1-2 under appropriate coupling conditions (such as heating in alcoholic solvent, or microwave heating) affords the amino alcohol 2-2. The Boc protecting group (Greene, T.; Wuts, P. G. M. *protective Groups in Organic Synthesis*, John Wiley and Sons, Inc., New York, N.Y. 1991) of 2-2 can be removed under acidic conditions, such as with TFA or HCl. The resulting amine may be coupled with the appropriate electrophile 2-4 (such as where X—C(O)—$Z^2$ is a carboxylic acid, ester, or acid chloride) under standard amide bond forming conditions (such as EDC, HOBt, triethylamine) to produce I-2.

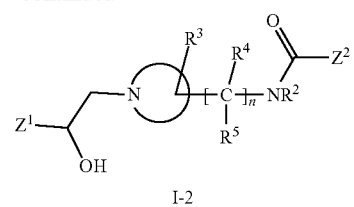

An alternate preparation of compounds of formula I-2 is shown in Scheme 3. Starting from appropriately monoprotected diamine 3-1, coupling with the desired electrophile 3-2 (such as where X—C(O)—$Z^2$ is a carboxylic acid, ester, or acid chloride) under standard amide bond forming conditions (such as EDC, HOBt, triethylamine) gives rise to 3-3. The Boc protecting group (Greene, T.; Wuts, P. G. M. *protective Groups in Organic Synthesis*, John Wiley and Sons, Inc., New York, N.Y. 1991) of 3-3 can be removed under acidic conditions, such as with TFA or HCl to obtain 3-4. Alternatively, the diamine may be protected with another protecting group such as Cbz, and subsequently removed by hydrogenolysis. For optimal regioselectivity in the epoxide opening, the free base of the resulting amine 3-4 should be generated in situ (as described in the preparation of EXAMPLEs below, for instance) or isolated previously through standard methods (for example sodium carbonate wash and extraction, ion exchange column chromatography, etc.). The resulting amine may be coupled to a second appropriate electrophile 3-5 (such as an aldehyde or epoxide) under the conditions described above to provide compounds I-2.

SCHEME 2

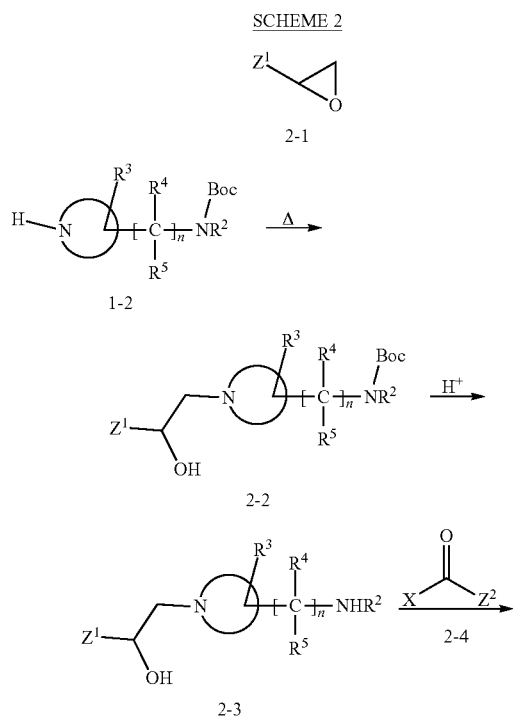

SCHEME 3

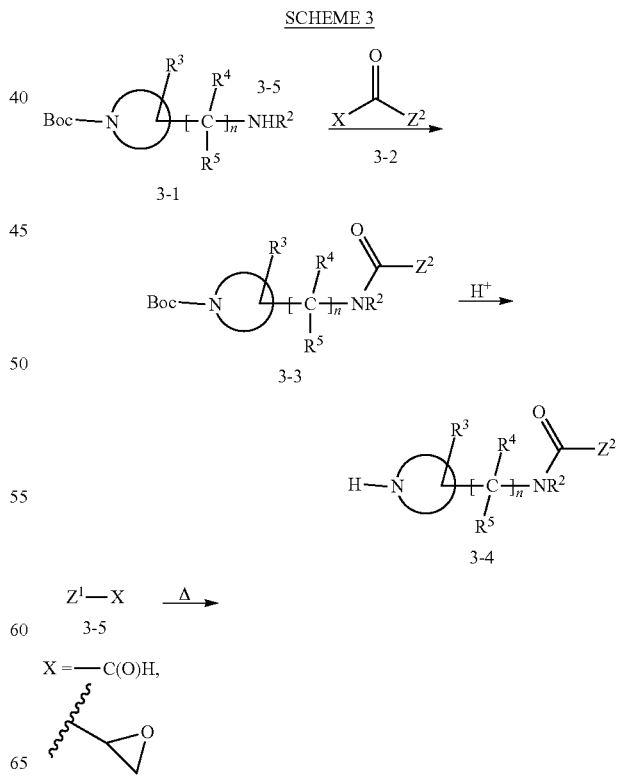

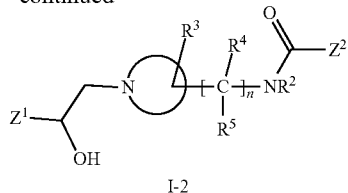

I-2

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions.

Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Abbreviations and acronyms used herein include: —C(O)CH$_3$ (Ac); acetic acid (AcOH); —OC(O)CH$_3$ (OAc); aqueous (aq); t-butyloxycarbonyl (Boc or BOC); n-butyl lithium (n-BuLi); carbodiimide (EDC, EDAC, or EDCI); benzyloxycarbonyl (Cbz); N;N-diisopropylethylamine (DIEA); N;N-dimethylformamide (DMF); dimethylsulfide (DMS); dimethylsulfoxide (DMSO); Diethylaminosulfur trifluoride (DAST); dichloromethane (DCM); dimethylacetamide (DMA; DMAC); 1,3-Bis(diphenylphosphino)propane (DPPP); ethylene glycol tetraacetic acid (EGTA); ethyl acetate (EtOAc); diethyl ether (ether or Et$_2$O); hexamethylphosphoramide (HMPA); 1-Hydroxybenzotriazole hydrate (HOBt); petroleum ether (PE); gram(s) (g); hour(s) (h or hr); 2-propanol (IPA); lithium diisopropylamide (LDA); mass spectrum (ms or MS); microliter(s) (μL); milligram(s) (mg); milliliter(s) (mL); millimole (mmol); minute(s) (min); methyl (Me); methanol (MeOH); methyl t-butylether (MTBE); nicotinamide adenine dinucleotide phosphate (NADP); N-bromosuccinamide (NBS); tris(dibenzylideneacetone)dipalladium(0) (Pd$_2$(dba)$_3$); (benzotriazol-1-yloxy)tripyrrolidino-phosphonium hexafluorophosphate (PyBOP); retention time (R$_t$); room temperature (rt, r. t. or RT); saturated aq sodium chloride solution (brine); triethylamine (TEA); trifluoroacetic acid (TFA); tetrahydrofuran (THF); acetic acid (HOAc); 3-chloroperoxybenzoic acid (m-CPBA); thin layer chromatography (TLC); flash chromatography (FC); liquid chromatography (LC); liquid chromatography-mass spectrometry (LCMS. LC/MS or LC-MS); mass spectrum (ms or MS); supercritical fluid chromatography (SFC); medium pressure liquid chromatography (MPLC); high pressure liquid chromatography (HPLC); Pd(dppf)Cl$_2$ or PdCl$_2$(dppf) is 1,1'-Bis(diphenylphosphino)ferrocene]dichloropalladium(II) which may be complexed with CH$_2$Cl$_2$; 1,1'-bis(diphenylphosphino)ferrocene (dppf, DPPF); O-(Benzotriazol-1-yl)-N,N,N',N'-tetramethyluronium tetrafluoroborate (TBTU). CELITE® is a trademark name for diatomaceous earth, The following are representative procedures for the preparation of intermediates used to prepare the final products described in the Examples that follow thereafter. These examples are provided for the purpose of further illustration only and are not intended to be limitations on the disclosed invention.

INTERMEDIATE 1

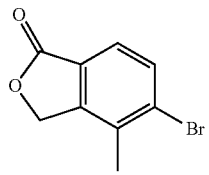

5-Bromo-4-methyl-2-benzofuran-1(3H)-one

Step A: (3-Bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol.

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a CELITE® pad, washed with EtOAc, adsorbed onto silica and purified by silica gel chromatography to afford 5-bromo-4-methyl-2-benzofuran-1(3H)-one. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

INTERMEDIATE 2

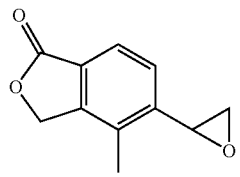

4-Methyl-5-oxiran-2-yl-2-benzofuran-1(3H)-one

Step A:
5-Ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmmol), PdCl$_2$(dppf)-CH$_2$Cl$_2$ Adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03(dd, J=11, 17 Hz, 1H), 5.84 (d, J=17 Hz, 1H), 5.55 (d, J=11 Hz, 1H), 5.29 (s, 2H), 2.34 (s, 3H). LC-MS: M+1=175.

Step B: 4-Methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then m-CPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2 H), 4.12 (s, 1 H), 3.27 (t, J=4 Hz, 1 H), 2.735 (dd, J=2.2, 5.5 Hz, 1H), 2.43 (s, 3H). LC-MS: M+1=191.

INTERMEDIATES 3A AND 3B

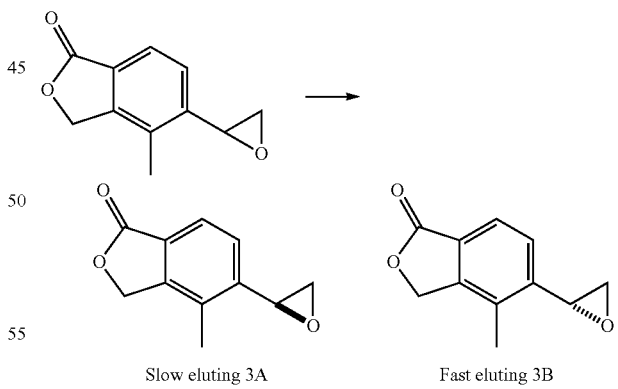

Slow eluting 3A    Fast eluting 3B

3A: 4-Methyl-5-[(2S)-oxiran-2-yl]-2-benzofuran-1(3H)-one and

3B: 4-Methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm)

under supercritical fluid chromatography (SFC) conditions on a Berger MGIII preparative SFC instrument. The racemate was diluted to 50 mg/ml in 1:1 DCM:MeOH. The separation was accomplished using 10% EtOH/CO$_2$, flow rate 200 ml/min, 100 bar, 25° C. 500 ul Injections were spaced every 2.12 mins. The fast epoxide (4-methyl-5-[(2R)-oxiran-2-yl]-2-benzofuran-1(3H)-one, 3B eluted at 5.2 min, and the slow epoxide (4-methyl-5-[(2S)-oxiran-2-yl]-2-benzofuran-1(3H)-one, 3A eluted at 5.6 min.

Alternatively, the resolution could also be achieved using a mobile phase of 8% MeOH/98% CO$_2$ with a flow rate of 100 ml/min. In that case the sample was prepared by dissolving in methanol, 20 mg/ml, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 3B, and by Mosher ester and Trost ester H-NMR analysis of an ester made starting from 3B.

INTERMEDIATE 4

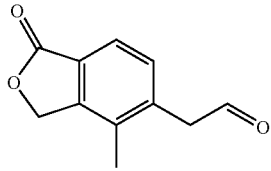

(4-Methyl-1-oxo-1,3-dihydro-2-benzofuran-5-yl)acetaldehyde

Step A: 4-Methyl-5-prop-2-en-1-yl-2-benzofuran-1(3H)-one

To a flask charged with 5-bromo-4-methyl-2-benzofuran-1(3H)-one (320 mg, 1.4 mmol) and a stir bar was added allyl tri-n-butyltin (0.66 mL, 2.1 mmol), Pd(PPh$_3$)$_4$ (240 mg, 0.21 mmol), lithium chloride (180 mg, 4.2 mmol), and toluene (15 mL). The reaction was purged with nitrogen 2 times then was heated at reflux for 4 hours. The reaction mixture was diluted with DCM, adsorbed onto silica gel, and purified by silica gel chromatography to provide 4-methyl-5-prop-2-en-1-yl-2-benzofuran-1(3H)-one.

Step B: (4-methyl-1-oxo-1,3-dihydro-2-benzofuran-5-yl)acetaldehyde

A solution of 4-methyl-5-prop-2-en-1-yl-2-benzofuran-1(3H)-one (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.87 mL, 12 mmol). The reaction was allowed to warm up to RT. The solvents were removed under reduced pressure. The resulting residue was purified by flash chromatography to afford (4-methyl-1-oxo-1,3-dihydro-2-benzofuran-5-yl)acetaldehyde.

$^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

INTERMEDIATE 5

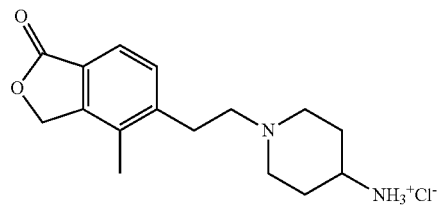

1-[2-(4-Methyl-1-oxo-1,3-dihydro-2-benzofuran-5-yl)ethyl]piperidin-4-aminium Chloride Step A: tert-Butyl {1-[2-(4-Methyl-1-oxo-1,3-dihydro-2-benzofuran-5-yl)ethyl]piperidin-4-yl}carbamate To a solution of tert-butyl piperidin-4-ylcarbamate (1.5 g, 7.5 mmol) in methanol (35 ml) was added (4-methyl-1-oxo-1,3-dihyro-2-benzofuran-5-yl)acetaldehyde (1.6 g, 8.2 mmol) at room temperature. The mixture was left to stir for 10 min, and then sodium cyanoborohydride (0.71 g, 11 mmol) was added to the mixture at room temperature. 10% Acetic acid (10 ml, 180 mmol) was then added dropwise to help with solubility. The reaction mixture was left to stir at rt for 2 h. The mixture was concentrated, and the residue was purified by MPLC (eluent: EtOAc/Hexanes 0% to 100%, then MeOH/DCM 0% to 10%) to provide tert-butyl {1-[2-(4-methyl-1-oxo-1,3-dihydro-2-benzofuran-5-yl)ethyl]piperidin-4-yl}carbamate. LC-MS (IE, m/z): 375 [M+1]$^+$.

Step B: 1-[2-(4-Methyl-1-oxo-1,3-dihydro-2-benzofuran-5-yl)ethyl]piperidin-4-aminium Chloride tert-butyl {1-[2-(4-methyl-1-oxo-1,3-dihydro-2-benzofuran-5-yl)ethyl]piperidin-4-yl}carbamate (2.0 g, 5.5 mmol) was dissolved in 40 ml of 4M HCl in 1,4-dioxane at rt. A few drops of methanol was added to help with solubility. The solution was stirred at rt for 3 h. The mixture was then concentrated to provide 1-[2-(4-methyl-1-oxo-1,3-dihydro-2-benzofuran-5-yl)ethyl]piperidin-4-aminium chloride, which was used directly in the next reaction without further purification. LC-MS (IE, m/z): 275 [M+1]$^+$.

INTERMEDIATE 6

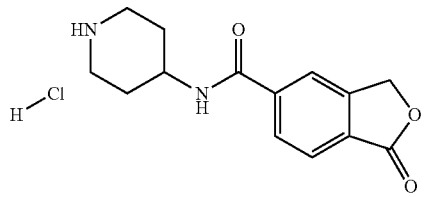

1-Oxo-N-(piperidin-4-yl)-1,3-dihydroisobenzofuran-5-carboxamide hydrochloride

Step A: tert-Butyl 4-(1-oxo-1,3-dihydroisobenzofuran-5-carboxamido)piperidine-1-carboxylate To a solution of 1-oxo-1,3-dihydroisobenzofuran-5-carboxylic acid (100 mg, 0.56 mmol), 4-amino-1-BOC-piperidine (110 mg, 0.56 mmol), HOBt (100 mg, 0.67 mmol), and EDC (160 mg, 0.84 mmol) in dichloromethane (2.8 mL) was added N-methylmorpholine (120 µl, 1.1 mmol) at room temperature. The reaction mixture was stirred at rt overnight. The mixture was concentrated and purified by prep TLC (silica gel, 10% methanol/dichloromethane) to provide tert-butyl 4-(1-oxo-1,3-dihydroisobenzofuran-5-carboxamido)piperidine-1-carboxylate. $^1$H-NMR (CDCl$_3$, 500 MHz), δ 8.02 (m, 2H), 7.88 (d, J=7.5 Hz, 1H), 6.18 (m, 1H), 5.39 (s, 2H), 4.20 (m, 4H), 2.95 (m, 2H), 2.09 (m, 2H), 1.43 (s, 9H); LC/MS: [(M+1)]$^+$=361.

Step B: 5-(1-fluoro-2-piperazin-1-ylethyl)-4-methyl-2-benzofuran-1(3H)-one hydrochloride A mixture of tert-butyl 4-(1-oxo-1,3-dihydroisobenzofuran-5-carboxamido)piperidine-1-carboxylate (140 mg, 0.39 mmol) and 4 M hydrogen chloride in 1,4-dioxane (14 mL) was stirred at room temperature for 1.5 h. The mixture was concentrated in vacuo and dried under high vacuum to provide 1-oxo-N-(piperidin-4-yl)-1,3-dihydroisobenzofuran-5-carboxamide hydrochloride. LC/MS: [(M+1)]$^+$=261.

INTERMEDIATE 7

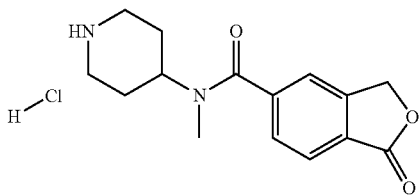

N-Methyl-1-oxo-N-(piperidin-4-yl)-1,3-dihydroisobenzofuran-5-carboxamide hydrochloride Step A: tert-Butyl 4-(N-methyl-1-oxo-1,3-dihydroisobenzofuran-5-carboxamido)piperidine-1-carboxylate To a solution of 1-oxo-1,3-dihydroisobenzofuran-5-carboxylic acid (100 mg, 0.56 mmol), 1-BOC-4-methylaminopiperdine (120 mg, 0.56 mmol), HOBt (100 mg, 0.67 mmol), and EDC (160 mg, 0.84 mmol) in dichloromethane (2.8 mL) was added N-methylmorpholine (120 µl, 1.1 mmol) at room temperature. The reaction mixture was stirred at rt overnight. The mixture was concentrated and purified by prep TLC (silica gel, 10% methanol/dichloromethane) to provide tert-butyl 4-(N-methyl-1-oxo-1,3-dihydroisobenzofuran-5-carboxamido)piperidine-1-carboxylate. $^1$H-NMR (CDCl$_3$, 500 MHz), δ 8.01 (d, J=7.5 Hz, 1H), 7.56 (m, 2H), 5.39 (s, 2H), 4.72 (m, 1H), 4.30 (m, 4H), 2.95 (m, 2H), 2.82 (s, 3H), 2.09 (m, 2H), 1.43 (s, 9H); LC/MS: [(M+1)]$^+$=375.

Step B: N-Methyl-1-oxo-N-(piperidin-4-yl)-1,3-dihydroisobenzofuran-5-carboxamide hydrochloride A mixture of tert-butyl 4-(N-methyl-1-oxo-1,3-dihydroisobenzofuran-5-carboxamido)piperidine-1-carboxylate (160 mg, 0.42 mmol) and 4 M hydrogen chloride in 1,4-dioxane (16 mL) was stirred at room temperature for 1.5 h. The mixture was concentrated in vacuo and dried under high vacuum to provide N-methyl-1-oxo-N-(piperidin-4-yl)-1,3-dihydroisobenzofuran-5-carboxamidehydrochloride. LC/MS: [(M+1)]$^+$=275.

INTERMEDIATE 8

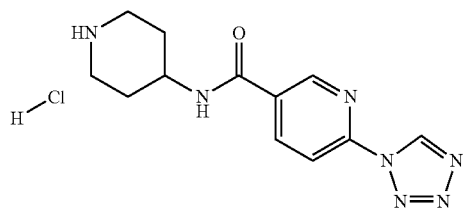

N-(Piperidin-4-yl)-6-(1H-tetrazol-1-yl)nicotinamide hydrochloride

N-(Piperidin-4-yl)-6-(1H-tetrazol-1-yl)nicotinamide hydrochloride was prepared in a similar fashion to that described for the synthesis of INTERMEDIATE 6 starting from 4-amino-1-BOC-piperidine and 6-(1H-tetrazol-1-yl)nicotinic acid. LC-MS (IE, m/z): 274 [M+1]$^+$.

INTERMEDIATE 9, 10A and 10B

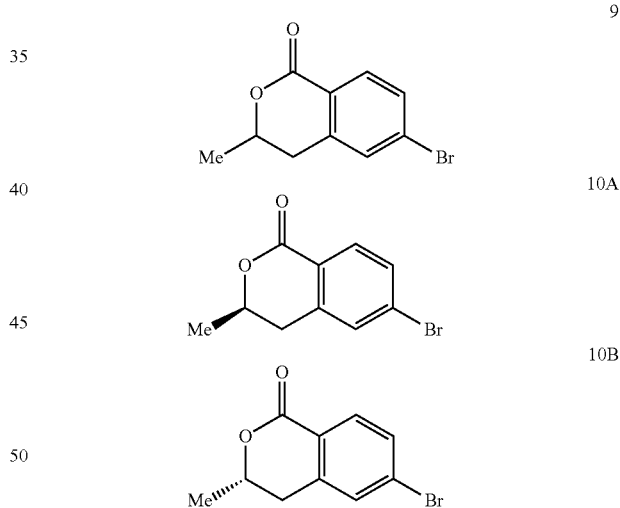

6-bromo-3-methyl-3,4-dihydro-1H-isochromen-1-one and individual isomers (3R)-6-bromo-3-methyl-3,4-dihydro-1H-isochromen-1-one and (3S)-6-bromo-3-methyl-3,4-dihydro-1H -isochromen-1-one A −78° C. solution of diisopropylamine (13.3 mL, 93.0 mmol)) in THF (155 mL) was treated with n-BuLi (1.6 M in Hexanes; 58 mL, 93 mmol) over a period of 15 minutes using a syringe pump. In a separate flask, a solution of 2-methyl-4-bromo benzoic acid (10.0 g, 46.5 mmol) and HMPA (8.33 mL, 46.5 mmol) in THF (155 mL) was cooled to −78° C. Methyl Lithium (29.1 mL, 46.5 mmol) was added slowly via syringe to the cooled solution. The resulting solution was stirred for 10 minutes and then transferred via cannula to the LDA solution at −78° C. The resulting solution was stirred at −78° C. for an additional 1 h before being quenched with anhydrous acetaldehyde (7.88 mL, 140 mmol) and the reaction was then taken out of the dry ice acetone bath and allowed to stir for an additional 1 h. The flask containing the reaction mixture was then resubmerged in the dry ice acetone bath before it was quenched with 4M HCl in dioxane (50 mL) followed by 25 mL of MeOH. The reaction was stirred at room temp for an additional 1 h. The crude reaction mixture was partitioned between 200 mL ethyl acetate and 200 mL water. The organic layer was washed with water, brine, dried with magnesium sulfate, filtered and concentrated. Purification via MPLC (30-70% DCM/Hexanes) afforded 9 as a racemic mixture which was separable by chiral SFC HPLC using, for example, a Chiralpak AS column to obtain Isomer 10A and Isomer 10B. $^1$H NMR (500 MHz; CDCl$_3$): δ 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H); LC-MS (IE, m/z): 241 [M+1]$^+$.

INTERMEDIATE 11

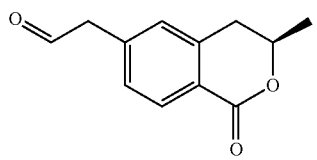

(R)-2-(3-Methyl-1-oxoisochroman-6-yl)acetaldehyde

Step A: (3R)-6-(1,3-Dioxolan-2-ylmethyl)-3-methyl-3,4-dihydro-1H-iso chromen-1-one A sealed tube was charged with aryl bromide, palladium (II) acetate (0.028 g, 0.124 mmol) and tri-t-butylphosphine-BF$_4$ complex (0.072 g, 0.25 mmol) and sealed. The tube was evacuated and refilled with nitrogen before DMF (12 ml) and (3R)-6-bromo-3-methyl-3,4-dihydro-1H -isochromen-1-one (0.75 g, 3.1 mmol) were added followed by bromo (1,3-dioxolan-2-ylmethyl)zinc (6.2 ml, 3.1 mmol). The tube was heated to 110° C. in the microwave for 75 minutes, after which it was cooled, diluted with EtOAc, filtered, concentrated and purified via MPLC (20-50% E/H) to afford the title compound. LC-MS (IE, m/z): 249 [M+1]$^+$.

Step B: tert-Butyl 4-{2-[(3R)-3-methyl-1-oxo-3,4-dihydro-1H-isochromen-6-yl]ethyl}pip erazine-1-carboxylate A 1:1 solution of dioxane:3 N HCl was added to a flask containing (3R)-6-(1,3-dioxolan-2-ylmethyl)-3-methyl-3,4-dihydro-1H-isochromen-1-one (780 mg, 3.2 mmol). The reaction was then stirred at room temperature overnight. The crude reaction mixture was then partitioned between water and DCM. The organic layer was washed with saturated sodium bicarbonate solution, followed by brine. The organic layer was then dried with magnesium sulfate, filtered and concentrated to afford (R)-2-(3-methyl-1-oxoisochroman-6-yl)acetaldehyde which was used directly in the next step without further purification.

INTERMEDIATE 12

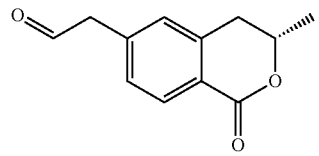

(S)-2-(3-Methyl-1-oxoisochroman-6-yl)acetaldehyde (S)-2-(3-Methyl-1-oxoisochroman-6-yl)acetaldehyde was prepared in a similar manner as (R)-2-(3-methyl-1-oxoisochroman-6-yl)acetaldehyde except starting from (3S)-6-bromo-3-methyl-3,4-dihydro-1H-isochromen-1-one.

INTERMEDIATE 13

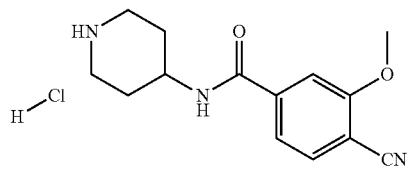

4-Cyano-3-methoxy-N-(piperidin-4-yl)benzamide hydrochloride

4-Cyano-3-methoxy-N-(piperidin-4-yl)benzamide hydrochloride was prepared in a similar fashion to that described for the synthesis of INTERMEDIATE 6 starting from 4-amino-1-BOC-piperidine and 4-cyano-3-methoxybenzoic acid. LC-MS (IE, m/z): 260 [M+1]$^+$.

INTERMEDIATE 14

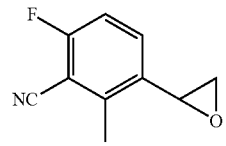

6-Fluoro-2-methyl-3-oxiran-2-ylbenzonitrile

Step A: 3-Bromo-6-fluoro-2-methylbenzonitrile

To a cooled (0° C.) solution of 2-fluoro-6-methylbenzonitrile (5.0 g, 37 mmol) in 100 mL of concentrated H$_2$SO$_4$ was added NBS (6.93 g, 38.9 mmol). Then the mixture was stirred at 0° C. for 3 hrs and poured into ice-water (1 L). The solution was extracted three times with EtOAc (200 mL) and the combined orgianc layers were washed with water and brine, dried over anhydrous sodium sulfate, filtered and concentrated. The residue was purified by silica gel flash chromatography to give the title compound.

Step B: 3-Ethenyl-6-fluoro-2-methylbenzonitrile

A mixture of 3-bromo-6-fluoro-2-methylbenzonitrile (8.8 g, 41 mmol), tributyl(vinyl)tin (14.3 g, 45.2 mmol), LiCl (5.20 g, 123 mmol) and Pd(PPh$_3$)$_4$ (2.3 g, 2.0 mmol) in toluene (200 mL) was heated at 100-110° C. under N$_2$ overnight. The mixture was concentrated and the residue was purified by column chromatography to obtain 3-ethenyl-6-fluoro-2-methylbenzonitrile.

Step C: 6-Fluoro-2-methyl-3-oxiran-2-ylbenzonitrile

To a cooled (0° C.) solution of 3-ethenyl-6-fluoro-2-methylbenzonitrile (6.05 g, 37.6 mmol) in 200 mL of DCM was added m-CPBA (15.30 g, 85% purity, 75.16 mmol). Then the mixture was stirred at r.t. for 12 hrs and diluted with DCM (300 mL), washed with saturated Na$_2$SO$_3$ (4×300 mL) and brine, dried over anhydrous sodium sulfate, filtered and concentrated. The residue was purified by column chromatography to obtain title compound. $^1$H-NMR (400 MHz, CDCl$_3$) δ ppm 7.41~7.44 (m, 1H), 7.02 (t, J=8.6 Hz, 1H), 3.95 (t, J=3.1 Hz, 1H), 3.16~3.19 (m, 1H), 2.60~2.62 (m, 4H).

INTERMEDIATE 15

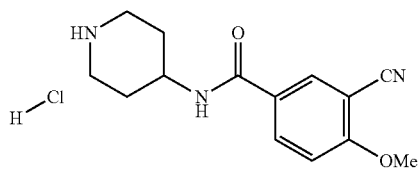

3-Cyano-4-methoxy-N-(piperidin-4-yl)benzamide hydrochloride

3-Cyano-4-methoxy-N-(piperidin-4-yl)benzamide hydrochloride was prepared in a similar fashion to that described for the synthesis of INTERMEDIATE 6 starting from 4-amino-1-BOC-piperidine and 3-cyano-4-methoxybenzoic acid. LC-MS (IE, m/z): 260 [M+1]$^+$.

INTERMEDIATE 16

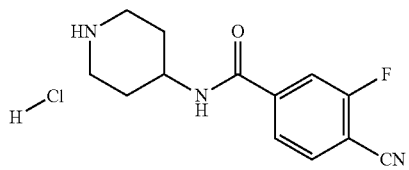

4-Cyano-3-fluoro-N-(piperidin-4-yl)benzamide hydrochloride

4-Cyano-3-fluoro-N-(piperidin-4-yl)benzamide hydrochloride was prepared in a similar fashion to that described for the synthesis of INTERMEDIATE 6 starting from 4-amino-1-BOC-piperidine and 4-cyano-3-fluorobenzoic acid. LC-MS (IE, m/z): 248 [M+1]$^+$.

INTERMEDIATE 17

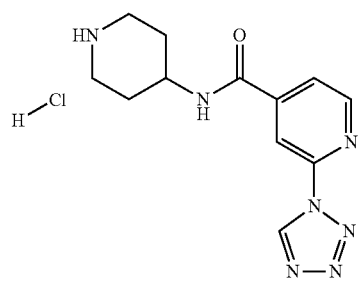

N-(Piperidin-4-yl)-2-(1H-tetrazol-1-yl)isonicotinamide hydrochloride

N-(Piperidin-4-yl)-2-(1H-tetrazol-1-yl)isonicotinamide hydrochloride was prepared in a similar fashion to that described for the synthesis of INTERMEDIATE 6 starting from 4-amino-1-BOC-piperidine and 2-(1H-tetrazol-1-yl)isonicotinic acid. LC-MS (IE, m/z): 310 [M+1]$^+$.

INTERMEDIATE 18

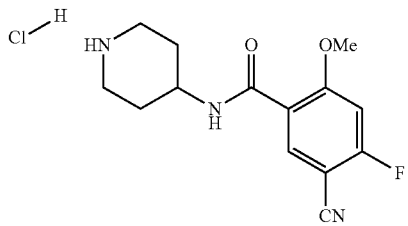

5-Cyano-4-fluoro-2-methoxy-N-(piperidin-4-yl)benzamide hydrochloride

5-Cyano-4-fluoro-2-methoxy-N-(piperidin-4-yl)benzamide hydrochloride was prepared in a similar fashion to that described for the synthesis of INTERMEDIATE 6 starting from 4-amino-1-BOC-piperidine and 5-cyano-4-fluoro-2-methoxybenzoic acid. LC-MS (IE, m/z): 278 [M+1]$^+$.

INTERMEDIATE 19

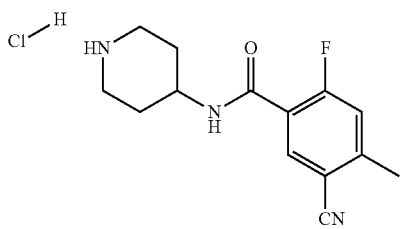

5-Cyano-2-fluoro-4-methyl-N-(piperidin-4-yl)benzamide hydrochloride

5-Cyano-2-fluoro-4-methyl-N-(piperidin-4-yl)benzamide hydrochloride was prepared in a similar fashion to that described for the synthesis of INTERMEDIATE 6 starting from 4-amino-1-BOC-piperidine and 5-cyano-2-fluoro-4-methylbenzoic acid. LC-MS (IE, m/z): 262 [M+1]$^+$.

INTERMEDIATE 20

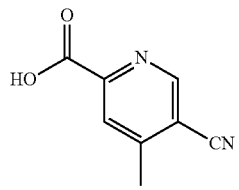

5-Cyano-4-methylpicolinic acid

Step A: Ethyl 5-Cyano-4-methylpicolinate

A mixture of ethyl 5-bromo-4-methylpicolinate, zinc (7.9 mg, 0.12 mmol), zinc cyanide (120 mg, 1.0 mmol), tris(dibenzylideneacetone)dipalladium(0) (55 mg, 0.060 mmol), and 1,1'-bis(diphenylphosphino)ferrocene (67 mg, 0.12 mmol) was flushed with nitrogen, then Ethanol (3.5 mL) was added and the mixture heated at 80° C. for 12 h. The reaction mixture was cooled, diluted with EtOAc, washed successively with 2N aq. NH$_4$OH, and brine, then dried (Na$_2$SO$_4$), filtered and concentrated. Purification by prep TLC (20% EtOAc in hexane) provided ethyl 5-cyano-4-methylpicolinate. $^1$H NMR (400 MHz, CDCl$_3$): δ 8.91 (s, 1H), 8.13 (s, 1H), 4.52 (m, 2H), 2.65 (s, 3H), 1.48 (m, 3H); LC-MS (IE, m/z): 191 [M+1]$^+$.

Step B: 5-Cyano-4-methylpicolinic acid

To a solution of ethyl 5-cyano-4-methylpicolinate (98 mg, 0.52 mmol) in THF (2.6 mL) was added 1.0 N LiOH (2.6 mL, 2.6 mmol) at rt. The reaction mixture was left to stir at rt overnight. The mixture was diluted with EtOAc and H$_2$O. The aqueous layer was extracted with EtOAc. The aqueous layer was collected and 2 mL of 1N HCl was added dropwise. A solid precipitate was collected by filtration and dried under high vacuum to provide 5-cyano-4-methyl picolinic acid. $^1$H NMR (400 MHz, CDCl$_3$): δ 8.87 (s, 1H), 8.10 (s, 1H), 2.78 (s, 3H).

INTERMEDIATE 21

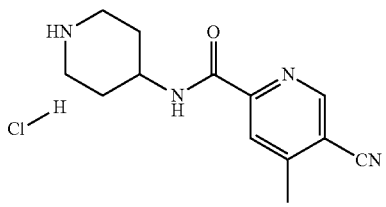

5-Cyano-4-methyl-N-(piperidin-4-yl)picolinamide hydrochloride

5-Cyano-4-methyl-N-(piperidin-4-yl)picolinamide hydrochloride was prepared in a similar fashion to that described for the synthesis of INTERMEDIATE 6 starting from 4-amino-1-BOC-piperidine and 5-cyano-4-methylpicolinic acid. LC-MS (IE, m/z): 281 [M+1]$^+$.

INTERMEDIATE 22

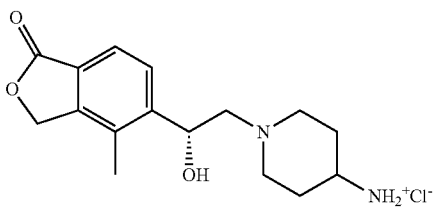

(R)-5-(2-(4-Aminopiperidin-1-yl)-1-hydroxyethyl)-4-methylisobenzofuran-1(3H)-one hydrochloride (R)-5-(2-(4-Aminopiperidin-1-yl)-1-hydroxyethyl)-4-methylisobenzofuran-1(3H)-one hydrochloride was prepared in a similar fashion to that described for the synthesis of INTERMEDIATE 5 starting from tert-butyl piperidin-4-ylcarbamate and 4-methyl-5-[(2R)-oxiran-2-yl]-2-benzofuran-1(3H)-one. LC-MS (IE, m/z): 291 [M+1]$^+$.

INTERMEDIATE 23

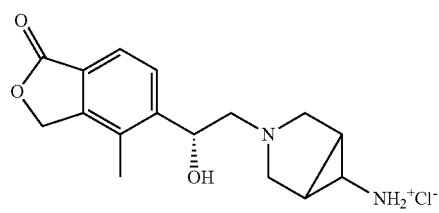

5-((1R)-2-(6-Amino-3-azabicyclo[3.1.0]hexan-3-yl)-1-hydroxyethyl)-4-methylisobenzofuran-1(3H)-one Hydrochloride 5-((1R)-2-(6-Amino-3-azabicyclo[3.1.0]hexan-3-yl)-1-hydroxyethyl)-4-methylisobenzofuran-1(3H)-one hydrochloride was prepared in a similar fashion to that described for the synthesis of INTERMEDIATE 5 starting from commercially available tert-butyl 3-azabicyclo[3.1.0]hexan-6-ylcarbamate and 4-methyl-5-[(2R)-oxiran-2-yl]-2-benzofuran-1(3H)-one. LC-MS (IE, m/z): 289 [M+1]$^+$.

37

INTERMEDIATE 24

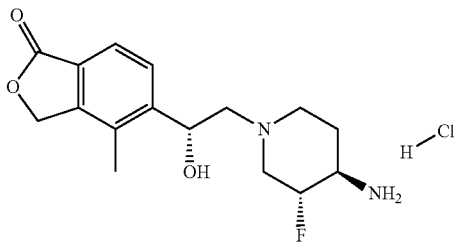

5-((R)-2-((trans)-4-Amino-3-fluoropiperidin-1-yl)-1-hydroxyethyl)-4-methylisobenzofuran-1(3H)-one hydrochloride 5-((R)-2-((trans)-4-Amino-3-fluoropiperidin-1-yl)-1-hydroxyethyl)-4-methylisobenzofuran-1(3H)-one hydrochloride was prepared in a similar fashion to that described for the synthesis of INTERMEDIATE 5 starting from racemic tert-butyl (trans)-3-fluoropiperidin-4-ylcarbamate and 4-methyl-5-[(2R)-oxiran-2-yl]-2-benzofuran-1(3H)-one. LC-MS (IE, m/z): 309 [M+1]$^+$.

INTERMEDIATE 25

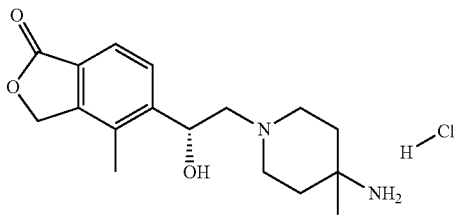

(R)-5-(2-(4-Amino-4-methylpiperidin-1-yl)-1-hydroxyethyl)-4-methylisobenzofuran-1(3H)-one hydrochloride (R)-5-(2-(4-Amino-4-methylpiperidin-1-yl)-1-hydroxyethyl)-4-methylisobenzofuran-1(3H)-one hydrochloride was prepared in a similar fashion to that described for the synthesis of Intermediate 5 starting from tert-butyl 4-amino-4-methylpiperidine-1-carboxylate and 4-methyl-5-[(2R)-oxiran-2-yl]-2-benzofuran-1(3H)-one. LC-MS (IE, m/z): 305 [M+1]$^+$.

INTERMEDIATE 26

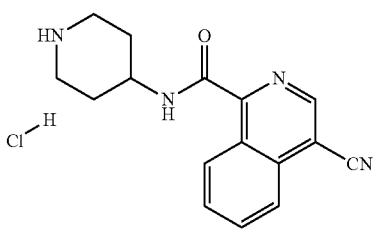

38

4-Cyano-N-(piperidin-4-yl)isoquinoline-1-carboxamide hydrochloride

Step A: tert-Butyl 4-(4-bromoisoquinoline-1-carboxamido)piperidine-1-carboxylate To a solution of 4-bromoisoquinoline-1-carboxylic acid (250 mg, 0.99 mmol) in DMF (5 mL) was added TBTU (380 mg, 1.2 mmol) at room temperature. Reactant 2 (200 mg, 0.99 mmol) and triethylamine (0.28 ml, 2.0 mmol) was then added at room temperature and the resulting mixture stirred for 2 h. The reaction was partitioned between EtOAc and aq NaHCO$_3$ (saturated). The aqueous layer was extracted with EtOAc (twice), and the combined organic phase was washed with brine, dried over anhydrous MgSO$_4$, filtered and concented in vacuo. Purification of the resulting residue by prep TLC (silica gel, 10% MeOH/DCM) provided tert-butyl 4-(4-bromoisoquinoline-1-carboxamido)piperidine-1-carboxylate. LC-MS (IE, m/z): 309 [M+1]$^+$.

Step B: tert-Butyl 4-(4-cyanoisoquinoline-1-carboxamido)piperidine-1-carboxylate To a solution of tert-butyl 4-(4-bromoisoquinoline-1-carboxamido)piperidine-1-carboxylate (290 mg, 0.67 mmol), zinc cyanide (780 mg ml, 6.7 mmol), DPPF (56 mg, 0.10 mmol) and Pd$_2$(dba)$_3$ (92 mg, 0.10 mmol) in DMF (5 mL) was added at room temperature. The reaction mixture was heated in a microwave reactor at 100° C. for 2 h. The reaction mixture was partitioned between EtOAc and aq NaHCO$_3$ (saturated). The aqueous layer was extracted with EtOAc (2×). The aqueous layer was extracted with EtOAc (twice), and the combined organic phase was washed with brine, dried over anhydrous MgSO$_4$, filtered and concented in vacuo. Purification of the resulting residue by Combi-Flash system (Hexanes/EtOAc, 0% to 60% 35 min) provided tert-butyl 4-(4-cyanoisoquinoline-1-carboxamido)piperidine-1-carboxylate. $^1$H-NMR (400 MHz, CDCl$_3$) δ ppm 9.77 (m, 1H), 8.85 (m, 1H), 8.28 (m, 1H), 8.10 (m, 1H), 7.98 (m, 1H), 4.17 (m, 3H), 3.02 (m, 1H), 2.09 (m, 2H), 1.61 (m, 2H), 1.45 (s, 9H); LC-MS (IE, m/z): 381 [M+1]$^+$.

Step C: 4-Cyano-N-(piperidin-4-yl)isoquinoline-1-carboxamide hydrochloride tert-butyl 4-(4-cyanoisoquinoline-1-carboxamido)piperidine-1-carboxylate was dissolved in 15 ml of 4M HCl in 1,4-dioxane and the solution was stirred at room temperature for 30 min. The reaction mixture was concentrated in vacuo and dried under high vacuum to provide 4-cyano-N-(piperidin-4-yl)isoquinoline-1-carboxamide hydrochloride which was used directly without further purification. LC-MS (IE, m/z): 281 [M+1]$^+$.

INTERMEDIATE 27

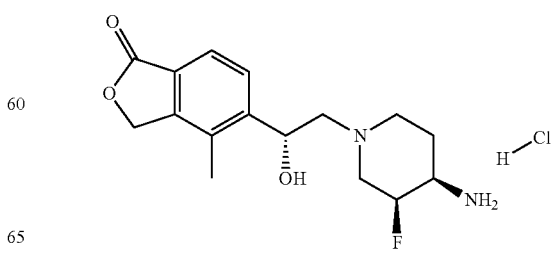

5-((R)-2-((cis)-4-Amino-3-fluoropiperidin-1-yl)-1-hydroxyethyl)-4-methylisobenzofuran-1(3H)-one hydrochloride 5-((R)-2-((cis)-4-Amino-3-fluoropiperidin-1-yl)-1-hydroxyethyl)-4-methylisobenzofuran-1(3H)-one hydrochloride was prepared in a similar fashion to that described for the synthesis of INTERMEDIATE 5 starting from racemic tert-butyl (cis)-3-fluoropiperidin-4-ylcarbamate and 4-methyl-5-[(2R)-oxiran-2-yl]-2-benzofuran-1(3H)-one. LC-MS (IE, m/z): 309 [M+1]$^+$.

INTERMEDIATE 28

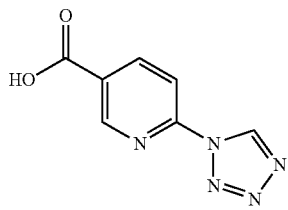 [SMILES: O=C(O)c1ccc(-n2cnnn2)nc1]

6-(1H-Tetrazol-1-yl)nicotinic acid

Step A: Methyl 6-(1H-tetrazol-1-yl)nicotinate

A mixture of methyl 6-aminonicotinate (5.0 g, 33 mmol) in acetic acid (47 ml, 820 mmol) was treated with triethyl orthoformate (8.8 ml, 53 mmol), followed by sodium azide (3.2 g, 49 mmol). The resulting mixture was heated at 80° C. for 1 h, after which the reaction mixture was cooled to room temperature and diluted with water. The resulting precipitate was collected and dried under high vacuum to provide methyl 6-(1H-tetrazol-1-yl)nicotinate. LC-MS (IE, m/z): 206 [M+1]$^+$.

Step B: 6-(1H-Tetrazol-1-yl)nicotinic acid

Methyl 6-(1H-tetrazol-1-yl)nicotinate was dissolved in THF (50 mL) and treated with 1N lithium hydroxide (50 mL) and stirred for 1 h. The mixture was diluted with water and the resulting solid isolated by filtration and drying under high vacuum to provide 6-(1H-tetrazol-1-yl)nicotinic acid. $^1$H-NMR (CDCl$_3$, 500 MHz), δ 9.63 (s, 1H), 9.19 (s, 1H), 8.62 (m, 1H), 8.22 (m, 1H), 4.04 (s, 3H); LC-MS (IE, m/z): 192 [M+1]$^+$.

INTERMEDIATE 29

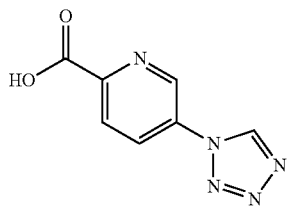 [SMILES: O=C(O)c1ccc(-n2cnnn2)cn1]

5-(1H-Tetrazol-1-yl)picolinic acid 5-(1H-tetrazol-1-yl)picolinic acid was prepared in a similar fashion to that described for the synthesis of INTERMEDIATE 28 starting from methyl 6-aminonicotinate. LC-MS (IE, m/z): 192 [M+1]$^+$.

INTERMEDIATE 30

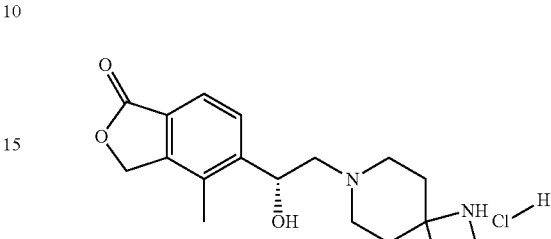

(R)-5-(1-Hydroxy-2-(1,7-diazaspiro[3.5]nonan-7-ypethyl)-4-methylisobenzofuran-1(3H)-one hydrochloride (R)-5-(1-Hydroxy-2-(1,7-diazaspiro[3.5]nonan-7-ypethyl)-4-methylisobenzofuran-1(3H)-one hydrochloride was prepared in a similar fashion to that described for the synthesis of INTERMEDIATE 5 starting from tert-butyl 1,7-diazaspiro[3.5]nonane-1-carboxylate and 4-methyl-5-[(2R)-oxiran-2-yl]-2-benzofuran-1(3H)-one. LC-MS (IE, m/z): 317 [M+1]$^+$.

INTERMEDIATE 31

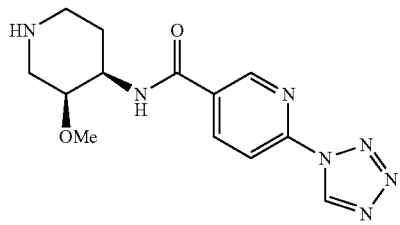 [SMILES: CO[C@H]1CNCC[C@H]1NC(=O)c1ccc(-n2cnnn2)nc1]

N-((cis)-3-Methoxypiperidin-4-yl)-6-(1H-tetrazol-1-yl)picolinamide

Step A: tert-Butyl 4-(6-(1H-tetrazol-1-yl)nicotinamido)-3-methoxypiperidine-1-carboxylate To a solution of cis-4-amino-1-Boc-3-methoxy-piperidine (120 mg, 0.52 mmol), 6-(1H-tetrazol-1-yl)nicotinic acid (100 mg, 0.52 mmol), and TBTU (200 mg, 0.63 mmol) in DMF (2.6 mL) was added triethylamine (180 μl, 1.3 mmol) at RT. The reaction mixture was stirred at RT overnight. The crude was partitioned between EtOAc and saturated aq NaHCO$_3$. The aqueous layer was extracted with EtOAc (twice). The combined organic phase was washed with brine, dried over anhydrous MgSO$_4$, filtered and concentrated in vacuo. The resulting residue was purified by prep TLC (silica gel; 10% MeOH/DCM) to provide tert-butyl 4-(6-(1H-tetrazol-1-yl)nicotinamido)-3-methoxypiperidine-1-carboxylate. $^1$H-NMR (CDCl$_3$, 500 MHz), δ 9.62 (s, 1H), 8.96 (s, 1H), 8.42 (m, 1H), 8.21 (m, 1H), 6.70 (br s, 1H), 4.52 (m, 1H), 4.31 (m, 2H), 4.11 (m, 1H), 3.48 (s, 3H), 2.84 (m, 2H), 1.83 (m, 2H), 1.51 (s, 9H); LC-MS (IE, m/z): 404 [M+1]⁺.

Step B: N-((cis)-3-Methoxypiperidin-4-yl)-6-(1H-tetrazol-1-yl)picolinamide

A solution of tert-butyl 4-(6-(1H-tetrazol-1-yl)nicotinamido)-3-methoxypiperidine-1-carboxylate (190 mg, 0.48 mmol) in 4 N HCl in 1,4-dioxane (5 mL) was stirred at room temperature for 15 min. The solvent was concentrated in vacuo and the resulting salt was stirred in 80:15:1 dichloromethane: methanol: ammonium hydroxide at room temperature and filtered. The filtrate was concentrated to provide N-((cis)-3-methoxypiperidin-4-yl)-6-(1H-tetrazol-1-yl) picolinamide. LC-MS (IE, m/z): 304 [M+1]⁺.

INTERMEDIATE 32

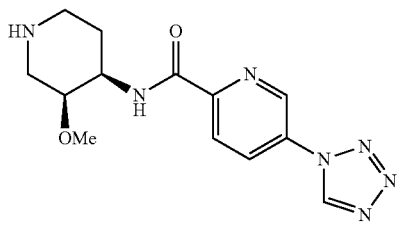 [SMILES: CO[C@H]1CNCC[C@H]1NC(=O)c1ccc(-n2cnnn2)cn1]

N-((cis)-3-Methoxypiperidin-4-yl)-5-(1H-tetrazol-1-yl)picolinamide hydrochloride N-((cis)-3-Methoxypiperidin-4-yl)-5-(1H-tetrazol-1-yl) picolinamide hydrochloride was prepared in a similar fashion to that described for the synthesis of INTERMEDIATE 31 starting from racemic (cis)-tert-butyl 4-amino-3-methoxypiperidine-1-carboxylate and 5-(1H-tetrazol-1-yl) nicotinic acid. LC-MS (IE, m/z): 304 [M+1]⁺.

INTERMEDIATE 33

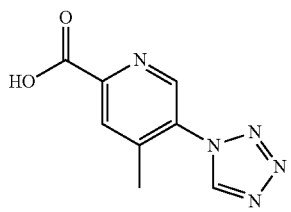

4-Methyl-5-(1H-tetrazol-1-yl)picolinic acid

Step A: Methyl 4-Methyl-5-nitropicolinate

To a solution of 4-methyl-5-nitro-2-pyridinecarboxylic acid (1.0 g, 5.5 mmol) in methanol (50 mL) was added concentrated HCl (8 mL, 97 mmol) at room temperature. The mixture was heated at reflux for 18 h, then cooled to room temperature. The crude mixture was partitioned between EtOAc and saturated NaHCO₃ and the aqueous layer was extracted with EtOAc (twice). The combined organic phase was washed with brine, dried over anhydrous MgSO₄, filtered and concentrated to provide methyl 4-methyl-5-nitropicolinate. ¹H-NMR (CDCl₃, 500 MHz), δ 9.23 (s, 1H), 8.16 (s, 1H), 4.06 (s, 3H), 2.77 (s, 3H).

Step B: Methyl 5-Amino-4-methylpicolinate

To a solution of methyl 4-methyl-5-nitropicolinate (810 mg, 4.1 mmol) in ethanol (150 ml) was added palladium on carbon (10 wt. %, 85 mg, 4.1 mmol) at room temperature. Hydrogenation was carried out in a parr shaker at 45 psi for 3 h. Additional palladium on carbon was added (170 mg) and the reaction was continued at 39 psi for 23 h. The mixture was filtered through CELITE® and concentrated to provide methyl 5-amino-4-methylpicolinate, which was directly used in the next step without further purification. LC-MS (IE, m/z): 167 [M+1]⁺.

Step C: Methyl 4-Methyl-5-(1H-tetrazol-1-yl)picolinate

To a mixture of methyl 5-amino-4-methylpicolinate (650 mg, 3.9 mmol) in acetic acid (2.2 mL, 390 mmol) was added triethyl orthoformate (1.0 mL, 6.3 mmol), followed by sodium azide (380 mg, 5.9 mmol). The mixture was heated at 80° C. for 12 h, then cooled to room temperature. The reaction mixture was partitioned between water and EtOAc. The aqueous layer was extracted with EtOAc (twice), and the combined organic phase was washed with brine, dried over anhydrous MgSO₄, filtered, and concentrated in vacuo. Purification of the resulting residue by prep TLC (silica gel, 10% MeOH/DCM) provided methyl 4-methyl-5-(1H-tetrazol-1-yl)picolinate. ¹H-NMR (CDCl₃, 500 MHz), δ 8.97 (s, 1H), 8.75 (s, 1H), 8.26 (s, 1H), 4.09 (s, 3H), 2.44 (s, 3H).

Step D: 4-Methyl-5-(1H-tetrazol-1-yl)picolinic acid

To a solution of 4-methyl-5-(1H-tetrazol-1-yl)picolinate (180 mg, 0.82 mmol) in tetrahydrofuran (4.1 mL) was added 1 N lithium hydroxide solution (1.1 mL, 1.1 mmol) at room temperature. The reaction mixture was left to stir at room temperature for 3 h. The mixture was diluted with EtOAc and water. The aqueous layer was extracted with EtOAc. The aqueous layer was collected and 3 mL of 1 N HCl was added dropwise. The resulting clear solution was concentrated in vacuo to provide 4-Methyl-5-(1H-tetrazol-1-yl) picolinic acid.

¹H-NMR (DMSO-D₆, 500 MHz), δ 9.91 (s, 1H), 8.82 (s, 1H), 8.20 (s, 1H), 2.26 (s, 3H).

INTERMEDIATE 34

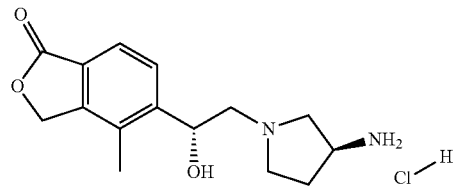

5-((R)-2-((S)-3-Aminopyrrolidin-1-yl)-1-hydroxyethyl)-4-methylisobenzofuran-1(3H)-one hydrochloride 5-((R)-2-((S)-3-Aminopyrrolidin-1-yl)-1-hydroxyethyl)-4-methylisobenzofuran-1(3H)-one hydrochloride was prepared in a similar fashion to that described for the synthesis of INTERMEDIATE 5 starting from (S)-tert-butyl pyrrolidin-3-ylcarbamate and 4-methyl-5-[(2R)-oxiran-2-yl]-2-benzofuran-1(3H)-one. LC-MS (IE, m/z): 277 [M+1]⁺.

INTERMEDIATE 35

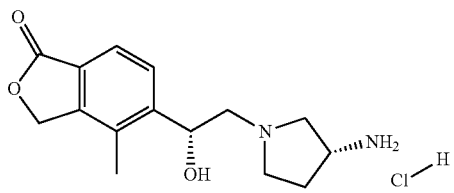

5-((R)-2-((R)-3-Aminopyrrolidin-1-yl)-1-hydroxyethyl)-4-methylisobenzofuran-1(3H)-one hydrochloride 5-((R)-2-((R)-3-Aminopyrrolidin-1-yl)-1-hydroxyethyl)-4-methylisobenzofuran-1(3H)-one hydrochloride was prepared in a similar fashion to that described for the synthesis of INTERMEDIATE 5 starting from (R)-tert-butyl pyrrolidin-3-ylcarbamate and 4-methyl-5-[(2R)-oxiran-2-yl]-2-benzofuran-1(3H)-one. LC-MS (IE, m/z): 277 [M+1]⁺.

INTERMEDIATE 36

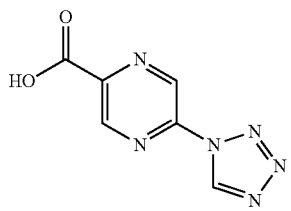 [SMILES: O=C(O)c1cnc(-n2cnnn2)cn1]

5-(1H-Tetrazol-1-yl)pyrazine-2-carboxylic acid 5-(1H-Tetrazol-1-yl)pyrazine-2-carboxylic acid was prepared in a similar fashion to that described for the synthesis of INTERMEDIATE 28 starting from methyl 6-aminonicotinate. LC-MS (IE, m/z): 193 [M+1]⁺.

INTERMEDIATE 37

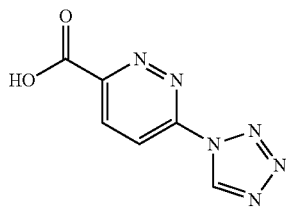 [SMILES: O=C(O)c1ccc(-n2cnnn2)nn1]

6-(1H-Tetrazol-1-yl)pyridazine-3-carboxylic acid 6-(1H-Tetrazol-1-yl)pyridazine-3-carboxylic acid was prepared in a similar fashion to that described for the synthesis of INTERMEDIATE 28 starting from methyl 6-aminonicotinate. ¹H-NMR (CD₃OD 500 MHz), δ 10.21 (s, 1H), 8.53 (s, 2H); LC-MS (IE, m/z): 193 [M+1]⁺.

INTERMEDIATE 38

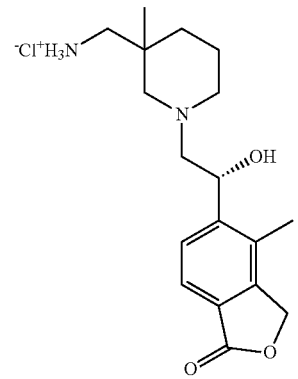

5-[(R)-2-[3-(Aminomethyl)-3-methylpiperidin-1-yl]-1-hydroxyethyl}-4-methyl-2-benzofuran1(3H)-one hydrochloride 5-[(R)-2-[3-(Aminomethyl)-3-methylpiperidin-1-yl]-1-hydroxyethyl}-4-methyl-2-benzofuran1(3H)-one hydrochloride was prepared in a similar fashion to that described for the synthesis of INTERMEDIATE 5 starting from tert-butyl [(3-methylpiperidin-3-yl)methyl]carbamate and 4-methyl-5-[(2R)-oxiran-2-yl]-2-benzofuran-1(3H)-one. LC-MS (IE, m/z): 319 [M+1]⁺.

INTERMEDIATE 39

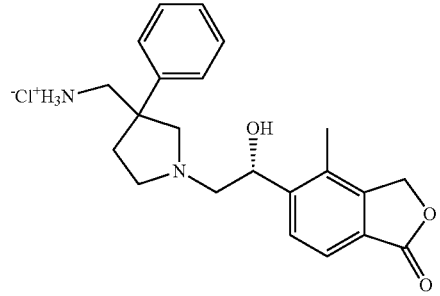

5-[(R)-2-[3-(Aminomethyl)-3-phenylpyrrolidin-1-yl]-1-hydroxyethyl}-4-methyl-2-benzofuran-1(3H)-one Hydrochloride 5-[(R)-2-[3-(Aminomethyl)-3-phenylpyrrolidin-1-yl]-1-hydroxyethyl}-4-methyl-2-benzofuran-1(3H)-one hydrochloride was prepared in a similar fashion to that described for the synthesis of INTERMEDIATE 5 starting from tert-butyl[(3-methylpyrrolidin-3-yl)methyl]carbamate and 4-methyl-5-[(2R)-oxiran-2-yl]-2-benzofuran-1(3H)-one. LC-MS (IE, m/z): 367 [M+1]⁺.

INTERMEDIATE 40

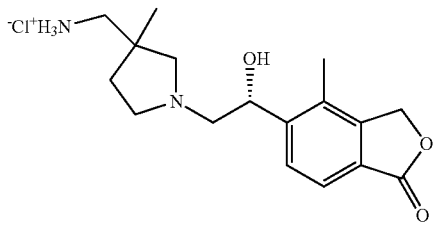

5-[(R)-2-[3-(Aminomethyl)-3-methylpyrrolidin-1-yl]-1-hydroxyethyl}-4-methyl-2-benzofuran-1(3H)-one hydrochloride 5-[(R)-2-[3-(Aminomethyl)-3-methylpyrro lidin-1-yl]-1-hydroxyethyl}-4-methyl-2-benzofuran-1(3H)-one hydrochloride was prepared in a similar fashion to that described for the synthesis of INTERMEDIATE 5 starting from tert-butyl[(3-methylpyrrolidin-3-yl)methyl]carbamate and 4-methyl-5-[(2R)-oxiran-2-yl]-2-benzofuran-1(3H)-one. LC-MS (IE, m/z): 305 [M+1]⁺.

INTERMEDIATE 41

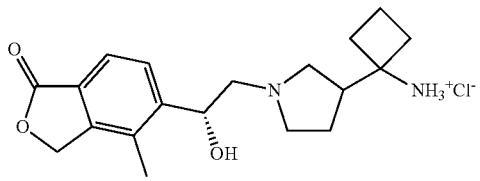

1-(1-((R)-2-Hydroxy-2-(4-methyl-1-oxo-1,3-dihydroisobenzofuran-5-yl)ethyl)pyrrolidin-3-yl)cyclobutanaminium chloride 1-(1-((R)-2-Hydroxy-2-(4-methyl-1-oxo-1,3-dihydroisobenzofuran-5-yl)ethyl)pyrrolidin-3-yl)cyclobutanaminium chloride was prepared in a similar fashion to that described for the synthesis of INTERMEDIATE 5 starting from tert-butyl (1-(pyrrolidin-3-yl)cyclobutyl)carbamate and 4-methyl-5-[(2R)-oxiran-2-yl]-2-benzofuran-1(3H)-one. LC-MS (IE, m/z): 331 [M+1]⁺.

INTERMEDIATE 42

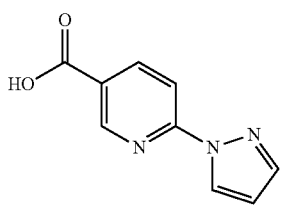 [SMILES: O=C(O)c1ccc(-n2cccn2)nc1]

6-(1H-Pyrazol-1-yl)pyridine-3-carboxylic acid

To a solution of ethyl 6-(1H-pyrazol-1-yl)pyridine-3-carboxylate (50 mg, 0.23 mmol) in THF (1 mL) was added an aqueous solution of lithium hydroxide (1 N, 230 μL). The reaction was stirred at ambient temperature for two hours. After two hours, the reaction was further diluted with water and purified by reverse phase HPLC to afford 6-(1H-pyrazol-1-yl)pyridine-3-carboxylic acid. LC-MS (IE, m/z): 190 [M+1]⁺.

INTERMEDIATE 43

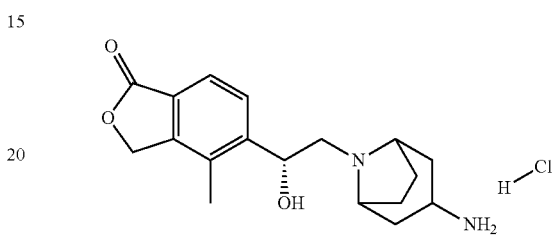

5-((1R)-2-(3-Amino-8-azabicyclo[3.2.1]octan-8-yl)-1-hydroxyethyl)-4-methylisobenzofuran-1(3H)-one Hydrochloride 5-((1R)-2-(3-Amino-8-azabicyclo[3.2.1]octan-8-yl)-1-hydroxyethyl)-4-methylisobenzofuran-1(3H)-one hydrochloride was prepared in a similar fashion to that described for the synthesis of INTERMEDIATE 5 starting from tert-butyl 8-azabicyclo[3.2.1]octan-3-ylcarbamate and 4-methyl-5-[(2R)-oxiran-2-yl]-2-benzofuran-1(3H)-one. LC4MS (IE, m/z): 317 [M+1]⁺.

INTERMEDIATE 44

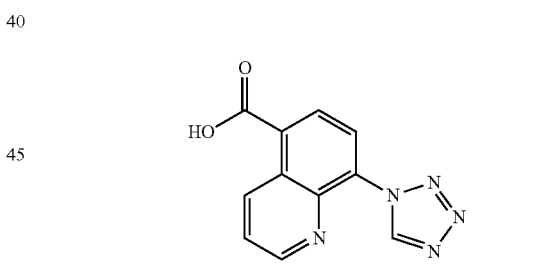

6-(1H-Pyrazol-1-yl)pyridine-3-carboxylic acid

Step A: methyl 8-aminoquinoline-5-carboxylate

A solution 5-bromoquinolin-8-amine (260 mg, 1.2 mmol) in DMF (4 mL) was placed in a sealed tube and degassed with carbon monoxide for 10 minutes. In a separate sealed tube, a solution of PdCl₂(dppf) (85 mg, 0.12 mmol), triethylamine (490 μL, 3.5 mmol) in methanol (4 mL) was degassed with carbon monoxide for 10 minutes. The palladium solution was then added to the amine, placed under a balloon atmosphere of carbon monoxide and heated to 70° C. for 15 hours. The cooled reaction was then filtered over a pad of CELITE® and extracted from water using ethyl acetate. The organic layers were dried over sodium sulfate, filtered and concentrated in vacuo. The crude material was purified via MPLC (0-100% EtOAc/hexanes gradient) to afford methyl 8-aminoquinoline-5-carboxylate. LC-MS (IE, m/z): 203 [M+1]+.

Step B: methyl 8-(1H-tetrazol-1-yl)quinoline-5-carboxylate

To a solution of 8-aminoquinoline-5-carboxylate (167 mg, 0.826 mmol) in glacial acetic acid (4 mL) was added triethyl orthoformate (413 µL, 2.48 mmol) and sodium azide (161 mg, 2.49 mmol). The reaction mixture was heated at 80° C. for 3 hours in a sealed vial and then cooled to ambient temperature. Once cooled, water (5 mL) and solid sodium bicarbonate were added until a pH range of 6-7 was achieved. The aqueous layer was extracted with ethyl acetate (3×10 mL). The combined organic layers were then dried over sodium sulfate, filtered and concentrated in vacuo. The crude residue was purified via MPLC (0-100% EtOAc/Hex gradient) to afford methyl 8-(1H-tetrazol-1-yl)quinoline-5-carboxylate. LC-MS (IE, m/z): 228 [M+1]+.

Step C: 8-(1H-tetrazol-1-yl)quinoline-5-carboxylic acid

To a solution of methyl 8-(1H-tetrazol-1-yl)quinoline-5-carboxylate (100 mg, 0.392 mmol) in THF (2 mL) was added 800 µL of 1N aqueous sodium hydroxide solution. The reaction mixture was allowed to stir at ambient temperature for 90 minutes and then concentrated in vacuo. The crude residue was purified via reverse phase reverse-phase HPLC (TMC Pro-Pac C18; 10-100% 0.1% trifluoroacetic acid in acetonitrile/0.1% trifluoroacetic acid in water gradient) to afford 8-(1H-tetrazol-1-yl)quinoline-5-carboxylic acid. LC-MS (IE, m/z): 242 [M+1]+.

INTERMEDIATE 45

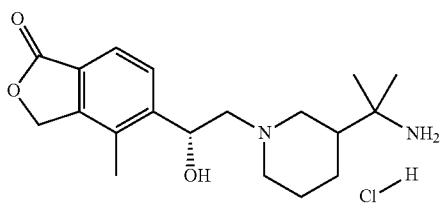

5-((1R)-2-(3-(2-Aminopropan-2-yl)piperidin-1-yl)-1-hydroxyethyl)-4-methylisobenzofuran-1(3H)-one hydrochloride 5-((1R)-2-(3-(2-Aminopropan-2-yl)piperidin-1-yl)-1-hydroxyethyl)-4-methylisobenzofuran-1(3H)-one hydrochloride was prepared in a similar fashion to that described for the synthesis of INTERMEDIATE 5 starting from tert-butyl 2-(piperidin-3-yl)propan-2-ylcarbamate and 4-methyl-5-[(2R)-oxiran-2-yl]-2-benzofuran-1(3H)-one. LC-MS (IE, m/z): 333 [M+1]+.

INTERMEDIATE 46

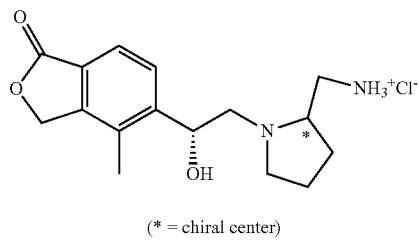

(* = chiral center)

5-[(1R)-2-[2-(Aminomethyl)pyrrolidin-1-yl]-1-hydroxyethyl}-4-methyl-2-benzofuran-1(3H)-one hydrochloride Step A: tert-Butyl ({1-[(2R)-2-hydroxy-2-(4-methyl-1-oxo-1,3-dihydro-2-benzofuran-5-yl)ethyl]pyrrolidin-2-yl}methyl)carbamate A solution of 4-methyl-5-[(2R)-oxiran-2-yl]-2-benzofuran-1(3H)-one (1.0 g, 5.0 mmol) in 25 mL ethanol was added to tert-butyl (pyrrolidin-2-ylmethyl)carbamate (950 mg, 5.0 mmol). The reaction mixture was microwaved at 140° C. for 55 minutes and then the solvent was removed in vacuo. The resulting racemic residue was purified by HPLC to afford two isomers of the title compound: Isomer A: LC-MS (IE, m/z): 391 [M+1]+. Isomer B: LC-MS (IE, m/z): 391 [M+1]+.

Step B: 5-{(1R)-2-[2-(Aminomethyl)pyrrolidin-1-yl]-1-hydroxyethyl}-4-methyl-2-benzofuran-1(3H)-one hydrochloride A suspension of Isomer A from Step A (710 mg, 1.82 mmol) in dioxane (2.0 mL) was treated with a solution of hydrochloric acid in dioxane (4.0 M, 2.0 mL). After shaking sixteen hours, the solvents were removed in vacuo to provide the resulting diastereomer of the title compound which was carried on without further purification. LC-MS (IE, m/z): 291 [M+1]+.

INTERMEDIATE 47

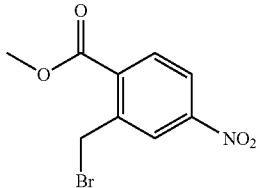

Methyl 2-(bromomethyl)-4-nitrobenzoate

To solution of methyl 2-methyl-4-nitrobenzoate (350 mg, 1.8 mmol) in carbon tetrachloride (6 mL) was added NBS (500 mg, 2.8 mmol) and benzoyl peroxide (13 mg, 0.054 mmol). The reaction was then heated to 70° C. for 15 hours and then cooled to ambient temperature. Once cooled, water (5 mL) was added and the aqueous layer was extracted with dichloromethane (3×10 mL). The combined organic layers were then dried over sodium sulfate, filtered and concentrated in vacuo. The crude residue was purified via MPLC (0-30% EtOAc/Hex gradient) to afford methyl 2-(bromomethyl)-4-nitrobenzoate. $^1$H NMR (500 MHz, DMSO-d$_6$): 9 (s, 1H), 8.3 (d, 1H), 8.1 (d, 1H), 7.9 (s, 1H), 4.9 (s, 2H), 4.0 (s, 3H).

In the following Examples and above Intermediates, Isomer A and Isomer B refer to the faster eluting and slower eluting diastereomers, respectively, based on the observed elution order of the individual diastereomer upon separation from its isomer mixture. Except for a defined chiral center in the parent mixture, absolute stereochemistry of each of the separated Isomers A and B was not determined.

EXAMPLE 1

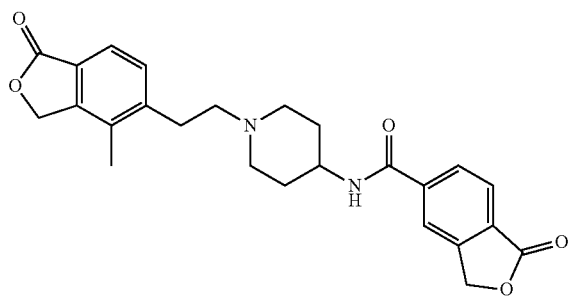 [SMILES: Cc1c(CCN2CCC(NC(=O)c3ccc4c(c3)COC4=O)CC2)ccc2c1COC2=O]

N-(1-(2-(4-Methyl-1-oxo-1,3-dihydroisobenzofuran-5-yl)ethyl)piperidin-4-yl)-1-oxo-1,3-dihydroisobenzofuran-5-carboxamide To a solution of 1-oxo-N-(piperidin-4-yl)-1,3-dihydroisobenzofuran-5-carboxamide hydrochloride (40 mg, 0.12 mmol) in methanol (3 mL) was added (4-methyl-1-oxo-1,3-dihydro-2-benzofuran-5-yl)acetaldehyde (34 mg, 0.18 mmol) at room temperature. The mixture was left to stir for 10 min, and then sodium cyanoborohydride (11 mg, 0.18 mmol) was added to the mixture, followed by dropwise addition of 10% acetic acid (0.40 mL). The reaction mixture was left to stir at rt for 4 h. The mixture was concentrated in vacuo, and the residue was purified by prep TLC (silica gel; 10% methanol/dichloromethane) to provide the title compound. $^1$H NMR (500 MHz; DMSO-D$_6$): 8.59 (br s, 1H), 8.08, (s, 1H), 8.01 (d, J=8.0 Hz, 1H), 7.95 (d, J=8.0 Hz, 1H), 7.62 (d, J=7.5 Hz, 1H), 7.43 (d, J=7.5 Hz, 1H), 5.47 (s, 2H), 5.39 (s, 2H), 3.82 (m, 1H), 3.03 (m, 2H), 2.91 (m, 2H), 2.58 (m, 2H), 2.24 (s, 3H), 2.09 (m, 2H), 1.88 (m, 2H), 1.62 (m, 2H); LC-MS (IE, m/z): 435.

EXAMPLE 2

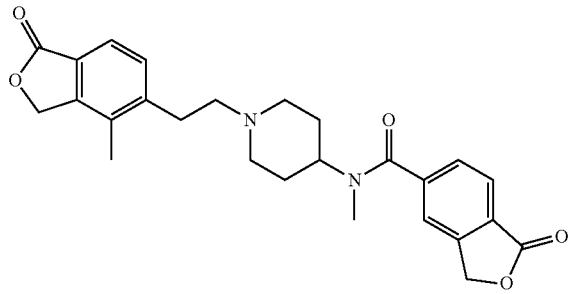 [SMILES: Cc1c(CCN2CCC(N(C)C(=O)c3ccc4c(c3)COC4=O)CC2)ccc2c1COC2=O]

N-Methyl-N-(1-(2-(4-methyl-1-oxo-1,3-dihydroisobenzofuran-5-yl)ethyl)piperidin-4-yl)-1-oxo-1,3-dihydroisobenzofuran-5-carboxamide N-Methyl-N-(1-(2-(4-methyl-1-oxo-1,3-dihydroisobenzofuran-5-yl)ethyl)piperidin-4-yl)-1-oxo-1,3-dihydroisobenzofuran-5-carboxamide was prepared in a similar fashion to that described for the synthesis of EXAMPLE 1 starting from tert-butyl 4-(N-methyl-1-oxo-1,3-dihydroisobenzofuran-5-carboxamido)piperidine-1-carboxylate and (4-methyl-1-oxo-1,3-dihydro-2-benzofuran-5-yl)acetaldehyde. $^1$H NMR (500 MHz; DMSO-D$_6$): 8.02 (d, J=8.0 Hz, 1H), 7.77 (m, 1H), 7.58 (m, 2H), 7.39 (m, 1H), 5.41 (s, 2H), 5.28 (s, 2H), 4.65 (m, 1H), 3.03 (m, 4H), 2.91 (m, 2H), 2.84 (s, 3H), 2.56 (m, 2H), 2.24 (s, 3H), 2.09 (m, 2H), 1.89 (m, 2H), 1.60 (m, 2H); LC-MS (IE, m/z): 449.

EXAMPLE 3

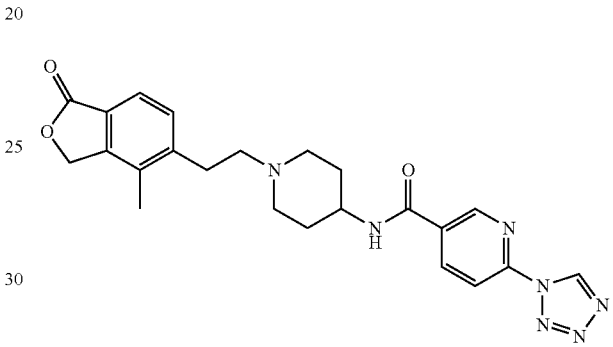

N-(1-(2-(4-Methyl-1-oxo-1,3-dihydroisobenzofuran-5-yl)ethyl)piperidin-4-yl)-6-(1H-tetrazol-1-yl)nicotinamide N-(1-(2-(4-Methyl-1-oxo-1,3-dihydroisobenzofuran-5-yl)ethyl)piperidin-4-yl)-6-(1H-tetrazol-1-yl)nicotinamide was prepared in a similar fashion to that described for the synthesis of EXAMPLE 1 starting from N-(piperidin-4-yl)-6-(1H-tetrazol-1-yl)nicotinamide hydrochloride and (4-methyl-1-oxo-1,3-dihydro-2-benzofuran-5-yl)acetaldehyde. $^1$H NMR (500 MHz; DMSO-D$_6$): 10.26 (s, 1H), 9.03 (s, 1H), 8.69 (m, 1H), 8.19 (m, 1H), 7.62 (d, J=7.5 Hz, 1H), 7.42 (d, J=7.5 Hz, 1H), 5.39 (s, 2H), 3.82 (m, 1H), 3.01 (m, 2H), 2.93 (m, 2H), 2.56 (m, 2H), 2.52 (s, 3H), 2.12 (m, 2H), 1.84 (m, 2H), 1.60 (m, 2H); LC-MS (IE, m/z): 448.

EXAMPLE 4

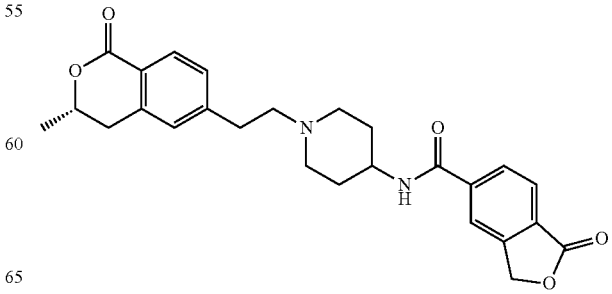

(S)-N-(1-(2-(3-methyl-1-oxoisochroman-6-yl)ethyl) piperidin-4-yl)-1-oxo-1,3-dihydroisobenzofuran-5-carboxamide (S)-N-(1-(2-(3-methyl-1-oxoisochroman-6-yl)ethyl)piperidin-4-yl)-1-oxo-1,3-dihydroisobenzofuran-5-carboxamide was prepared in a similar fashion to that described for the synthesis of EXAMPLE 1 starting from 1-oxo-N-(piperidin-4-yl)-1,3-dihydroisobenzofuran-5-carboxamide hydrochloride and (S)-2-(3-Methyl-1-oxoisochroman-6-yl)acetaldehyde.
$^1$H NMR (500 MHz; CDCl$_3$): 8.10-7.98 (m, 3H), 7.39 (m, 1H), 7.24 (m, 1H), 7.12 (s, 1H), 6.35 (m, 1H), 5.41 (s, 2H), 4.72 (m, 1H), 4.17 (m, 1H), 3.19 (m, 2H), 2.95 (m, 4H), 2.84 (m, 2H), 2.45 (m, 2H), 2.18 (m, 2H), 1.83 (m, 2H), 1.58 (s, 3H), 1.19 (m, 2H); LC-MS (IE, m/z): 449.

EXAMPLE 5

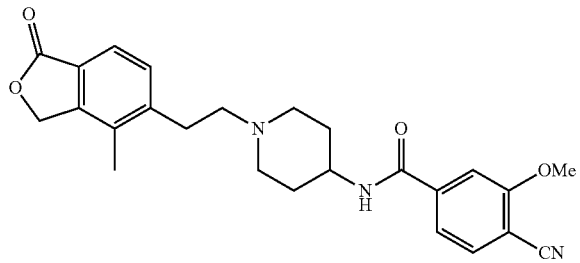 [SMILES: COc1cc(C(=O)NC2CCN(CCc3ccc4c(c3C)COC4=O)CC2)ccc1C#N]

4-Cyano-3-methoxy-N-(1-(2-(4-methyl-1-oxo-1,3-dihydroisobenzofuran-5-yl)ethyl)piperidin-4-yl)benzamide 4-Cyano-3-methoxy-N-(1-(2-(4-methyl-1-oxo-1,3-dihydroisobenzofuran-5-yl)ethyl)piperidin-4-yl)benzamide was prepared in a similar fashion to that described for the synthesis of EXAMPLE 1 starting from 4-cyano-3-methoxy-N-(piperidin-4-yl)benzamide hydrochloride and (4-methyl-1-oxo-1,3-dihydro-2-benzofuran-5-yl)acetaldehyde. $^1$H NMR (500 MHz; CDCl$_3$): 7.74 (d, J=7.5 Hz, 1H), 7.64 (d, J=7.5 Hz, 1H), 7.52 (s, 1H), 7.38 (d, J=7.5 Hz, 1H), 7.29 (m, 1H), 6.13 (br s, 1H), 5.29 (s, 2H), 4.09 (m, 1H), 4.03 (s, 3H), 3.13 (m, 2H), 3.02 (m, 2H), 2.65 (m, 2H), 2.38 (m, 2H), 2.36 (s, 3H), 2.18 (m, 2H), 1.71 (m, 2H); LC-MS (IE, m/z): 434.

EXAMPLE 6

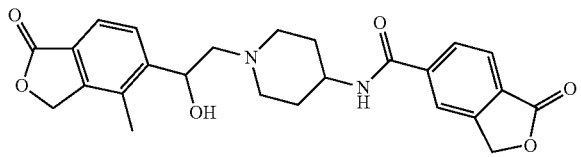 [SMILES: Cc1c(C(O)CN2CCC(NC(=O)c3ccc4c(c3)COC4=O)CC2)ccc2c1COC2=O]

N-(1-(2-Hydroxy-2-(4-methyl-1-oxo-1,3-dihydroisobenzofuran-5-yl)ethyl)piperidin-4-yl)-1-oxo-1,3-dihydroisobenzofuran-5-carboxamide 1-Oxo-N-(piperidin-4-yl)-1,3-dihydroisobenzofuran-5-carboxamide hydrochloride (250 mg, 0.84 mmol) was dissolved in DCM:MeOH:NH$_4$OH, 80:15:1 and purified by prep TLC (silica gel, DCM:MeOH:NH$_4$OH, 80:15:1) to provide 88 mg of neutralized oil. To a mixture of this oil (88 mg, 0.34 mmol) in ethanol (3 ml) was added 4-methyl-5-oxiran-2-yl-2-benzofuran-1(3H)-one (130 mg, 0.68 mmol) at rt. The reaction mixture was heated in a microwave reactor at 150° C. for 1 h. The mixture was concentrated and purified by prep TLC (silica gel; 10% MeOH/DCM) to provide the title compound. LC-MS (IE, m/z): 451.

EXAMPLE 7

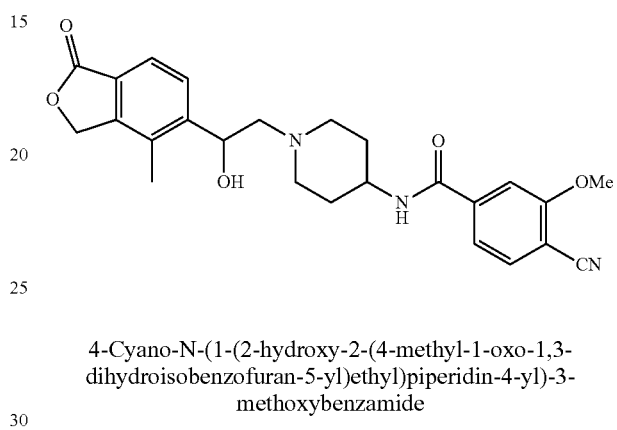

4-Cyano-N-(1-(2-hydroxy-2-(4-methyl-1-oxo-1,3-dihydroisobenzofuran-5-yl)ethyl)piperidin-4-yl)-3-methoxybenzamide 4-Cyano-N-(1-(2-hydroxy-2-(4-methyl-1-oxo-1,3-dihydroisobenzofuran-5-yl)ethyl)piperidin-4-yl)-3-methoxybenzamide was prepared in a similar fashion to that described for the synthesis of EXAMPLE 6 starting from 4-cyano-3-methoxy-N-(piperidin-4-yl)benzamide hydrochloride and (4-methyl-5-oxiran-2-yl-2-benzofuran-1(3H)-one. LC-MS (IE, m/z): 450.

EXAMPLE 8

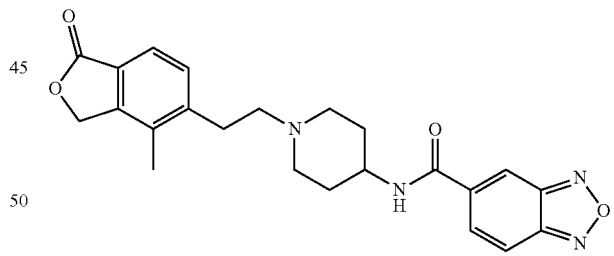

N-(1-(2-(4-Methyl-1-oxo-1,3-dihydroisobenzofuran-5-yl)ethyl)piperidin-4-yl)benzo[c][1,2,5]oxadiazole-5-carboxamide To a solution of 1-[2-(4-methyl-1-oxo-1,3-dihydro-2-benzofuran-5-yl)ethyl]piperidin-4-aminium chloride (120 mg, 0.35 mmol), benzo[c][1,2,5]oxadiazole-5-carboxylic acid (57 mg, 0.35 mmol), and DIPEA (0.18 ml, 1.0 mmol) in DMF (2 ml) was added EDC (79 mg, 0.42 mmol) at rt. The reaction mixture was stirred at rt overnight. The mixture was partitioned between EtOAc and aqueous NaHCO$_3$ (saturated). The aqueous layer was extracted twice with EtOAc; the combined organic phase was washed with brine, dried over anhydrous MgSO₄, filtered, and concentrated. The resulting residue was purified by prep TLC (silica gel; 10% MeOH/DCM) to provide the title compound.

¹H NMR (500 MHz; CDCl₃): 8.21 (s, 1H), 7.95 (d, J=7.5 Hz, 1H), 7.85 (d, J=7.5 Hz, 1H), 7.71 (d, J=7.5 Hz, 1H), 7.28 (d, J=7.5 Hz, 1H), 6.17 (m, 1H), 5.26 (s, 2H), 4.08 (m, 1H), 3.05 (m, 2H), 2.98 (m, 2H), 2.62 (m, 2H), 2.33 (s, 3H), 2.15 (m, 2H), 1.68 (m, 2H).

EXAMPLE 9

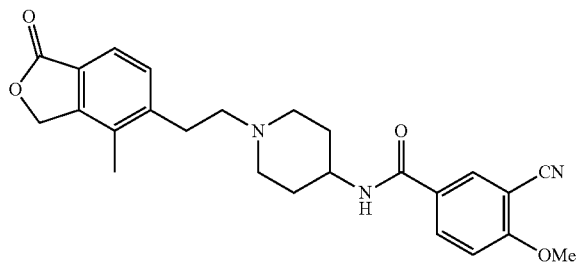 [SMILES: COc1ccc(C(=O)NC2CCN(CCc3ccc4c(c3C)COC4=O)CC2)cc1C#N]

3-Cyano-4-methoxy-N-(1-(2-(4-methyl-1-oxo-1,3-dihydroisobenzofuran-5-yl)ethyl)piperidin-4-yl)benzamide The title compound was prepared in a similar fashion to that described for the synthesis of EXAMPLE 8 starting from 1-[2-(4-methyl-1-oxo-1,3-dihydro-2-benzofuran-5-yl)ethyl]piperidin-4-aminium chloride and 3-cyano-4-methoxybenzoic acid. ¹H NMR (500 MHz; CDCl₃): 8.03 (d, J=7.5 Hz, 1H), 7.99 (s, 1H), 7.71 (d, J=7.5 Hz, 1H), 7.28 (d, J=7.5 Hz, 1H), 7.02 (d, J=7.5 Hz, 1H), 5.98 (m, 1H), 5.23 (s, 2H), 4.04 (m, 1H), 4.00 (s, 3H), 2.99 (m, 4H), 2.61 (m, 2H), 2.30 (s, 3H), 2.10 (m, 2H), 1.62 (m, 2H);LC-MS (IE, m/z): 434.

EXAMPLE 10

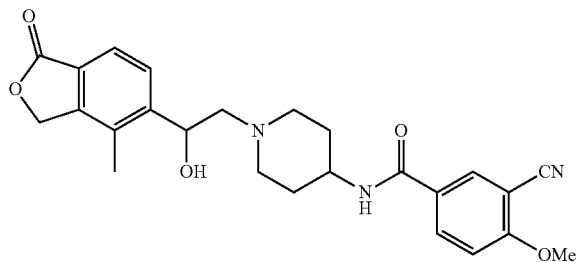 [SMILES: COc1ccc(C(=O)NC2CCN(CC(O)c3ccc4c(c3C)COC4=O)CC2)cc1C#N]

3-Cyano-N-(1-(2-hydroxy-2-(4-methyl-1-oxo-1,3-dihydroisobenzofuran-5-yl)ethyl)piperidin-4-yl)-4-methoxybenzamide The title compound was prepared in a similar fashion to that described for the synthesis of EXAMPLE 6 starting from 1-[2-(4-methyl-1-oxo-1,3-dihydro-2-benzofuran-5-yl)ethyl]piperidin-4-aminium chloride and 4-methyl-5-oxiran-2-yl-2-benzofuran-1(3H)-one. LC-MS (IE, m/z): 450.

EXAMPLE 11

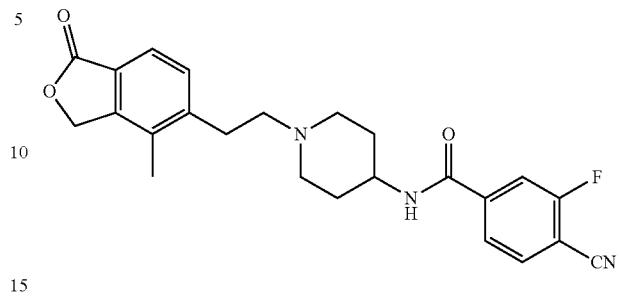

4-Cyano-3-fluoro-N-(1-(2-(4-methyl-1-oxo-1,3-dihydroisobenzofuran-5-yl)ethyl)piperidin-4-yl)benzamide The title compound was prepared in a similar fashion to that described for the synthesis of EXAMPLE 8 starting from 1-[2-(4-methyl-1-oxo-1,3-dihydro-2-benzofuran-5-yl)ethyl]piperidin-4-aminium chloride and 4-cyano-3-fluorobenzoic acid. ¹H NMR (500 MHz; CDCl₃): 7.75 (m, 2H), 7.63 (m, 2H), 7.38 (d, J=7.5 Hz, 1H), 6.04 (m, 1H), 5.26 (s, 2H), 4.04 (m, 1H), 2.99 (m, 4H), 2.63 (m, 2H), 2.30 (s, 3H), 2.13 (m, 2H), 1.64 (m, 2H).

EXAMPLE 12

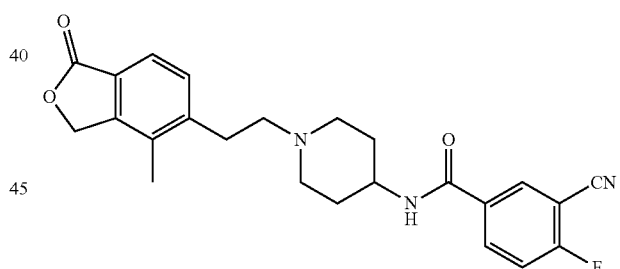

3-Cyano-4-fluoro-N-(1-(2-(4-methyl-1-oxo-1,3-dihydroisobenzofuran-5-yl)ethyl)piperidin-4-yl)benzamide The title compound was prepared in a similar fashion to that described for the synthesis of EXAMPLE 8 starting from 1-[2-(4-methyl-1-oxo-1,3-dihydro-2-benzofuran-5-yl)ethyl]piperidin-4-aminium chloride and 3-cyano-4-fluorobenzoic acid. ¹H NMR (500 MHz; CDCl₃): 8.08 (m, 2H), 7.62 (d, J=7.5 Hz, 1H), 7.33 (m, 2H), 6.18 (m, 1H), 5.25 (s, 2H), 4.03(m, 1H), 2.97 (m, 4H), 2.63 (m, 2H), 2.30 (s, 3H), 2.13 (m, 2H), 1.63 (m, 2H);LC-MS (IE, m/z): 422.

EXAMPLE 13

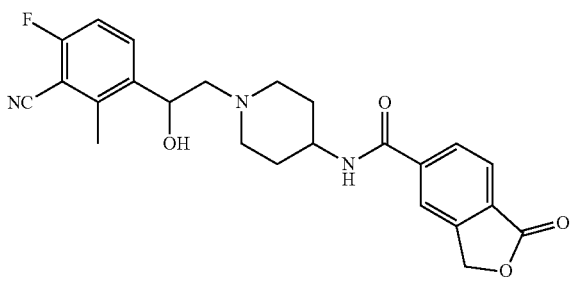 [SMILES: Cc1c(C(O)CN2CCC(NC(=O)c3ccc4c(c3)COC4=O)CC2)ccc(F)c1C#N]

N-(1-(2-(3-Cyano-4-fluoro-2-methylphenyl)-2-hydroxyethyl)piperidin-4-yl)-1-oxo-1,3-dihydroisobenzofuran-5-carboxamide The title compound was prepared in a similar fashion to that described for the synthesis of EXAMPLE 6 starting from 1-oxo-N-(piperidin-4-yl)-1,3-dihydroisobenzofuran-5-carboxamide hydrochloride and 6-Fluoro-2-methyl-3-oxiran-2-ylbenzonitrile. LC-MS (IE, m/z): 438.

EXAMPLE 14

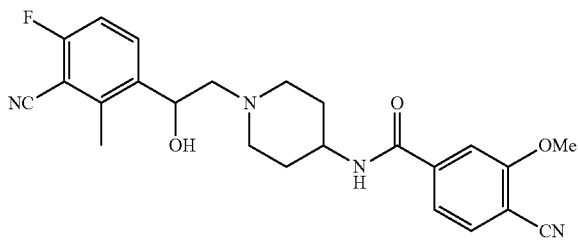 [SMILES: COc1cc(C(=O)NC2CCN(CC(O)c3ccc(F)c(C#N)c3C)CC2)ccc1C#N]

4-Cyano-N-(1-(2-(3-cyano-4-fluoro-2-methylphenyl)-2-hydroxyethyl)piperidin-4-yl)-3-methoxybenzamide The title compound was prepared in a similar fashion to that described for the synthesis of EXAMPLE 6 starting from 14-cyano-3-methoxy-N-(piperidin-4-yl)benzamide hydrochloride and 6-Fluoro-2-methyl-3-oxiran-2-ylbenzonitrile. LC-MS (IE, m/z): 437.

EXAMPLE 15

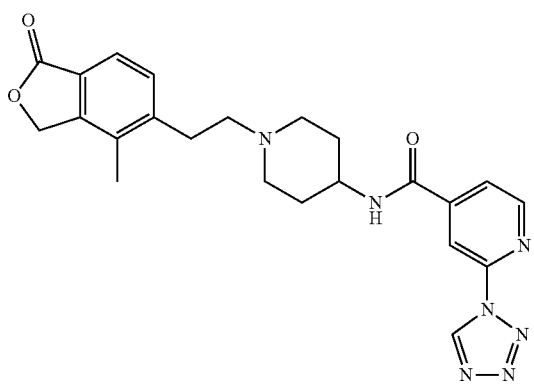 [SMILES: Cc1c(CCN2CCC(NC(=O)c3ccnc(-n4cnnn4)c3)CC2)ccc2c1COC2=O]

N-(1-(2-(4-Methyl-1-oxo-1,3-dihydroisobenzofuran-5-yl)ethyl)piperidin-4-yl)-2-(1H-tetrazol-1-yl)isonicotinamide The title compound was prepared in a similar fashion to that described for the synthesis of EXAMPLE 1 starting from N-(piperidin-4-yl)-2-(1H-tetrazol-1-yl)isonicotinamide hydrochloride and (4-methyl-1-oxo-1,3-dihydro-2-benzofuran-5-yl)acetaldehyde. LC-MS (IE, m/z): 448.

EXAMPLE 16

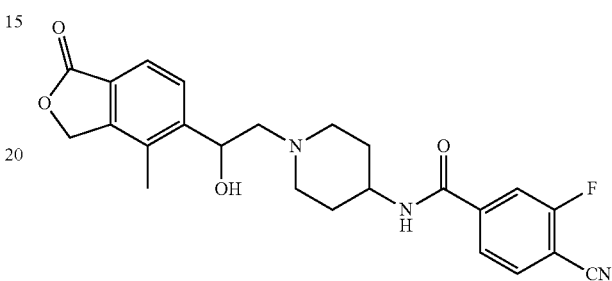

4-Cyano-3-fluoro-N-(1-(2-hydroxy-2-(4-methyl-1-oxo-1,3-dihydroisobenzofuran-5-yl)ethyl)piperidin-4-yl)benzamide The title compound was prepared in a similar fashion to that described for the synthesis of EXAMPLE 6 starting from 4-cyano-3-fluoro-N-(piperidin-4-yl)benzamide hydrochloride and 4-methyl-5-oxiran-2-yl-2-benzofuran-1(3H)-one. LC-MS (IE, m/z): 438.

EXAMPLE 17

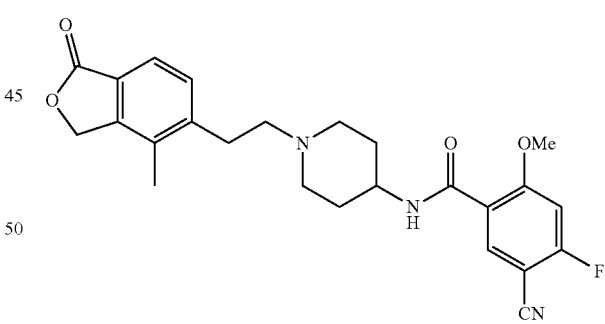

5-Cyano-4-fluoro-2-methoxy-N-(1-(2-(4-methyl-1-oxo-1,3-dihydroisobenzofuran-5-yl)ethyl)piperidin-4-yl)benzamide The title compound was prepared in a similar fashion to that described for the synthesis of EXAMPLE 1 starting from 5-cyano-4-fluoro-2-methoxy-N-(piperidin-4-yl)benzamide hydrochloride and (4-methyl-1-oxo-1,3-dihydro-2-benzofuran-5-yl)acetaldehyde. $^1$H NMR (500 MHz; DMSO-$D_6$): 7.97 (m, 1H), 7.61 (m, 1H), 7.43 (m, 1H), 7.38 (m, 1H), 5.39 (s, 2H), 3.97 (s, 3H), 3.80 (m, 1H), 2.97 (m, 4H), 2.53 (m, 2H), 2.25 (s, 3H), 2.11 (m, 2H), 1.88 (m, 2H), 1.58 (m, 2H); LC-MS (IE, m/z): 452.

EXAMPLE 18

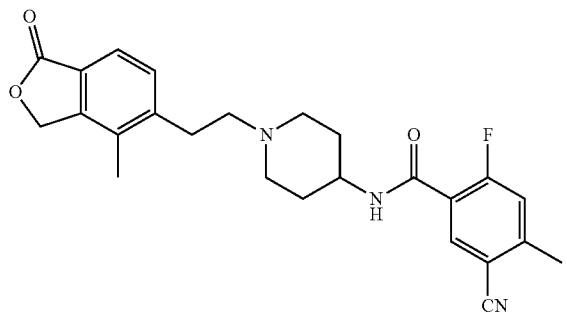 [SMILES: Cc1cc(F)c(C(=O)NC2CCN(CCc3ccc4c(c3C)COC4=O)CC2)cc1C#N]

5-Cyano-2-fluoro-4-methyl-N-(1-(2-(4-methyl-1-oxo-1,3-dihydroisobenzofuran-5-yl)ethyl)piperidin-4-yl)benzamide The title compound was prepared in a similar fashion to that described for the synthesis of EXAMPLE 1 starting from 5-cyano-2-fluoro-4-methyl-N -(piperidin-4-yl)benzamide hydrochloride and (4-methyl-1-oxo-1,3-dihydro-2-benzofuran-5-yl)acetaldehyde. LC-MS (IE, m/z): 436.

EXAMPLE 19

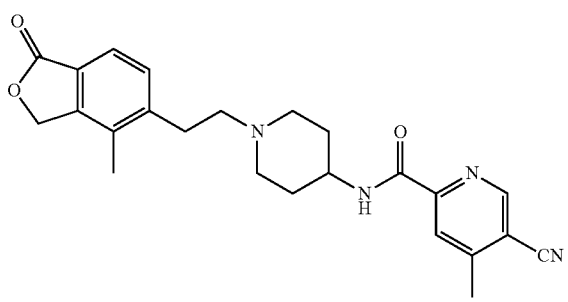 [SMILES: Cc1cc(C(=O)NC2CCN(CCc3ccc4c(c3C)COC4=O)CC2)ncc1C#N]

5-Cyano-4-methyl-N-(1-(2-(4-methyl-1-oxo-1,3-dihydroisobenzofuran-5-yl)ethyl)piperidin-4-yl)picolinamide The title compound was prepared in a similar fashion to that described for the synthesis of EXAMPLE 1 starting from 5-cyano-4-methyl-N-(piperidin-4-yl)picolinamide hydrochloride and (4-methyl-1-oxo-1,3-dihydro-2-benzofuran-5-yl)acetaldehyde. LC-MS (IE, m/z): 419.

EXAMPLE 20

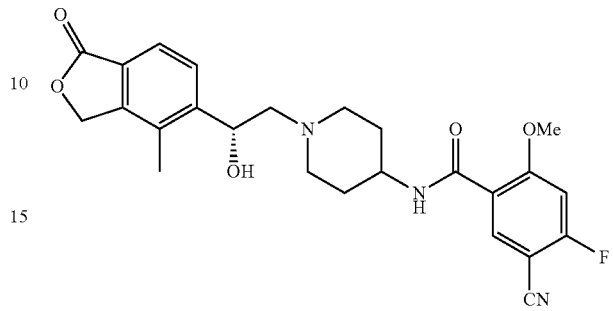

(R)-5-Cyano-4-fluoro-N-(1-(2-hydroxy-2-(4-methyl-1-oxo-1,3-dihydroisobenzofuran-5-yl)ethyl)piperidin-4-yl)-2-methoxybenzamide The title compound was prepared in a similar fashion to that described for the synthesis of EXAMPLE 6 starting from 5-cyano-4-fluoro-2-methoxy-N-(piperidin-4-yl)benzamide hydrochloride and (R)-4-methyl-5-oxiran-2-yl-2-benzofuran-1(3H)-one. $^1$H NMR (500 MHz; CDCl$_3$): 8.52 (m, 1H), 7.82 (m, 2H), 7.68 (m, 1H), 6.90 (m, 1H), 5.69 (m, 1H), 5.37 (m, 1H), 5.29 (m, 2H), 4.35 (m, 1H), 4.16 (m, 1H), 4.09 (s, 3H), 3.89 (m, 1H), 3.25 (m, 1H), 3.06 (m, 3H), 2.34 (s, 3H), 2.22 (m, 4H); LC-MS (IE, m/z): 468.

EXAMPLE 21

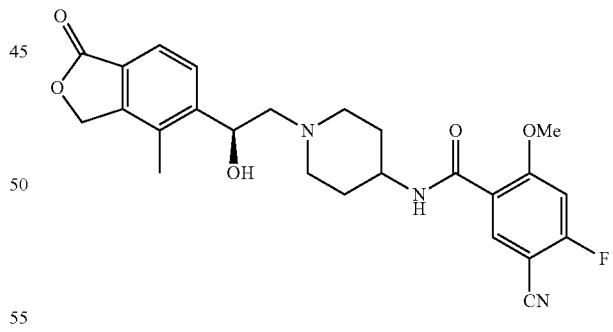

(S)-5-Cyano-4-fluoro-N-(1-(2-hydroxy-2-(4-methyl-1-oxo-1,3-dihydroisobenzofuran-5-yl)ethyl)piperidin-4-yl)-2-methoxybenzamide The title compound was prepared in a similar fashion to that described for the synthesis of EXAMPLE 6 starting from 5-cyano-4-fluoro-2-methoxy-N-(piperidin-4-yl)benzamide hydrochloride and (S)-4-methyl-5-oxiran-2-yl-2-benzofuran-1(3H)-one. LC-MS (IE, m/z): 468.

EXAMPLE 22

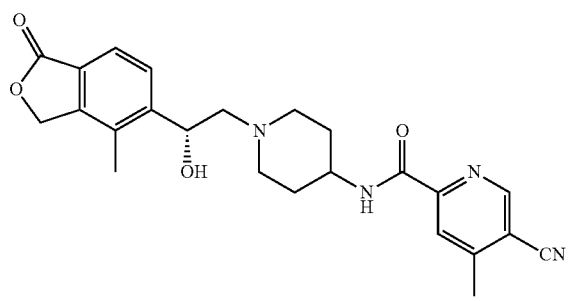 [SMILES: Cc1cc(C(=O)NC2CCN(C[C@H](O)c3ccc4c(c3C)COC4=O)CC2)ncc1C#N]

(R)-5-cyano-N-(1-(2-hydroxy-2-(4-methyl-1-oxo-1,
3-dihydroisobenzofuran-5-yl)ethyl)piperidin-4-yl)-4-
methylpicolinamide The title compound was prepared in a similar fashion to that described for the synthesis of EXAMPLE 6 starting from 5-cyano-4-methyl-N-(piperidin-4-yl)picolinamide hydrochloride and (R)-4-methyl-5-oxiran-2-yl-2-benzofuran-1(3H)-one. $^1$H NMR (500 MHz; CDCl$_3$): 8.78 (m, 1H), 8.17 (m, 2H), 7.83 (m, 2H), 5.72 (m, 1H), 5.28 (m, 2H), 4.27 (m, 1H), 4.16 (m, 1H), 3.98 (m, 1H), 3.25 (m, 1H), 3.14 (m, 3H), 2.68 (s, 3H), 2.36 (s, 3H), 2.20 (m, 4H); LC-MS (IE, m/z): 435.

EXAMPLE 23

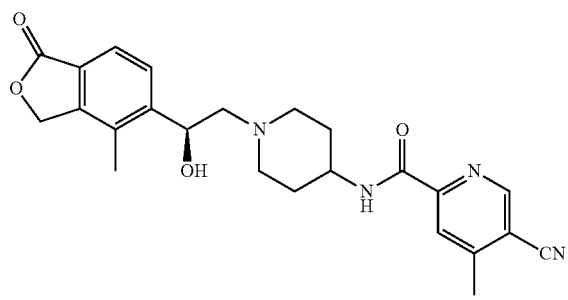 [SMILES: Cc1cc(C(=O)NC2CCN(C[C@@H](O)c3ccc4c(c3C)COC4=O)CC2)ncc1C#N]

(S)-5-cyano-N-(1-(2-hydroxy-2-(4-methyl-1-oxo-1,
3-dihydroisobenzofuran-5-yl)ethyl)piperidin-4-yl)-4-
methylpicolinamide The title compound was prepared in a similar fashion to that described for the synthesis of EXAMPLE 6 starting from 5-cyano-4-methyl-N-(piperidin-4-yl)picolinamide hydrochloride and (S)-4-methyl-5-oxiran-2-yl-2-benzofuran-1(3H)-one. $^1$H NMR (500 MHz; CDCl$_3$): 8.77 (m, 1H), 8.16 (m, 2H), 7.83 (m, 2H), 5.68 (m, 1H), 5.24 (m, 2H), 4.85 (m, 1H), 4.25 (m, 1H), 4.15 (m, 1H), 3.96 (m, 1H), 3.25 (m, 1H), 3.15 (m, 3H), 2.67 (s, 3H), 2.34 (s, 3H), 2.22 (m, 4H); LC-MS (IE, m/z): 435.

EXAMPLE 24

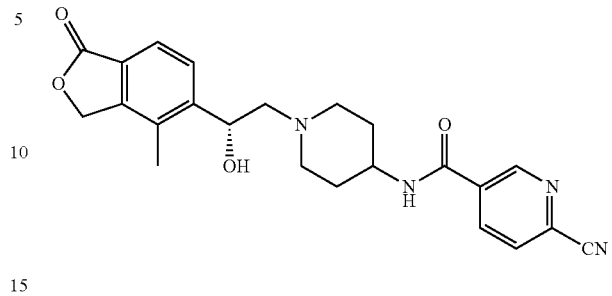

(R)-6-Cyano-N-(1-(2-hydroxy-2-(4-methyl-1-oxo-1,
3-dihydroisobenzofuran-5-yl)ethyl)piperidin-4-yl)
nicotinamide The title compound was prepared in a similar fashion to that described for the synthesis of EXAMPLE 8 starting from (R)-5-(2-(4-Aminopiperidin-1-yl)-1-hydroxyethyl)-4-methylisobenzofuran-1(3H)-one hydrochloride and 6-cyanonicotinic acid. LC-MS (IE, m/z): 421.

EXAMPLE 25

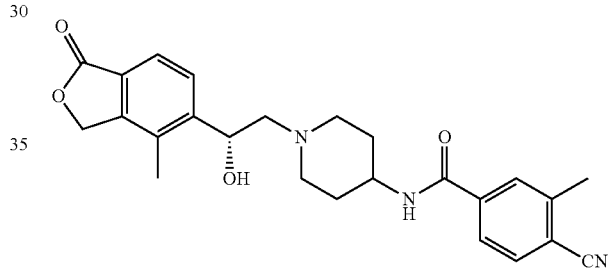

(R)-4-Cyano-N-(1-(2-hydroxy-2-(4-methyl-1-oxo-1,
3-dihydroisobenzofuran-5-yl)ethyl)piperidin-4-yl)-3-
methylbenzamide The title compound was prepared in a similar fashion to that described for the synthesis of EXAMPLE 8 starting from (R)-5-(2-(4-Aminopiperidin-1-yl)-1-hydroxyethyl)-4-methylisobenzofuran-1(3H)-one hydrochloride and 4-cyano-3-methylbenzoic acid. LC-MS (IE, m/z): 434.

EXAMPLE 26

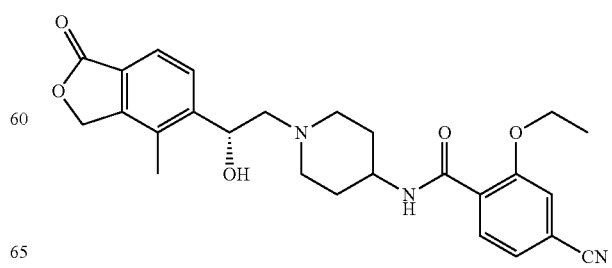

(R)-4-Cyano-2-ethoxy-N-(1-(2-hydroxy-2-(4-methyl-1-oxo-1,3-dihydroisobenzofuran-5-yl)ethyl)piperidin-4-yl)benzamide The title compound was prepared in a similar fashion to that described for the synthesis of EXAMPLE 8 starting from (R)-5-(2-(4-Aminopiperidin-1-yl)-1-hydroxyethyl)-4-methylisobenzofuran-1(3H)-one hydrochloride and 4-cyano-2-ethoxybenzoic acid. LC-MS (IE, m/z): 464.

EXAMPLE 27

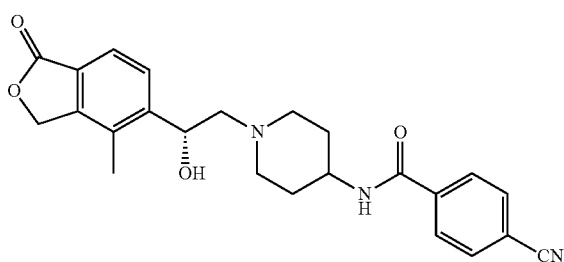 [SMILES: Cc1c([C@@H](O)CN2CCC(NC(=O)c3ccc(C#N)cc3)CC2)ccc2c1COC2=O]

(R)-4-Cyano-N-(1-(2-hydroxy-2-(4-methyl-1-oxo-1,3-dihydroisobenzofuran-5-yl)ethyl)piperidin-4-yl)benzamide The title compound was prepared in a similar fashion to that described for the synthesis of EXAMPLE 8 starting from (R)-5-(2-(4-Aminopiperidin-1-yl)-1-hydroxyethyl)-4-methylisobenzofuran-1(3H)-one hydrochloride and benzoic acid. LC-MS (IE, m/z): 420.

EXAMPLE 28

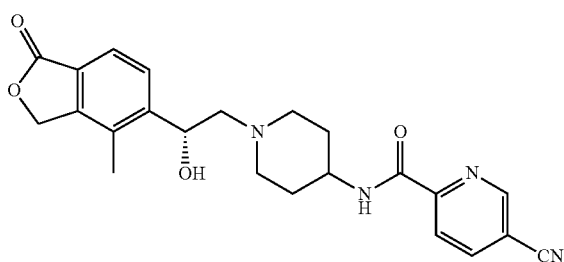 [SMILES: Cc1c([C@@H](O)CN2CCC(NC(=O)c3ccc(C#N)cn3)CC2)ccc2c1COC2=O]

(R)-5-Cyano-N-(1-(2-hydroxy-2-(4-methyl-1-oxo-1,3-dihydroisobenzofuran-5-yl)ethyl)piperidin-4-yl)picolinamide The title compound was prepared in a similar fashion to that described for the synthesis of EXAMPLE 8 starting from (R)-5-(2-(4-Aminopiperidin-1-yl)-1-hydroxyethyl)-4-methylisobenzofuran-1(3H)-one hydrochloride and 5-cyanopicolinic acid. $^1$H NMR (500 MHz; CDCl$_3$): 9.12 (s, 1H), 8.55 (m, 1H), 8.19 (m, 1H), 7.79 (m, 2H), 5.72 (m, 1H), 5.28 (m, 2H), 4.27 (m, 1H), 4.16 (m, 1H), 3.98 (m, 1H), 3.25 (m, 1H), 3.14 (m, 3H), 2.36 (s, 3H), 2.20 (m, 4H); LC-MS (IE, m/z): 421.

EXAMPLE 29

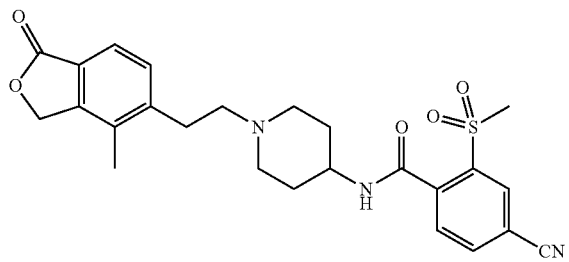 [SMILES: Cc1c(CCN2CCC(NC(=O)c3ccc(C#N)cc3S(C)(=O)=O)CC2)ccc2c1COC2=O]

4-Cyano-N-(1-(2-(4-methyl-1-oxo-1,3-dihydroisobenzofuran-5-yl)ethyl)piperidin-4-yl)-2-(methylsulfonyl)benzamide The title compound was prepared in a similar fashion to that described for the synthesis of EXAMPLE 8 starting from 1-[2-(4-methyl-1-oxo-1,3-dihydro-2-benzofuran-5-yl)ethyl]piperidin-4-aminium chloride and 4-cyano-2-(methylsulfonyl)benzoic acid. LC-MS (IE, m/z): 482.

EXAMPLE 30

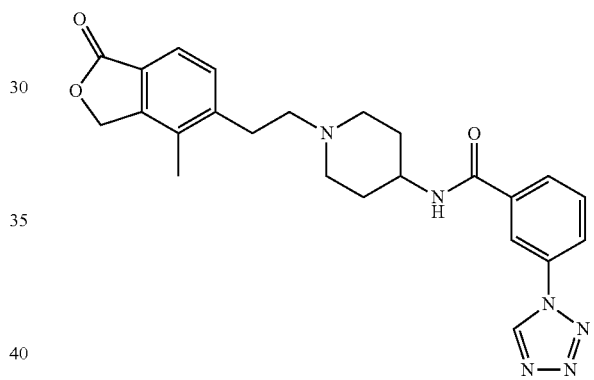

N-(1-(2-(4-Methyl-1-oxo-1,3-dihydroisobenzofuran-5-yl)ethyl)piperidin-4-yl)-3-(1H-tetrazol-1-yl)benzamide The title compound was prepared in a similar fashion to that described for the synthesis of EXAMPLE 8 starting from 1-[2-(4-methyl-1-oxo-1,3-dihydro-2-benzofuran-5-yl)ethyl]piperidin-4-aminium chloride and 3-(1H-tetrazol-1-yl)benzoic acid. LC-MS (IE, m/z): 447.

EXAMPLE 31

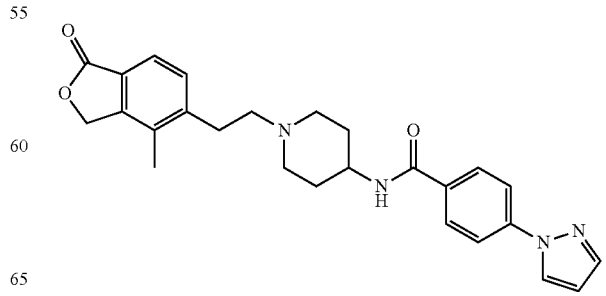

N-(1-(2-(4-Methyl-1-oxo-1,3-dihydroisobenzofuran-5-yl)ethyl)piperidin-4-yl)-4-(1H-pyrazol-1-yl)benzamide The title compound was prepared in a similar fashion to that described for the synthesis of EXAMPLE 8 starting from 1-[2-(4-methyl-1-oxo-1,3-dihydro-2-benzofuran-5-yl)ethyl]piperidin-4-aminium chloride and 4-(1H-pyrazol-1-yl)benzoic acid. LC-MS (IE, m/z): 445.

EXAMPLE 32

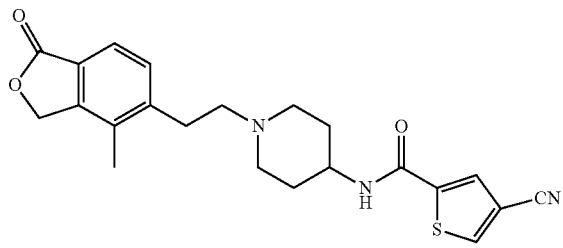 [SMILES: Cc1c(CCN2CCC(NC(=O)c3cc(C#N)cs3)CC2)ccc2c1COC2=O]

4-Cyano-N-(1-(2-(4-methyl-1-oxo-1,3-dihydroisobenzofuran-5-yl)ethyl)piperidin-4-yl)thiophene-2-carboxamide The title compound was prepared in a similar fashion to that described for the synthesis of EXAMPLE 8 starting from 1-[2-(4-methyl-1-oxo-1,3-dihydro-2-benzofuran-5-yl)ethyl]piperidin-4-aminium chloride and 4-cyanothiophene-2-carboxylic acid. LC-MS (IE, m/z): 410.

EXAMPLE 33

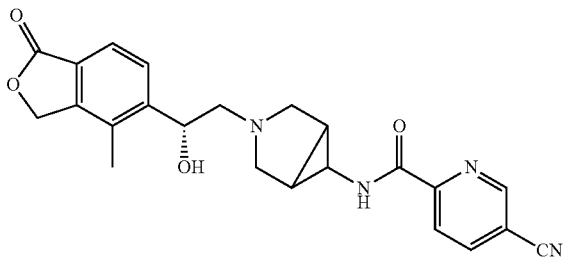 [SMILES: Cc1c([C@@H](O)CN2CC3C(C2)C3NC(=O)c2ccc(C#N)cn2)ccc2c1COC2=O]

5-Cyano-N-(3-((R)-2-hydroxy-2-(4-methyl-1-oxo-1,3-dihydroisobenzofuran-5-yl)ethyl)-3-azabicyclo[3.1.0]hexan-6-yl)picolinamide The title compound was prepared in a similar fashion to that described for the synthesis of EXAMPLE 8 starting from 5-((1R)-2-(6-amino-3-azabicyclo[3.1.0]hexan-3-yl)-1-hydroxyethyl)-4-methylisobenzofuran-1(3H)-one hydrochloride and 5-cyanopicolinic acid. LC-MS (IE, m/z): 419.

EXAMPLE 34

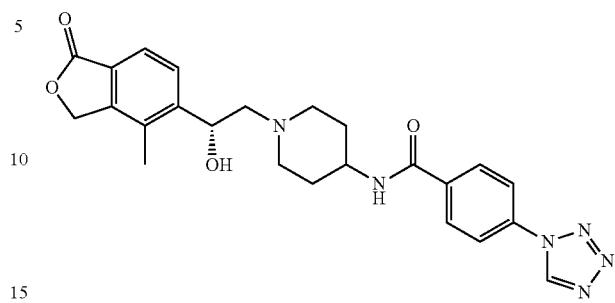

(R)-N-(1-(2-Hydroxy-2-(4-methyl-1-oxo-1,3-dihydroisobenzofuran-5-yl)ethyl)piperidin-4-yl)-4-(1H-tetrazol-1-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 4-(1H-tetrazol-1-yl)benzoic acid. LC-MS (IE, m/z): 463.

EXAMPLE 35

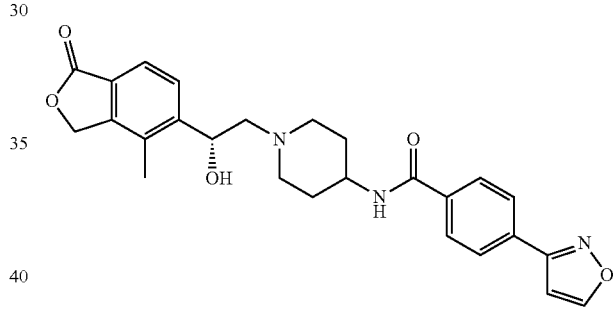

(R)-N-(1-(2-Hydroxy-2-(4-methyl-1-oxo-1,3-dihydroisobenzofuran-5-yl)ethyl)piperidin-4-yl)-4-(isoxazol-3-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 4-(isoxazol-3-yl)benzoic acid. LC-MS (IE, m/z): 462.

EXAMPLE 36

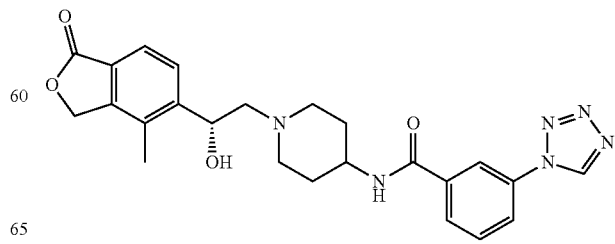

(R)-N-(1-(2-Hydroxy-2-(4-methyl-1-oxo-1,3-dihydroisobenzofuran-5-yl)ethyl)piperidin-4-yl)-3-(1H-tetrazol-1-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 3-(1H-tetrazol-1-yl)benzoic acid. LC-MS (IE, m/z): 463.

EXAMPLE 37

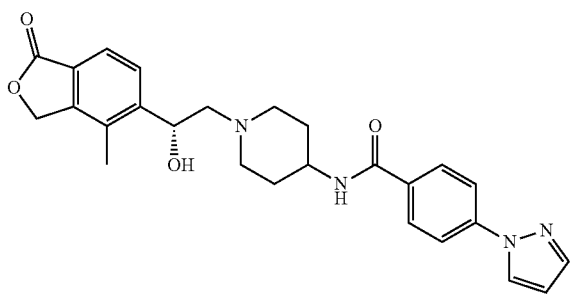 [SMILES: Cc1c([C@@H](O)CN2CCC(NC(=O)c3ccc(-n4cccn4)cc3)CC2)ccc2c1COC2=O]

(R)-N-(1-(2-Hydroxy-2-(4-methyl-1-oxo-1,3-dihydroisobenzofuran-5-yl)ethyl)piperidin-4-yl)-4-(1H-pyrazol-1-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 4-(1H-pyrazol-1-yl)benzoic acid. LC-MS (IE, m/z): 462.

EXAMPLE 38

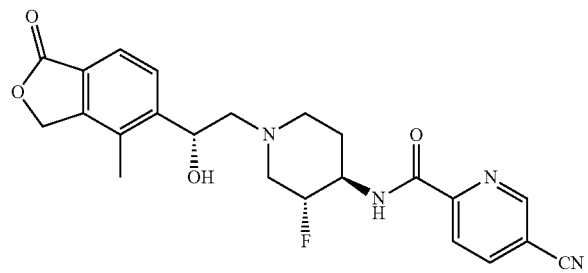 [SMILES: Cc1c([C@@H](O)CN2CC[C@@H](NC(=O)c3ccc(C#N)cn3)[C@H](F)C2)ccc2c1COC2=O]

5-Cyano-N-((trans)-3-fluoro-1-((R)-2-hydroxy-2-(4-methyl-1-oxo-1,3-dihydroisobenzofuran-5-yl)ethyl)piperidin-4-yl)picolinamide The title compound was prepared in a similar fashion to that described for the synthesis of EXAMPLE 8 starting from 5-((R)-2-((trans)-4-amino-3-fluoropiperidin-1-yl)-1-hydroxyethyl)-4-methylisobenzofuran-1(3H)-one hydrochloride and 5-cyanopicolinic acid. LC-MS (IE, m/z): 439.

EXAMPLE 39

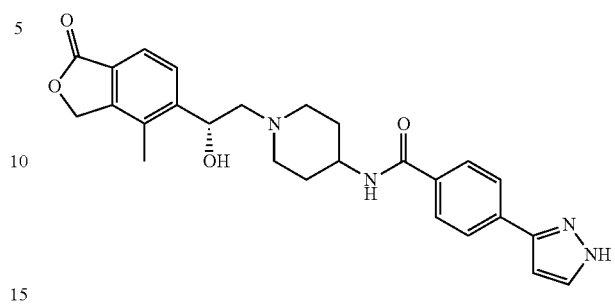

(R)-N-(1-(2-Hydroxy-2-(4-methyl-1-oxo-1,3-dihydroisobenzofuran-5-yl)ethyl)piperidin-4-yl)-4-(1H-pyrazol-3-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 4-(1H-pyrazol-3-yl)benzoic acid. LC-MS (IE, m/z): 462.

EXAMPLE 40

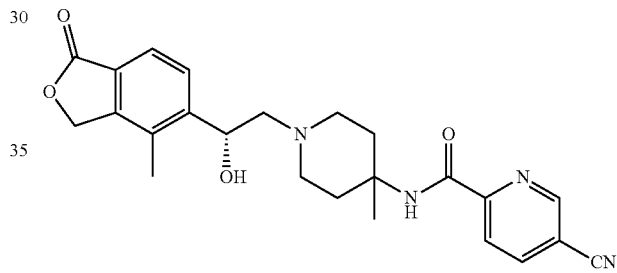

(R)-5-Cyano-N-(1-(2-hydroxy-2-(4-methyl-1-oxo-1,3-dihydroisobenzofuran-5-yl)ethyl)-4-methylpiperidin-4-yl)picolinamide The title compound was prepared in a similar fashion to that described for the synthesis of EXAMPLE 8 starting from (R)-5-(2-(4-amino-4-methylpiperidin-1-yl)-1-hydroxyethyl)-4-methylisobenzofuran-1(3H)-one hydrochloride and 5-cyanopicolinic acid.
LC-MS (IE, m/z): 435.

EXAMPLE 41

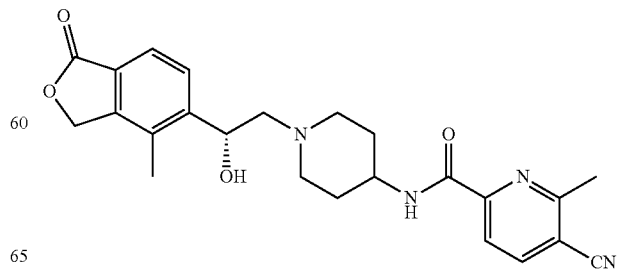

(R)-5-Cyano-N-(1-(2-hydroxy-2-(4-methyl-1-oxo-1,3-dihydroisobenzofuran-5-yl)ethyl)piperidin-4-yl)-6-methylpicolinamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 5-cyano-6-methylpicolinic acid. LC-MS (IE, m/z): 435.

EXAMPLE 42

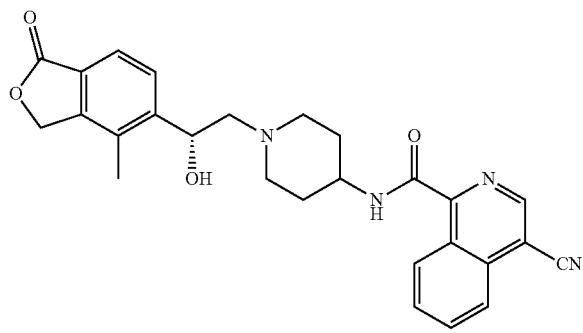 [SMILES: Cc1c([C@@H](O)CN2CCC(NC(=O)c3ncc(C#N)c4ccccc34)CC2)ccc2c1COC2=O]

(R)-4-Cyano-N-(1-(2-hydroxy-2-(4-methyl-1-oxo-1,3-dihydroisobenzofuran-5-yl)ethyl)piperidin-4-yl)isoquinoline-1-carboxamide The title compound (R)-4-cyano-N-(1-(2-hydroxy-2-(4-methyl-1-oxo-1,3-dihydroisobenzofuran-5-yl)ethyl)piperidin-4-yl)isoquinoline-1-carboxamide was prepared in a similar fashion to that described for the synthesis of EXAMPLE 6 starting from 4-cyano-N-(piperidin-4-yl)isoquinoline-1-carboxamide hyrdochloride and (R)-4-methyl-5-oxiran-2-yl-2-benzofuran-1(3H)-one. LC-MS (IE, m/z): 471.

EXAMPLE 43 A AND B

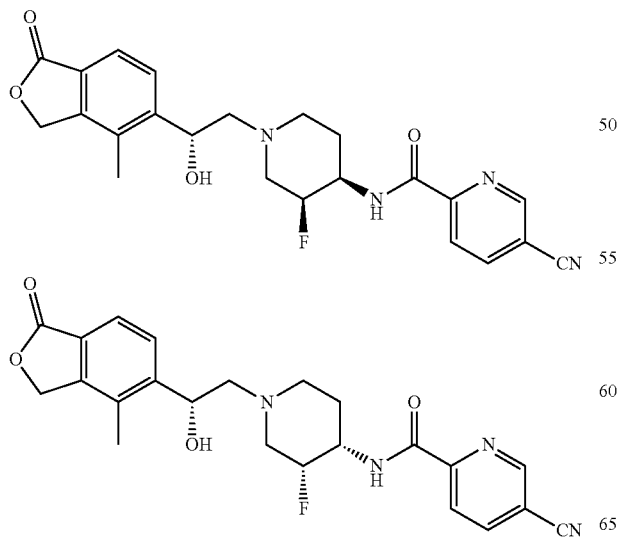

5-Cyano-N-((cis)-3-fluoro-1-((R)-2-hydroxy-2-(4-methyl-1-oxo-1,3-dihydroisobenzofuran-5-yl)ethyl)piperidin-4-yl)picolinamide To a solution of 5-((R)-2-((cis)-4-Amino-3-fluoropiperidin-1-yl)-1-hydroxyethyl)-4-methylisobenzofuran-1(3H)-one hydrochloride (600 mg, 1.6 mmol), commercially available 5-cyano-2-pyridine carboxylic acid (230 mg, 1.6 mmol), and TBTU (610 mg, 1.9 mmol) in DMF (8 mL) was added triethylamine (0.55 ml, 3.9 mmol) at room temperature and the reaction mixture was stirred overnight. The mixture was partitioned between EtOAc and saturated aq NaHCO$_3$, the layers separated, and the aqueous layer extracted with EtOAc (twice). The combined organic phase was washed with brine, dried over anhydrous MgSO$_4$, filtered and concentrated in vacuo. Purification by Mass-directed HPLC provided two diastereomers of 5-cyano-N-((cis)-3-fluoro-1-((R)-2-hydroxy-2-(4-methyl-1-oxo-1,3-dihydroisobenzofuran-5-yl)ethyl)piperidin-4-yl)picolinamide:

Isomer A: $^1$H NMR (500 MHz; CD$_3$OD): 9.02 (s, 1H), 8.41 (m, 1H), 8.28 (m, 1H), 7.88 (m, 1H), 7.79 (m, 2H), 5.55 (m, 1H), 5.40 (s, 2H), 5.22 (m, 1H), 4.52 (m, 2H), 4.23 (m, 1H), 3.71 (m, 2H), 3.38 (m, 2H), 2.45 (m, 1H), 2.41 (s, 3H), 2.18 (m, 1H); LC-MS (IE, m/z): 439.

Isomer B: $^1$H NMR (500 MHz; CD$_3$OD): 9.01 (s, 1H), 8.39 (m, 1H), 8.29 (m, 1H), 7.86 (m, 1H), 7.79 (m, 2H), 5.59 (m, 1H), 5.40 (s, 2H), 5.20 (m, 1H), 4.51 (m, 2H), 4.35 (m, 1H), 3.72 (m, 4H), 2.46 (m, 1H), 2.42 (s, 3H), 2.21 (m, 1H); LC-MS (IE, m/z): 439.

EXAMPLE 44 A AND B

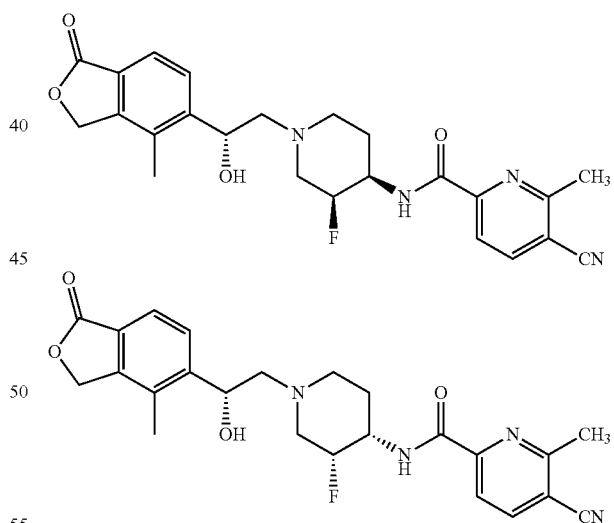

5-Cyano-N-((cis)-3-fluoro-1-((R)-2-hydroxy-2-(4-methyl-1-oxo-1,3-dihydroisobenzofuran-5-yl)ethyl)piperidin-4-yl)-6-methylpicolinamide The individual diastereomers of the title compound were prepared in a similar fashion to that described for the synthesis of EXAMPLE 43 A and B starting from 5-((R)-2-((cis)-4-amino-3-fluoropiperidin-1-yl)-1-hydroxyethyl)-4-methylisobenzofuran-1(3H)-one hydrochloride and 5-cyano-6-methylpicolinic acid including purification under mass directed HPLC conditions. Isomer A: LC-MS (IE, m/z): 453. Isomer B: LC-MS (IE, m/z): 453.

EXAMPLE 45

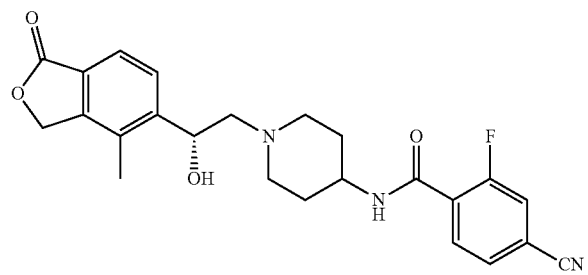 [SMILES: Cc1c([C@@H](O)CN2CCC(NC(=O)c3ccc(C#N)cc3F)CC2)ccc2c1COC2=O]

(R)-4-Cyano-2-fluoro-N-(1-(2-hydroxy-2-(4-methyl-1-oxo-1,3-dihydroisobenzofuran-5-yl)ethyl)piperidin-4-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 4-cyano-2-fluorobenzoic acid. LC-MS (IE, m/z): 438.

EXAMPLE 46 A AND B

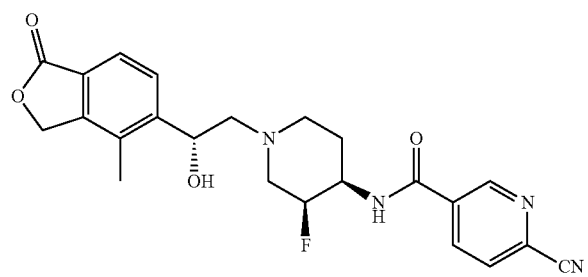

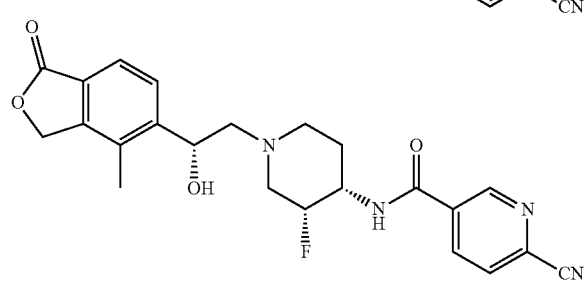

6-Cyano-N-((cis)-3-fluoro-14(R)-2-hydroxy-2-(4-methyl-1-oxo-1,3-dihydroisobenzofuran-5-yl)ethyl)piperidin-4-yl)nicotinamide The individual diastereomers of 6-cyano-N-((cis)-3-fluoro-1-((R)-2-hydroxy-2-(4-methyl-1-oxo-1,3-dihydroisobenzofuran-5-yl)ethyl)piperidin-4-yl)nicotinamide were prepared in a similar fashion to that described for the synthesis of EXAMPLE 43 A and B starting from 5-((R)-2-((cis)-4-amino-3-fluoropiperidin-1-yl)-1-hydroxyethyl)-4-methylisobenzofuran-1(3H)-one hydrochloride and 6-cyanonicotinic acid including purification under mass directed HPLC conditions. Isomer A: LC-MS (IE, m/z): 439. Isomer B: LC-MS (IE, m/z): 439.

EXAMPLE 47 A AND B

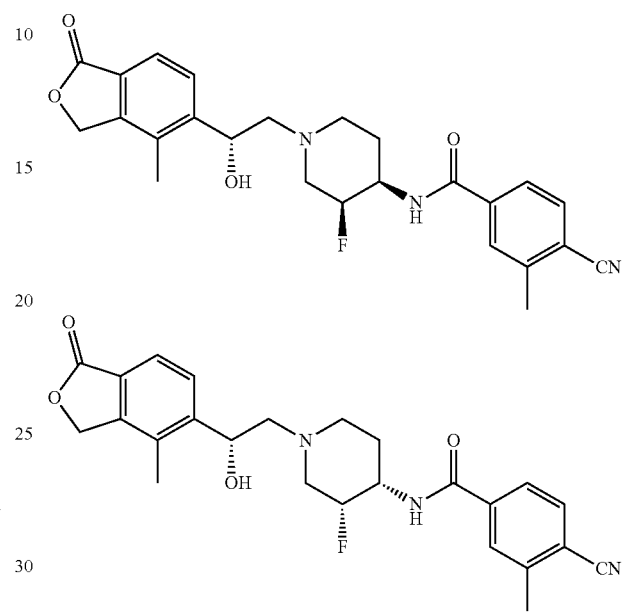

4-Cyano-N-((cis)-3-fluoro-1-((R)-2-hydroxy-2-(4-methyl-1-oxo-1,3-dihydroisobenzofuran-5-yl)ethyl)piperidin-4-yl)-3-methylbenzamide The individual diastereomers of 4-cyano-N-((cis)-3-fluoro-1-((R)-2-hydroxy-2-(4-methyl-1-oxo-1,3-dihydroisobenzofuran-5-yl)ethyl)piperidin-4-yl)-3-methylbenzamide were prepared in a similar fashion to that described for the synthesis of EXAMPLE 43 A and B starting from 5-((R)-2-((cis)-4-amino-3-fluoropiperidin-1-yl)-1-hydroxyethyl)-4-methylisobenzofuran-1(3H)-one hydrochloride and 4-cyano-3-methylbenzoic acid including purification under mass directed HPLC conditions. Isomer A: LC-MS (IE, m/z): 452. Isomer B: LC-MS (IE, m/z): 452.

EXAMPLE 48 A AND B

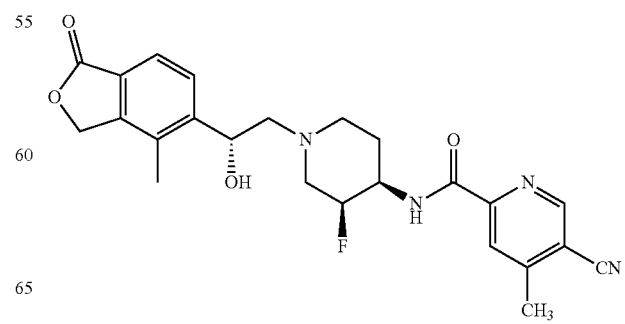

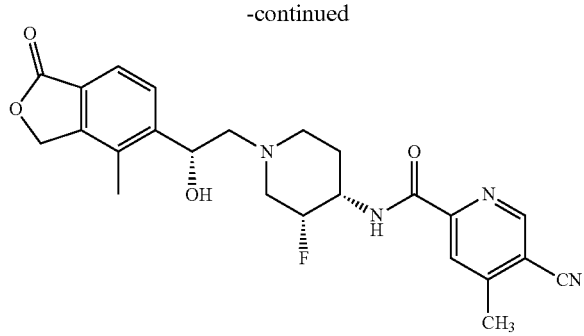

5-Cyano-N-acis)-3-fluoro-1-((R)-2-hydroxy-2-(4-methyl-1-oxo-1,3-dihydroisobenzofuran-5-yl)ethyl)piperidin-4-yl)-4-methylpicolinamide The individual diastereomers of 5-Cyano-N -((cis)-3-fluoro-1-((R)-2-hydroxy-2-(4-methyl-1-oxo-1,3-dihydroisobenzofuran-5-yl)ethyl)piperidin-4-yl)-4-methylpicolinamide were prepared in a similar fashion to that described for the synthesis of EXAMPLE 43 A and B starting from 5-((R)-2-((cis)-4-amino-3-fluoropiperidin-1-yl)-1-hydroxyethyl)-4-methylisobenzofuran-1(3H)-one hydrochloride and 5-cyano-4-methylpicolinic acid including purification under mass directed HPLC conditions.

Isomer A: LC-MS (IE, m/z): 453. Isomer B: LC-MS (IE, m/z): 453.

EXAMPLE 49

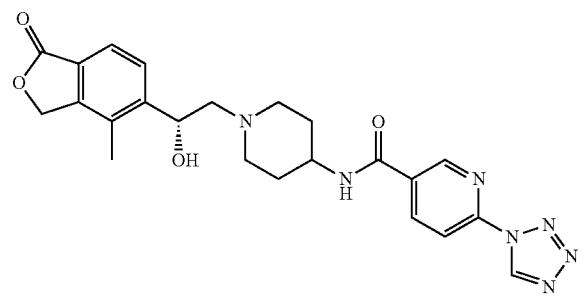 [SMILES: Cc1c([C@@H](O)CN2CCC(NC(=O)c3ccc(-n4cnnn4)nc3)CC2)ccc2c1COC2=O]

(R)-N-(1-(2-Hydroxy-2-(4-methyl-1-oxo-1,3-dihydroisobenzofuran-5-yl)ethyl)piperidin-4-yl)-6-(1H-tetrazol-1-yl)nicotinamide (R)-5-Cyano-N-(1-(2-hydroxy-2-(4-methyl-1-oxo-1,3-dihydroisobenzofuran-5-yl)ethyl)piperidin-4-yl)-6-methylpicolinamide was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 6-(1H-tetrazol-1-yl)nicotinic acid. $^1$H NMR (500 MHz; CD$_3$OD): 9.98 (s, 1H), 9.03 (s, 1H), 8.52 (m, 1H), 8.21 (m, 1H), 7.83 (m, 1H), 7.77 (m, 2H), 5.39 (s, 2H), 5.26 (m, 1H), 4.02 (m, 1H), 2.80 (m, 2H), 2.39 (m, 4H), 2.18 (s, 3H), 1.41 (m, 2H); LC-MS (IE, m/z): 464.

EXAMPLE 50 A AND B

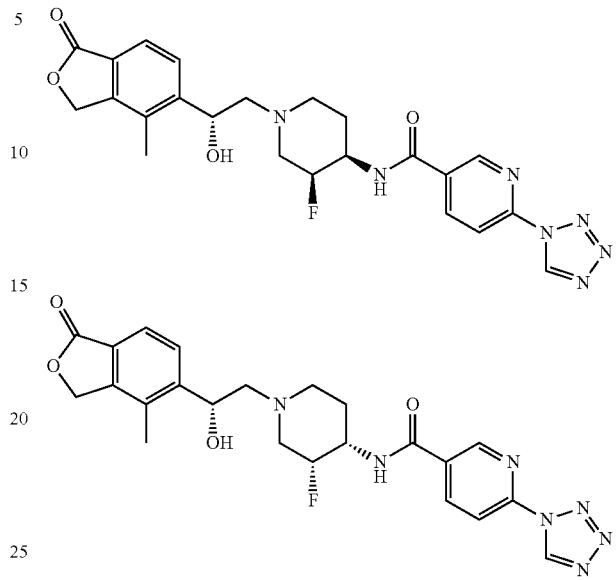

N-((cis)-3-Fluoro-1-((R)-2-hydroxy-2-(4-methyl-1-oxo-1,3-dihydroisobenzofuran-5-yl)ethyl)piperidin-4-yl)-6-(1H-tetrazol-1-yl)nicotinamide The individual diastereomers of N -((cis)-3-Fluoro-1-((R)-2-hydroxy-2-(4-methyl-1-oxo-1,3-dihydroisobenzofuran-5-yl)ethyl)piperidin-4-yl)-6-(1H-tetrazol-1-yl)nicotinamide were prepared in a similar fashion to that described for the synthesis of EXAMPLE 43 A and B starting from 5-((R)-2-((cis)-4-amino-3-fluoropiperidin-1-yl)-1-hydroxyethyl)-4-methylisobenzofuran-1(3H)-one hydrochloride and 6-(1H-tetrazol-1-yl)nicotinic acid including purification under mass directed HPLC conditions.

Isomer A: LC-MS (IE, m/z): 482. Isomer B: LC-MS (IE, m/z): 482.

EXAMPLE 51

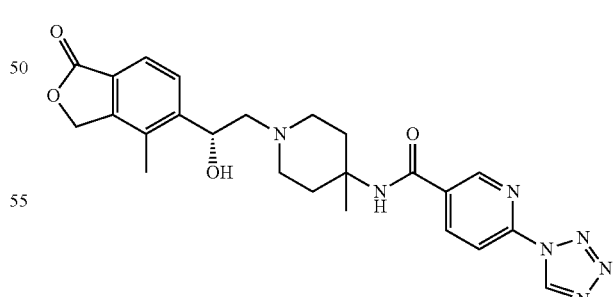

(R)-N-(1-(2-Hydroxy-2-(4-methyl-1-oxo-1,3-dihydroisobenzofuran-5-yl)ethyl)-4-methylpiperidin-4-yl)-6-(1H-tetrazol-1-yl)nicotinamide The title compound was prepared in a similar fashion to that described for the synthesis of EXAMPLE 8 starting from (R)-5-(2-(4-amino-4-methylpiperidin-1-yl)-1-hydroxyethyl)-4-methylisobenzofuran-1(3H)-one hydrochloride and 6-(1H-tetrazol-1-yl)nicotinic acid. $^1$H NMR (500 MHz; CD$_3$OD): 9.99 (s, 1H), 8.99 (s, 1H), 8.49 (m, 1H), 8.181 (m, 1H), 7.78 (m, 1H), 7.66 (m, 2H), 5.41 (m, 1H), 5.38 (s, 2H), 3.21 (m, 2H), 2.97 (m, 2H), 2.59 (M, 2H), 2.32 (s, 3H), 1.93 (m, 2H), 1.58 (s, 3H); LC-MS (IE, m/z): 478.

EXAMPLE 52

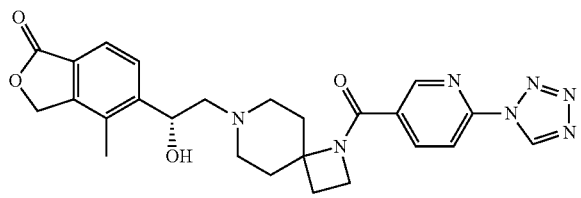 [SMILES: Cc1c([C@@H](O)CN2CCC3(CC2)CCN3C(=O)c2ccc(-n3cnnn3)nc2)ccc2c1COC2=O]

(R)-5-(2-(1-(6-(1H-Tetrazol-1-yl)picolinoyl)-1,7-diazaspiro[3.5]nonan-7-yl)-1-hydroxyethyl)-4-methylisobenzofuran-1(3H)-one The title compound was prepared in a similar fashion to that described for the synthesis of EXAMPLE 8 starting from (R)-5-(1-hydroxy-2-(1,7-diazaspiro[3.5]nonan-7-yl)ethyl)-4-methylisobenzofuran-1(3H)-one hydrochloride and 6-(1H-tetrazol-1-yl)nicotinic acid. LC-MS (IE, m/z): 490.

EXAMPLE 53

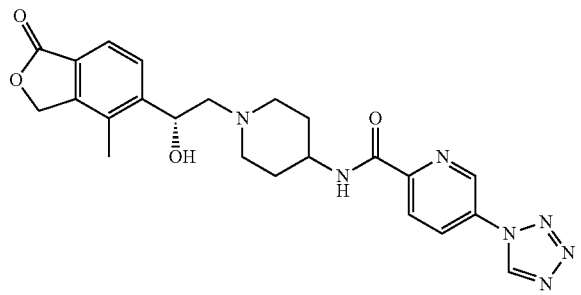 [SMILES: Cc1c([C@@H](O)CN2CCC(NC(=O)c3ccc(-n4cnnn4)cn3)CC2)ccc2c1COC2=O]

(R)-N-(1-(2-Hydroxy-2-(4-methyl-1-oxo-1,3-dihydroisobenzofuran-5-yl)ethyl)piperidin-4-yl)-5-(1H-tetrazol-1-yl)picolinamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 5-(1H-tetrazol-1-yl)nicotinic acid. LC-MS (IE, m/z): 464.

EXAMPLE 54 A AND B

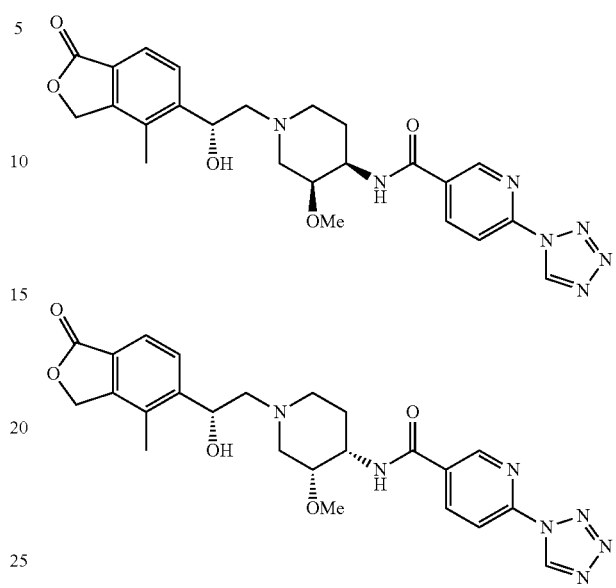

N-((cis)-1-((R)-2-Hydroxy-2-(4-methyl-1-oxo-1,3-dihydroisobenzofuran-5-yl)ethyl)-3-methoxypiperidin-4-yl)-6-(1H-tetrazol-1-yl)nicotinamide To a mixture of N-((cis)-3-methoxypiperidin-4-yl)-6-(1H-tetrazol-1-yl)picolinamide (60 mg, 0.20 mmol) in ethanol (1 mL) was added (R)-4-methyl-5-oxiran-2-yl-2-benzofuran-1(3H)-one (38 mg, 0.20 mmol) at room temperature. The mixture was heated in a microwave reactor at 140° C. for 30 min. The resulting mixture was concentrated in vacuo and the residue was purified by prep TLC (silica gel; 10% MeOH/DCM) to provide the title compound. Resolution of the diastereomers was carried out (prep SFC, 50 mL/min., 20% MeOH+0.2% DEA in SC CO$_2$, OJ 21×250 mm) to provide: Isomer A: $^1$H NMR (500 MHz; CD$_3$OD): 10.00 (s, 1H), 9.02 (s, 1H), 8.51 (m, 1H), 8.21 (m, 1H), 7.80 (d, J=7.5 Hz, 1H), 7.73 (d, J=7.5 Hz, 1H), 5.38 (s, 2H), 5.24 (m, 1H), 4.17 (m, 1H), 3.65 (m, 1H), 3.42 (s, 3H), 3.38 (m, 1H), 2.98 (m, 1H), 2.79 (m, 1H), 2.58 (m, 3H), 2.37 (s, 3H), 2.16 (m, 1H), 1.78 (m, 1H); LC-MS (IE, m/z): 494.

Isomer B: $^1$H NMR (500 MHz; CD$_3$OD): 10.01 (s, 1H), 9.01 (s, 1H), 8.53 (m, 1H), 8.22 (m, 1H), 7.79 (d, J=7.5 Hz, 1H), 7.72 (d, J=7.5 Hz, 1H), 5.38 (s, 2H), 5.26 (m, 1H), 4.17 (m, 1H), 3.65 (m, 1H), 3.49 (s, 3H), 3.15 (m, 1H), 2.85 (m, 1H), 2.57 (m, 2H), 2.44 (m, 1H), 2.38 (s, 3H), 2.12 (m, 1H), 1.79 (m, 1H); LC-MS (IE, m/z): 494.

EXAMPLE 55

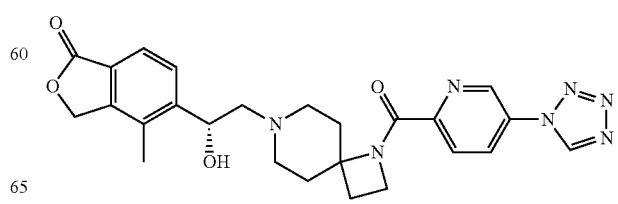

(R)-5-(2-(1-(5-(1H-Tetrazol-1-yl)picolinoyl)-1,7-diazaspiro[3.5]nonan-7-yl)-1-hydroxyethyl)-4-methylisobenzofuran-1(3H)-one The title compound was prepared in a similar fashion to that described for the synthesis of EXAMPLE 8 starting from (R)-5-(1-hydroxy-2-(1,7-diazaspiro[3.5]nonan-7-yl)ethyl)-4-methylisobenzofuran-1(3H)-one hydrochloride and 5-(1H-tetrazol-1-yl)nicotinic acid. LC-MS (IE, m/z): 490.

EXAMPLE 56

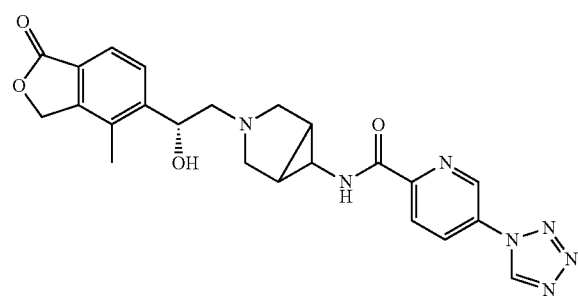 [SMILES: Cc1c([C@@H](O)CN2CC3C(C2)C3NC(=O)c2ccc(-n3cnnn3)cn2)ccc2c1COC2=O]

N-(3-((R)-2-Hydroxy-2-(4-methyl-1-oxo-1,3-dihydroisobenzofuran-5-yl)ethyl)-3-azabicyclo[3.1.0]hexan-6-yl)-5-(1H-tetrazol-1-yl)picolinamide N-(3-((R)-2-Hydroxy-2-(4-methyl-1-oxo-1,3-dihydroisobenzofuran-5-yl)ethyl)-3-azabicyclo[3.1.0]hexan-6-yl)-5-(1H-tetrazol-1-yl)picolinamide was prepared in a similar fashion to that described for the synthesis of EXAMPLE 8 starting from 5-((1R)-2-(6-amino-3-azabicyclo[3.1.0]hexan-3-yl)-1-hydroxyethyl)-4-methylisobenzofuran-1(3H)-one hydrochloride and 5-(1H-tetrazol-1-yl)nicotinic acid. LC-MS (IE, m/z): 462.

EXAMPLE 57

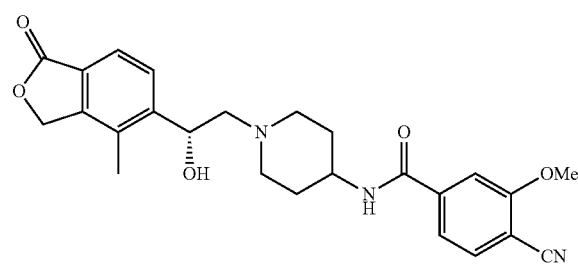 [SMILES: COc1cc(C(=O)NC2CCN(C[C@H](O)c3ccc4c(c3C)COC4=O)CC2)ccc1C#N]

(R)-4-Cyano-N-(1-(2-hydroxy-2-(4-methyl-1-oxo-1,3-dihydroisobenzofuran-5-yl)ethyl)piperidin-4-yl)-3-methoxybenzamide The title compound was prepared in a similar fashion to that described for the synthesis of EXAMPLE 6 starting from (4-cyano-3-methoxy-N-(piperidin-4-yl)benzamide hydrochloride and (R)-4-methyl-5-oxiran-2-yl-2-benzofuran-1(3H)-one.
LC-MS (IE, m/z): 450.

EXAMPLE 58 A AND B

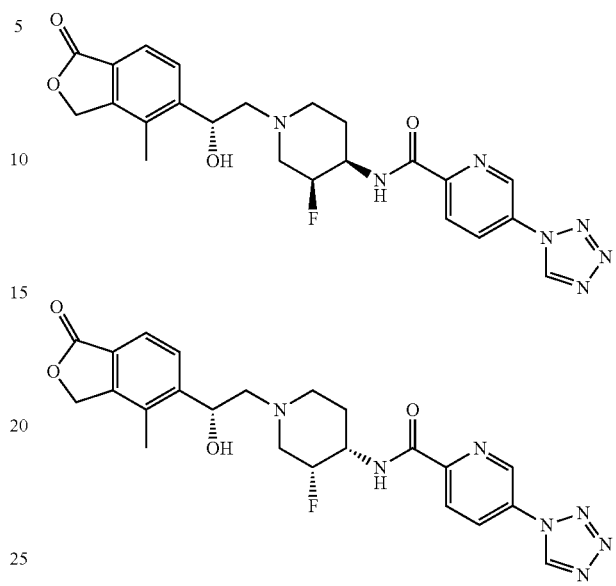

N-((cis)-3-fluoro-1-((R)-2-hydroxy-2-(4-methyl-1-oxo-1,3-dihydroisobenzofuran-5-yl)ethyl)piperidin-4-yl)-5-(1H-tetrazol-1-yl)picolinamide The individual diastereomers of N -((cis)-3-Fluoro-1-((R)-2-hydroxy-2-(4-methyl-1-oxo-1,3-dihydroisobenzofuran-5-yl)ethyl)piperidin-4-yl)-5-(1H-tetrazol-1-yl)nicotinamide were prepared in a similar fashion to that described for the synthesis of EXAMPLE 43 A and B starting from 5-((R)-2-((cis)-4-amino-3-fluoropiperidin-1-yl)-1-hydroxyethyl)-4-methylisobenzofuran-1(3H)-one hydrochloride and 5-(1H-tetrazol-1-yl)nicotinic acid including purification under mass directed HPLC conditions.
Isomer A: LC-MS (IE, m/z): 482. Isomer B: LC-MS (IE, m/z): 482.

EXAMPLE 59

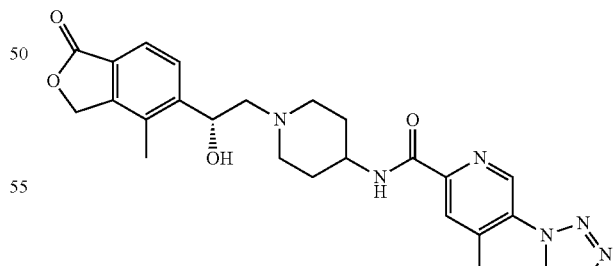

(R)-N-(1-(2-Hydroxy-2-(4-methyl-1-oxo-1,3-dihydroisobenzofuran-5-yl)ethyl)piperidin-4-yl)-4-methyl-5-(1H-tetrazol-1-yl)picolinamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1 (3H)-one hydrochloride and 4-methyl-5-(1H-tetrazol-1-yl)picolinic acid. LC-MS (IE, m/z): 478.

EXAMPLE 60

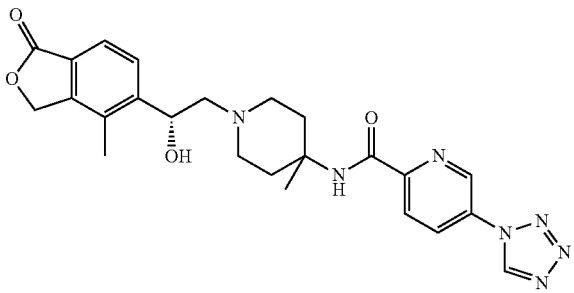 [SMILES: Cc1c([C@@H](O)CN2CCC(C)(NC(=O)c3ccc(-n4cnnn4)cn3)CC2)ccc2c1COC2=O]

(R)-N-(1-(2-Hydroxy-2-(4-methyl-1-oxo-1,3-dihydroisobenzofuran-5-yl)ethyl)-4-methylpiperidin-4-yl)-5-(1H-tetrazol-1-yl)picolinamide The title compound was prepared in a similar fashion to that described for the synthesis of EXAMPLE 8 starting from (R)-5-(2-(4-amino-4-methylpiperidin-1-yl)-1-hydroxyethyl)-4-methylisobenzofuran-1(3H)-one hydrochloride and 5-(1H-tetrazol-1-yl)nicotinic acid. LC-MS (IE, m/z): 478.

EXAMPLE 61

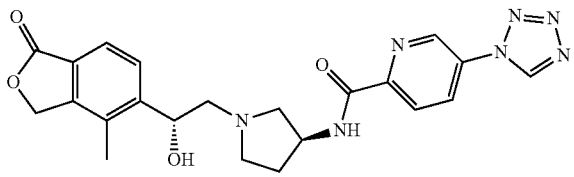 [SMILES: Cc1c([C@@H](O)CN2CC[C@H](NC(=O)c3ccc(-n4cnnn4)cn3)C2)ccc2c1COC2=O]

N-((S)-1-((R)-2-Hydroxy-2-(4-methyl-1-oxo-1,3-dihydroisobenzofuran-5-yl)ethyl)pyrrolidin-3-yl)-5-(1H-tetrazol-1-yl)picolinamide The title compound was prepared in a similar fashion to that described for the synthesis of EXAMPLE 8 starting from 5-((R)-2-((S)-3-aminopyrrolidin-1-yl)-1-hydroxyethyl)-4-methylisobenzofuran-1(3H)-one hydrochloride (Intermediate 34) and 5-(1H-tetrazol-1-yl)nicotinic acid. LC-MS (IE, m/z): 450.

EXAMPLE 62

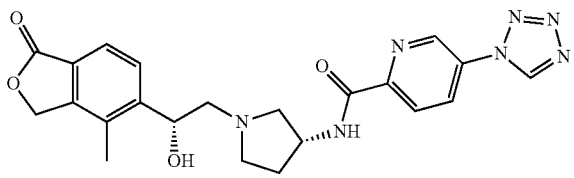 [SMILES: Cc1c([C@@H](O)CN2CC[C@@H](NC(=O)c3ccc(-n4cnnn4)cn3)C2)ccc2c1COC2=O]

N-((R)-1-((R)-2-Hydroxy-2-(4-methyl-1-oxo-1,3-dihydroisobenzofuran-5-yl)ethyl)pyrrolidin-3-yl)-5-(1H-tetrazol-1-yl)picolinamide The title compound was prepared in a similar fashion to that described for the synthesis of EXAMPLE 8 starting from 5-((R)-2-((R)-3-aminopyrrolidin-1-yl)-1-hydroxyethyl)-4-methylisobenzofuran-1(3H)-one hydrochloride (Intermediate 35) and 5-(1H-tetrazol-1-yl)nicotinic acid. LC-MS (IE, m/z): 450.

EXAMPLE 63

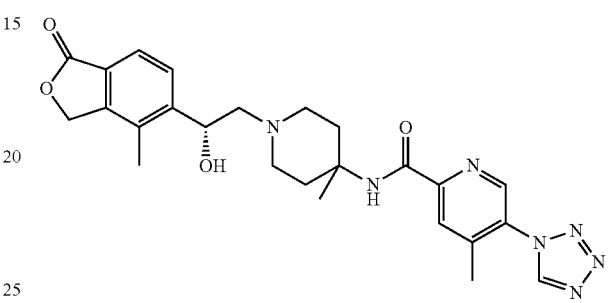

(R)-N-(1-(2-Hydroxy-2-(4-methyl-1-oxo-1,3-dihydroisobenzofuran-5-yl)ethyl)-4-methylpiperidin-4-yl)-4-methyl-5-(1H-tetrazol-1-yl)picolinamide The title compound was prepared in a similar fashion to that described for the synthesis of EXAMPLE 8 starting from (R)-5-(2-(4-amino-4-methylpiperidin-1-yl)-1-hydroxyethyl)-4-methylisobenzofuran-1(3H)-one hydrochloride and 4-methyl-5-(1H-tetrazol-1-yl)picolinic acid. LC-MS (IE, m/z): 492.

EXAMPLE 64

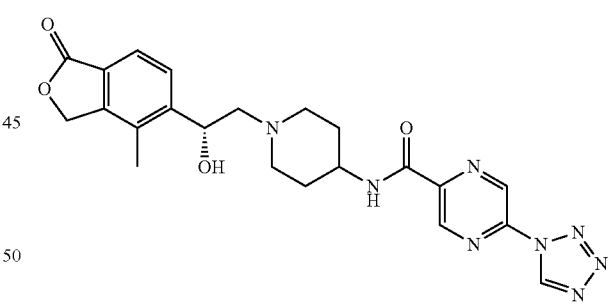

(R)-N-(1-(2-Hydroxy-2-(4-methyl-1-oxo-1,3-dihydroisobenzofuran-5-yl)ethyl)piperidin-4-yl)-5-(1H-tetrazol-1-yl)pyrazine-2-carboxamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 5-(1H-tetrazol-1-yl)pyrazine-2-carboxylic acid.
$^1$H NMR (500 MHz; CDCl$_3$): 9.64 (s, 1H), 9.42 (s, 1H), 9.39 (s, 1H), 7.79 (m, 1H), 7.72 (m, 1H), 5.28 (s, 2H), 5.19 (m, 1H), 4.16 (m, 1H), 3.97 (m, 1H), 3.27 (m, 1H), 2.90 (m, 2H), 2.63 (m, 2H), 2.48 (m, 2H), 2.31 (s, 3H), 2.18 (m, 1H), 1.82 (m, 1H); LC-MS (IE, m/z): 465.

EXAMPLE 65

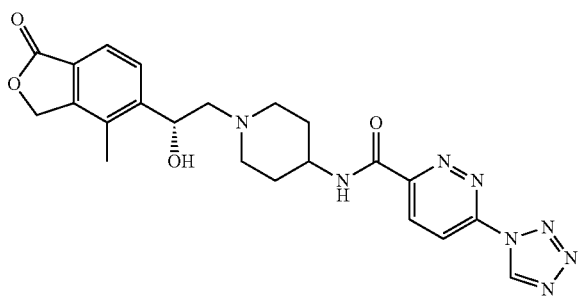

(R)-N-(1-(2-Hydroxy-2-(4-methyl-1-oxo-1,3-dihydroisobenzofuran-5-yl)ethyl)piperidin-4-yl)-6-(1H-tetrazol-1-yl)pyridazine-3-carboxamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 6-(1H-tetrazol-1-yl)pyridazine-3-carboxylic acid.
$^1$H NMR (500 MHz; CDCl$_3$): 9.82 (s, 1H), 8.68 (m, 1H), 8.52 (m, 1H), 8.02 (m, 1H), 7.76 (m, 1H), 5.31 (s, 2H), 5.18 (m, 1H), 4.18 (m, 1H), 4.03 (m, 1H), 3.24 (m, 1H), 2.92 (m, 2H), 2.63 (m, 2H), 2.48 (m, 2H), 2.31 (s, 3H), 2.18 (m, 1H), 1.82 (m, 1H); LC-MS (IE, m/z): 465.

EXAMPLE 66

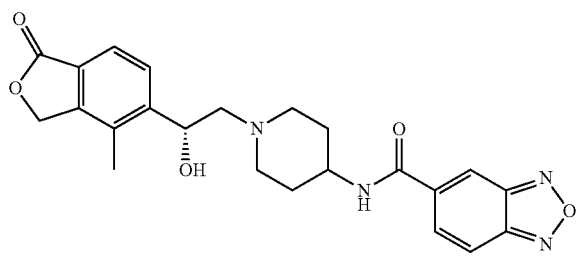 [SMILES: Cc1c([C@@H](O)CN2CCC(NC(=O)c3ccc4nonc4c3)CC2)ccc2c1COC2=O]

(R)-N-(1-(2-Hydroxy-2-(4-methyl-1-oxo-1,3-dihydroisobenzofuran-5-yl)ethyl)piperidin-4-yl)benzo[c][1,2,5]oxadiazole-5-carboxamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and benzo[c][1,2,5]oxadiazole-5-carboxylic acid. LC-MS (IE, m/z): 437.

EXAMPLE 67

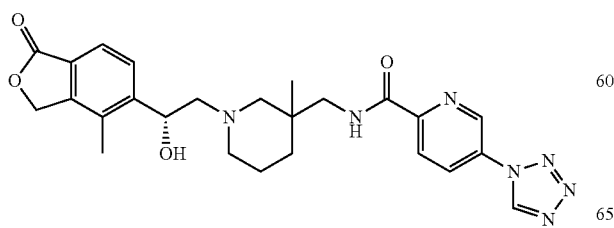

N-((1-((R)-2-Hydroxy-2-(4-methyl-1-oxo-1,3-dihydroisobenzofuran-5-yl)ethyl)-3-methylpiperidin-3-yl)methyl)-5-(1H-tetrazol-1-yl)picolinamide The title compound was prepared in a similar fashion to that described for the synthesis of EXAMPLE 8 starting from 5-((1R)-2-(3-(aminomethyl)-3-methylpiperidin-1-yl)-1-hydroxyethyl)-4-methylisobenzofuran-1(3H)-one hydrochloride and 5-(1H-tetrazol-1-yl)nicotinic acid. LC-MS (IE, m/z): 492.

EXAMPLE 68

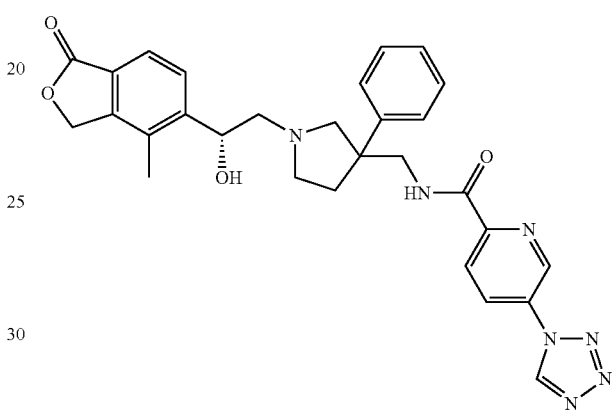

N-((1-((R)-2-Hydroxy-2-(4-methyl-1-oxo-1,3-dihydroisobenzofuran-5-yl)ethyl)-3-phenylpyrrolidin-3-yl)methyl)-5-(1H-tetrazol-1-yl)picolinamide The title compound was prepared in a similar fashion to that described for the synthesis of EXAMPLE 8 starting from 5-((1R)-2-(3-(aminomethyl)-3-phenylpyrrolidin-1-yl)-1-hydroxyethyl)-4-methylisobenzofuran-1(3H)-one hydrochloride and 5-(1H-tetrazol-1-yl)nicotinic acid. LC-MS (IE, m/z): 540.

EXAMPLE 69 A AND B

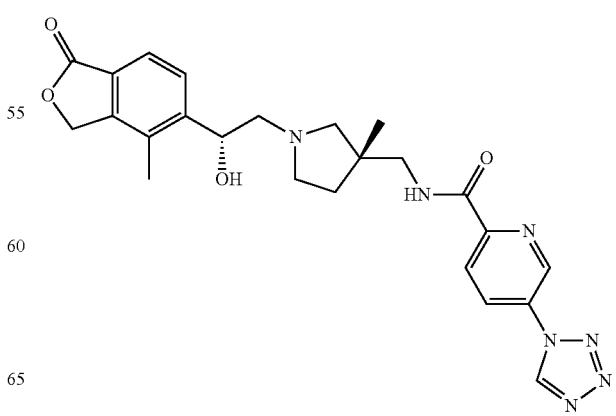

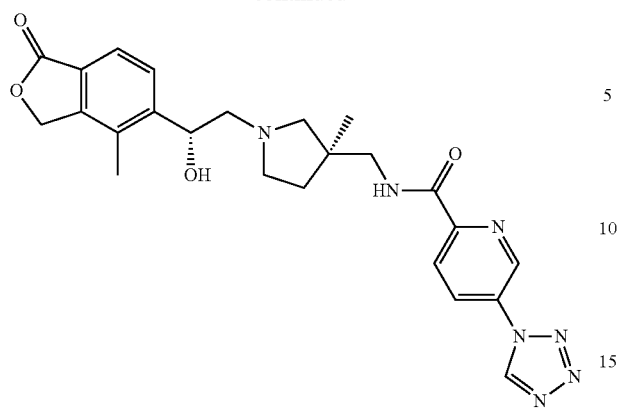

N-((1-((R)-2-Hydroxy-2-(4-methyl-1-oxo-1,3-dihydroisobenzofuran-5-yl)ethyl)-3-methylpyrrolidin-3-yl)methyl)-5-(1H-tetrazol-1-yl)picolinamide The title compound was prepared in a similar fashion to that described for the synthesis of EXAMPLE 8 starting from 5-((1R)-2-(3-(aminomethyl)-3-methylpyrrolidin-1-yl)-1-hydroxyethyl)-4-methylisobenzofuran-1(3H)-one hydrochloride and 5-(1H-tetrazol-1-yl)nicotinic acid. Mass directed preparative HPLC provided for isolation of the individual diastereomers. Isomer A: LC-MS (IE, m/z): 478.

Isomer B: LC-MS (IE, m/z): 478.

EXAMPLE 70

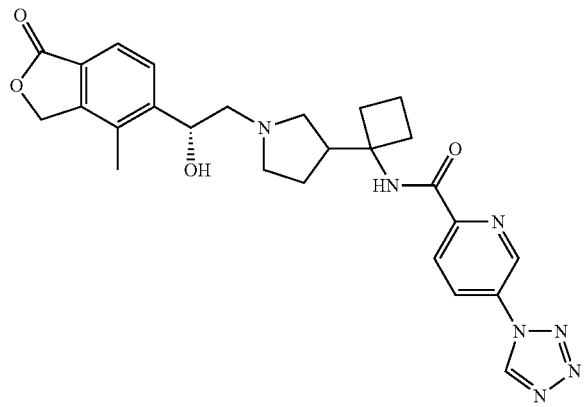 [SMILES: Cc1c([C@@H](O)CN2CCC(C3(NC(=O)c4ccc(-n5cnnn5)cn4)CCC3)C2)ccc2c1COC2=O]

N-(1-(1-((R)-2-Hydroxy-2-(4-methyl-1-oxo-1,3-dihydroisobenzofuran-5-yl)ethyl)pyrrolidin-3-yl)cyclobutyl)-5-(1H-tetrazol-1-yl)picolinamide The title compound was prepared in a similar fashion to that described for the synthesis of EXAMPLE 8 starting from 1-(1-((R)-2-hydroxy-2-(4-methyl-1-oxo-1,3-dihydroisobenzofuran-5-yl)ethyl)pyrrolidin-3-yl)cyclobutanaminium chloride and 5-(1H-tetrazol-1-yl)nicotinic acid. LC-MS (IE, m/z): 504.

EXAMPLE 71

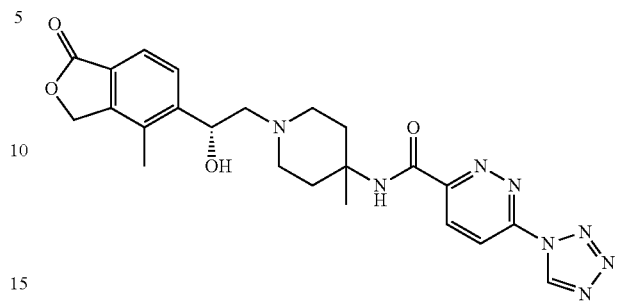

(R)-N-(1-(2-Hydroxy-2-(4-methyl-1-oxo-1,3-dihydroisobenzofuran-5-yl)ethyl)-4-methylpiperidin-4-yl)-6-(1H-tetrazol-1-yl)pyridazine-3-carboxamide (R)-N-(1-(2-Hydroxy-2-(4-methyl-1-oxo-1,3-dihydroisobenzofuran-5-yl)ethyl)-4-methylpiperidin-4-yl)-6-(1H-tetrazol-1-yl)pyridazine-3-carboxamide was prepared in a similar fashion to that described for the synthesis of EXAMPLE 8 starting from (R)-5-(2-(4-amino-4-methylpiperidin-1-yl)-1-hydroxyethyl)-4-methylisobenzofuran-1(3H)-one hydrochloride and 6-(1H-tetrazol-1-yl)pyridazine-3-carboxylic acid. LC-MS (IE, m/z): 479.

EXAMPLE 72

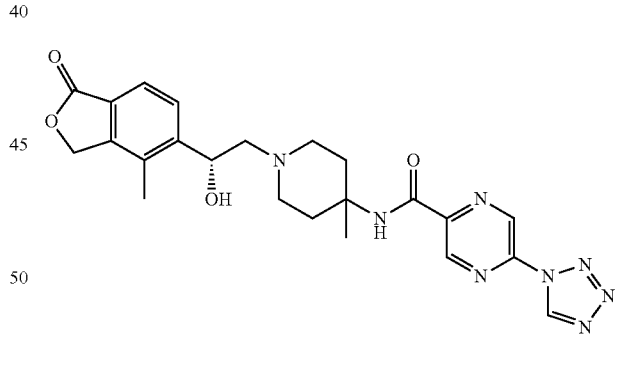

(R)-N-(1-(2-Hydroxy-2-(4-methyl-1-oxo-1,3-dihydroisobenzofuran-5-yl)ethyl)-4-methylpiperidin-4-yl)-5-(1H-tetrazol-1-yl)pyrazine-2-carboxamide The title compound was prepared in a similar fashion to that described for the synthesis of EXAMPLE 8 starting from (R)-5-(2-(4-amino-4-methylpiperidin-1-yl)-1-hydroxyethyl)-4-methylisobenzofuran-1(3H)-one hydrochloride and 5-(1H-tetrazol-1-yl)pyrazine-2-carboxylic acid. LC-MS (IE, m/z): 479.

EXAMPLE 73

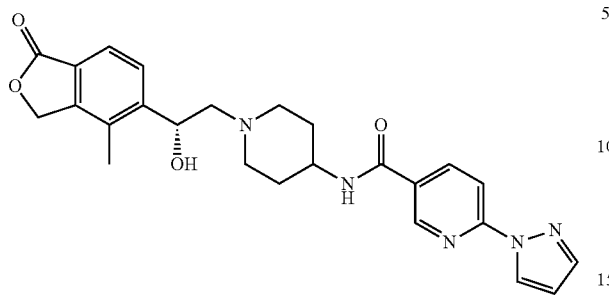

(R)-N-(1-(2-Hydroxy-2-(4-methyl-1-oxo-1,3-dihydroisobenzofuran-5-yl)ethyl)piperidin-4-yl)-6-(1H-pyrazol-1-yl)nicotinamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 6-(1H-pyrazol-1-yl)pyridine-3-carboxylic acid. $^1$H NMR (500 MHz, DMSO-d$_6$): 8.9 (s, 1H), 8.7 (s, 1H), 8.5 (m, 1H), 8.4 (m, 1H), 8.0 (m, 1H), 7.9 (s, 1H), 7.6-7.7 (m, 2H), 6.6 (s, 1H), 5.4 (m, 3H), 5.25 (s, 1H), 5.1 (m, 1H), 4.8 (m, 1H), 3.0 (m, 2H), 2.4 (m, 1H), 2.3-2.4 (m, 4H), 2.1-2.3 (m, 3H), 1.8 (m, 2H), 1.6 (m, 2H); LC-MS (IE, m/z): 462.

EXAMPLE 74

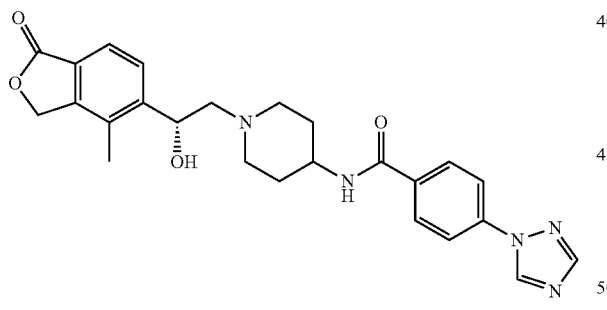

(R)-N-(1-(2-Hydroxy-2-(4-methyl-1-oxo-1,3-dihydroisobenzofuran-5-yl)ethyl)piperidin-4-yl)-4-(1H-1,2,4-triazol-1-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 4-(1H-1,2,4-triazol-1-yl)benzoic acid. $^1$H NMR (500 MHz, DMSO-d$_6$): 9.5 (broad s, 1H), 9.4 (s, 1H), 8.6 (m, 1H), 8.3 (s, 1H), 8.1 (m, 2H), 7.95 (m, 2H), 7.8 (m, 2H), 6.4 (s, 1H), 5.4 (m, 4H), 4.0 (m, 1H), 3.4-3.8 (broad m, 8H), 3.4 (m, 2H), 2.4 (s, 3H); LC-MS (IE, m/z): 462.

EXAMPLE 75

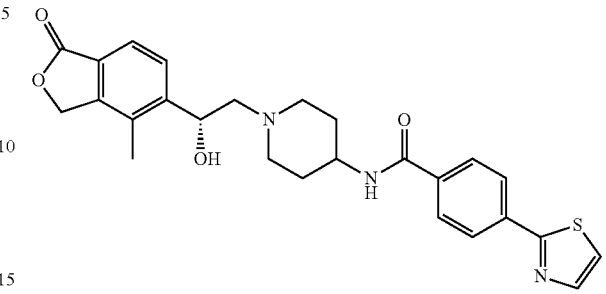

(R)-N-(1-(2-Hydroxy-2-(4-methyl-1-oxo-1,3-dihydroisobenzofuran-5-yl)ethyl)piperidin-4-yl)-4-(thiazol-2-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 4-(thiazol-2-yl)benzoic acid.
$^1$H NMR (500 MHz, CDCl$_3$): 8.1 (m, 2H), 7.9 (s, 1H), 7.8-7.9 (m, 5H), 7.4 (s, 1H), 6.2 (broad m, 1H), 5.2-5.3 (m, 3H), 5.1 (m, 1H), 4.1 (m. 1H), 3.1 (m, 1H), 2.9, (m, 1H), 2.6 (m, 2H), 2.65 (m, 2H), 2.2-2.4 (m, 5H), 2.2 (m, 2H) 1.6-1.8 (m, 2H); LC-MS (IE, m/z): 478.

EXAMPLE 76

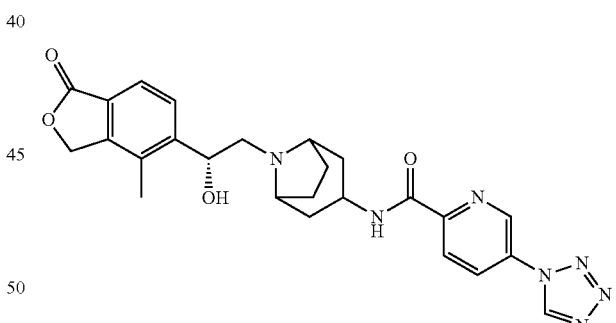

N-(8-((R)-2-Hydroxy-2-(4-methyl-1-oxo-1,3-dihydroisobenzofuran-5-yl)ethyl)-8-azabicyclo[3.2.1]octan-3-yl)-5-(1H-tetrazol-1-yl)picolinamide The title compound was prepared in a similar fashion to that described for the synthesis of EXAMPLE 8 starting from 5-((1R)-2-(3-amino-8-azabicyclo[3.2.1]octan-8-yl)-1-hydroxyethyl)-4-methylisobenzofuran-1(3H)-one hydrochloride and 5-(1H-tetrazol-1-yl)nicotinic acid. LC-MS (IE, m/z): 489.

EXAMPLE 77

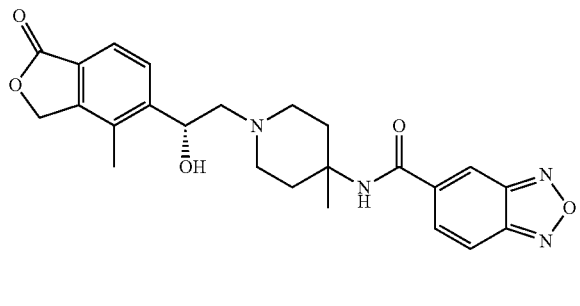

(R)-N-(1-(2-Hydroxy-2-(4-methyl-1-oxo-1,3-dihydroisobenzofuran-5-yl)ethyl)-4-methylpiperidin-4-yl)benzo[c][1,2,5]oxadiazole-5-carboxamide The title compound was prepared in a similar fashion to that described for the synthesis of EXAMPLE 8 starting from (R)-5-(2-(4-amino-4-methylpiperidin-1-yl)-1-hydroxyethyl)-4-methylisobenzofuran-1(3H)-one hydrochloride and benzo[c][1,2,5]oxadiazole-5-carboxylic acid. LC-MS (IE, m/z): 451.

EXAMPLE 78

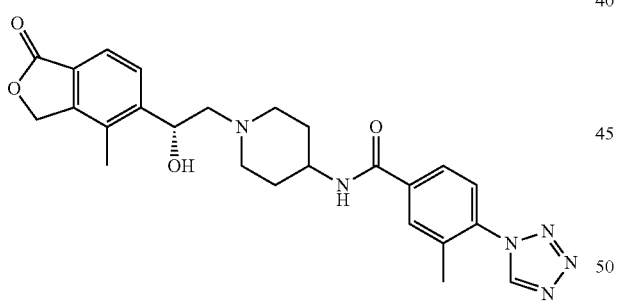

(R)-N-(1-(2-Hydroxy-2-(4-methyl-1-oxo-1,3-dihydroisobenzofuran-5-yl)ethyl)piperidin-4-yl)-3-methyl-4-(1H-tetrazol-1-yl)benzamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 3-methyl-4-(1H-tetrazol-1-yl)benzoic acid. LC-MS (IE, m/z): 477.

EXAMPLE 79

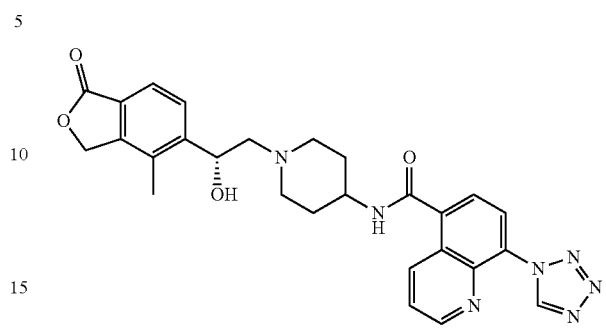

(R)-N-(1-(2-Hydroxy-2-(4-methyl-1-oxo-1,3-dihydroisobenzofuran-5-yl)ethyl)piperidin-4-yl)-8-(1H-tetrazol-1-yl)quinoline-5-carboxamide The title compound was prepared in a similar fashion to that described for the synthesis of EXAMPLE 8 starting from (R)-5-(2-(4-aminopiperidin-1-yl)-1-hydroxyethyl)-4-methylisobenzofuran-1(3H)-one hydrochloride and 8-(1H-tetrazol-1-yl)quinoline-5-carboxylic acid. LC-MS (IE, m/z): 514.

EXAMPLE 80

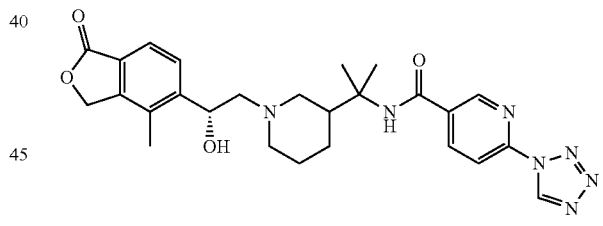

N-(2-(1-((R)-2-Hydroxy-2-(4-methyl-1-oxo-1,3-dihydroisobenzofuran-5-yl)ethyl)piperidin-3-yl)propan-2-yl)-6-(1H-tetrazol-1-yl)nicotinamide N-(2-(1-((R)-2-Hydroxy-2-(4-methyl-1-oxo-1,3-dihydroisobenzofuran-5-yl)ethyl)piperidin-3-yl)propan-2-yl)-6-(1H-tetrazol-1-yl)nicotinamide was prepared in a similar fashion to that described for the synthesis of EXAMPLE 8 starting from 5-((1R)-2-(3-(aminomethyl)-3-methylpiperidin-1-yl)-1-hydroxyethyl)-4-methylisobenzofuran-1(3H)-one hydrochloride and 6-(1H-tetrazol-1-yl)nicotinic acid. LC-MS (IE, m/z): 506.

EXAMPLE 81 A AND B

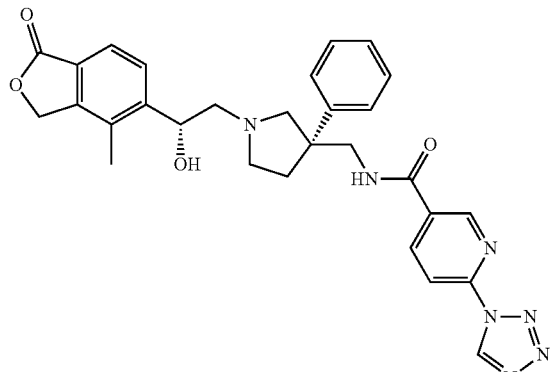

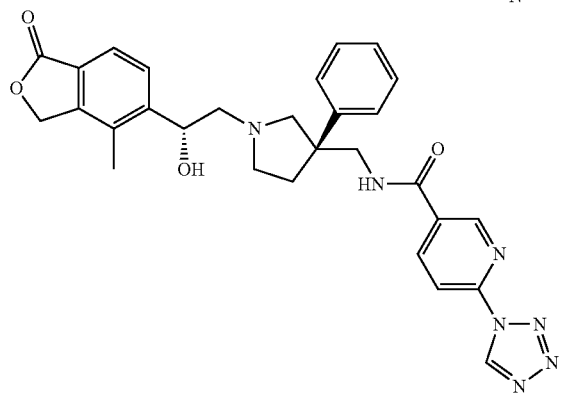

N-((1-((R)-2-Hydroxy-2-(4-methyl-1-oxo-1,3-dihydroisobenzofuran-5-yl)ethyl)-3-phenylpyrrolidin-3-yl)methyl)-6-(1H-tetrazol-1-yl)nicotinamide The title compound was prepared in a similar fashion to that described for the synthesis of EXAMPLE 8 starting from 5-((1R)-2-(3-(aminomethyl)-3-phenylpyrrolidin-1-yl)-1-hydroxyethyl)-4-methylisobenzofuran-1(3H)-one hydrochloride and 6-(1H-tetrazol-1-yl)nicotinic acid. Mass directed preparative HPLC, using acetonitrile/water/ammonium acetate as mobile phase, provided for isolation of the individual diastereomers. Isomer A: LC-MS (IE, m/z): 540. Isomer B: LC-MS (IE, m/z): 540.

EXAMPLE 82

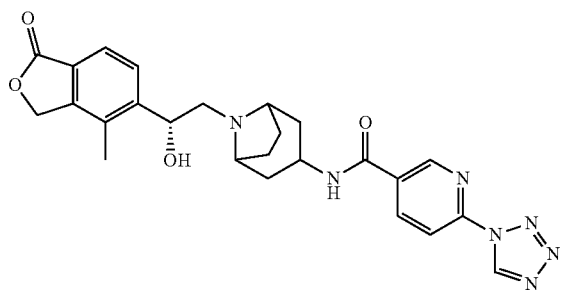 [SMILES: Cc1c([C@@H](O)CN2C3CCC2CC(NC(=O)c2ccc(-n4cnnn4)nc2)C3)ccc2c1COC2=O]

N-(8-((R)-2-Hydroxy-2-(4-methyl-1-oxo-1,3-dihydroisobenzofuran-5-yl)ethyl)-8-azabicyclo[3.2.1]octan-3-yl)-6-(1H-tetrazol-1-yl)nicotinamide The title compound was prepared in a similar fashion to that described for the synthesis of EXAMPLE 8 starting from 5-((1R)-2-(3-amino-8-azabicyclo[3.2.1]octan-8-yl)-1-hydroxyethyl)-4-methylisobenzofuran-1(3H)-one hydrochloride and 6-(1H-tetrazol-1-yl)nicotinic acid. LC-MS (IE, m/z): 489.

EXAMPLE 83

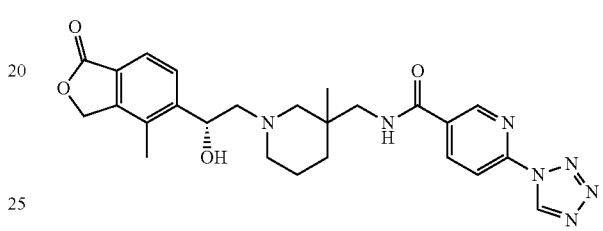

N-((1-((R)-2-Hydroxy-2-(4-methyl-1-oxo-1,3-dihydroisobenzofuran-5-yl)ethyl)-3-methylpiperidin-3-yl)methyl)-6-(1H-tetrazol-1-yl)nicotinamide The title compound was prepared in a similar fashion to that described for the synthesis of EXAMPLE 8 starting from 5-((1R)-2-(3-(aminomethyl)-3-methylpiperidin-1-yl)-1-hydroxyethyl)-4-methylisobenzofuran-1(3H)-one hydrochloride and 6-(1H-tetrazol-1-yl)nicotinic acid. LC-MS (IE, m/z): 492.

EXAMPLE 84

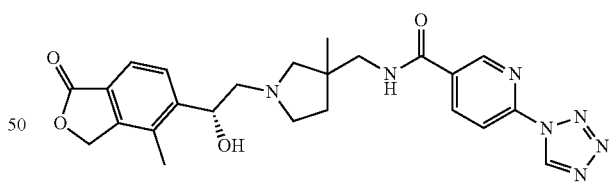

N-((1-((R)-2-Hydroxy-2-(4-methyl-1-oxo-1,3-dihydroisobenzofuran-5-yl)ethyl)-3-methylpyrrolidin-3-yl)methyl)-6-(1H-tetrazol-1-yl)nicotinamide The title compound was prepared in a similar fashion to that described for the synthesis of EXAMPLE 8 starting from 5-((1R)-2-(3-(aminomethyl)-3-methylpyrrolidin-1-yl)-1-hydroxyethyl)-4-methylisobenzofuran-1(3H)-one hydrochloride and 6-(1H-tetrazol-1-yl)nicotinic acid. LC-MS (IE, m/z): 478.

EXAMPLE 85

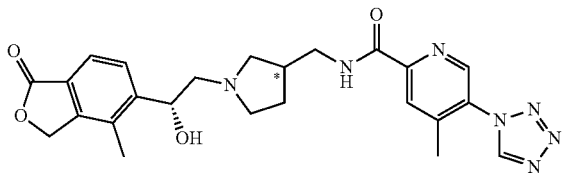

(* = chiral center)

N-((1-((R)-2-Hydroxy-2-(4-methyl-1-oxo-1,3-dihydroisobenzofuran-5-yl)ethyl)pyrrolidin-3-yl)methyl)-4-methyl-5-(1H-tetrazol-1-yl)picolinamide The title compound was prepared in a similar fashion to that described for the synthesis of EXAMPLE 8 starting from 5-[(1R)-2-[2-(aminomethyl)pyrrolidin-1-yl]-1-hydroxyethyl}-4-methyl-2-benzofuran-1(3H)-one hydrochloride and 4-methyl-5-(1H-tetrazol-1-yl)picolinic acid. LC-MS (IE, m/z): 478.

EXAMPLE 86

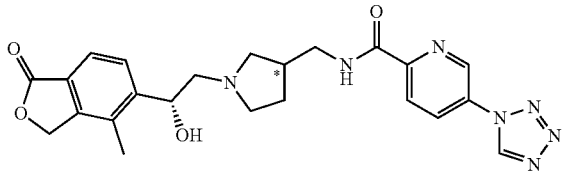

(* = chiral center)

N-((1-((R)-2-Hydroxy-2-(4-methyl-1-oxo-1,3-dihydroisobenzofuran-5-yl)ethyl)pyrrolidin-3-yl)methyl)-5-(1H-tetrazol-1-yl)picolinamide The title compound was prepared in a similar fashion to that described for the synthesis of EXAMPLE 8 starting from 5-[(1R)-2-[2-(aminomethyl)pyrrolidin-1-yl]-1-hydroxyethyl}-4-methyl-2-benzofuran-1(3H)-one hydrochloride and 5-(1H-tetrazol-1-yl)picolinic acid. LC-MS (IE, m/z): 464.

EXAMPLE 87

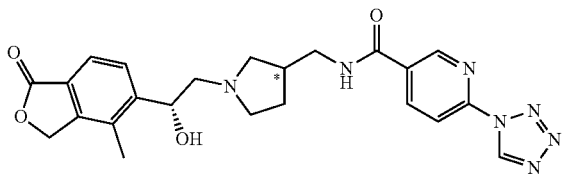 [SMILES: Cc1c([C@@H](O)CN2CCC(C)(CNC(=O)c3ccc(-n4cnnn4)nc3)C2)ccc2c1COC2=O]

(* = chiral center)

N-((1-((R)-2-Hydroxy-2-(4-methyl-1-oxo-1,3-dihydroisobenzofuran-5-yl)ethyl)pyrrolidin-3-yl)methyl)-6-(1H-tetrazol-1-yl)picolinamide The title compound was prepared in a similar fashion to that described for the synthesis of EXAMPLE 8 starting from 5-[(1R)-2-[2-(aminomethyl)pyrrolidin-1-yl]-1-hydroxyethyl}-4-methyl-2-benzofuran-1(3H)-one hydrochloride and 6-(1H-tetrazol-1-yl)picolinic acid. LC-MS (IE, m/z): 464.

EXAMPLE 88

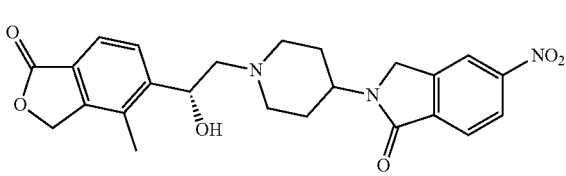 [SMILES: Cc1c([C@@H](O)CN2CCC(N3Cc4cc([N+](=O)[O-])ccc4C3=O)CC2)ccc2c1COC2=O]

(R)-2-(1-(2-Hydroxy-2-(4-methyl-1-oxo-1,3-dihydroisobenzofuran-5-yl)ethyl)piperidin-4-yl)-5-nitroisoindolin-1-one To a solution of (R)-5-(2-(4-aminopiperidin-1-yl)-1-hydroxyethyl)-4-methylisobenzofuran-1(3H)-one hydrochloride (25 mg, 0.069 mmol) and methyl 2-(bromomethyl)-4-nitrobenzoate (19 mg, 0.069) in methanol (1.5 mL) was added triethylamine (34 µL, 0.24 mmol). The solution was heated to reflux for two hours, cooled to ambient temperature, and then concentrated in vacuo. The crude residue was purified via reverse-phase HPLC (TMC Pro-Pac C18; 10-100% 0.1% trifluoroacetic acid in acetonitrile/0.1% trifluoroacetic acid in water gradient) to afford the title compound. $^1$H NMR (500 MHz, CDCl$_3$): 8.2 (m, 1H), 8.15 (s, 1H), 8 (m, 1H), 7.8 (m, 2H), 5.21 (s, 2H), 5.1 (m, 1H), 4.5 (s, 2H), 4.4 (m, 1H), 3.4 (m, 1H), 3.0 (m, 1H), 2.6 (m, 3H), 2.4 (m, 2H), 2.3 (m, 4), 1.9-2.0 (broad m, 5H). LC-MS (IE, m/z): 452.

EXAMPLE 89

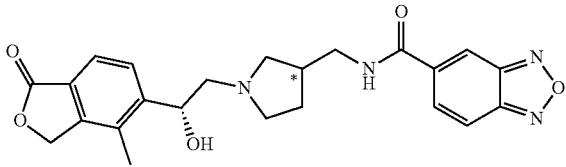

(* = chiral center)

N-((1-((R)-2-Hydroxy-2-(4-methyl-1-oxo-1,3-dihydroisobenzofuran-5-yl)ethyl)pyrrolidin-3-yl)methyl)benzo[c][1,2,5]oxadiazole-5-carboxamide The title compound was prepared in a similar fashion to that described for the synthesis of EXAMPLE 8 starting from 5-[(1R)-2-[2-(aminomethyl)pyrrolidin-1-yl]-1-hydroxyethyl}-4-methyl-2-benzofuran-1(3H)-one hydrochloride and benzo[c][1,2,5]oxadiazole-5-carboxylic acid. LC-MS (IE, m/z): 437.

EXAMPLE 90 A AND B

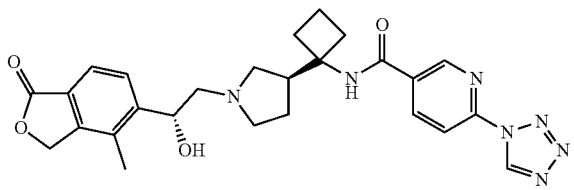

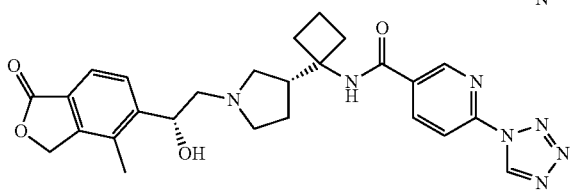

N-(1-(1-(((R)-2-Hydroxy-2-(4-methyl-1-oxo-1,3-dihydroisobenzofuran-5-yl)ethyl)pyrrolidin-3-yl)cyclobutyl)-6-(1H-tetrazol-1-yl)nicotinamide The title compound was prepared in a similar fashion to that described for the synthesis of EXAMPLE 8 starting from 5-((1R)-2-(3-(1-aminocyclobutyl)pyrrolidin-1-yl)-1-hydroxyethyl)-4-methylisobenzofuran-1(3H)-one hydrochloride and 6-(1H-tetrazol-1-yl)nicotinic acid. Mass directed preparative HPLC provided for isolation of the individual diastereomers.

Isomer A: LC-MS (IE, m/z): 504. Isomer B: LC-MS (IE, m/z): 504.

EXAMPLE 91

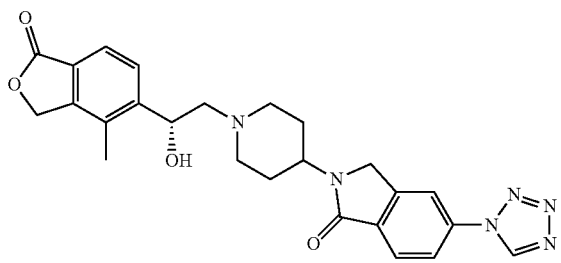 [SMILES: Cc1c([C@@H](O)CN2CCC(N3Cc4cc(-n5cnnn5)ccc4C3=O)CC2)ccc2c1COC2=O]

(R)-2-(1-(2-Hydroxy-2-(4-methyl-1-oxo-1,3-dihydroisobenzofuran-5-yl)ethyl)piperidin-4-yl)-5-(1H-tetrazol-1-yl)isoindolin-1-one Step A: tert-butyl 4-(5-nitro-1-oxo-1,3-dihydro-2H-isoindol-2-yl)piperidine-1-carboxylate tert-Butyl 4-(5-nitro-1-oxo-1,3-dihydro-2H-isoindol-2-yl)piperidine-1-carboxylate was prepared from methyl 4-bromo-2-(bromomethyl)benzoate and tert-butyl 4-aminopiperidine-1-carboxylate according to the procedure outlined for the synthesis of EXAMPLE 89. LC-MS (IE, m/z): 371.

Step B: tert-butyl 4-(5-amino-1-oxo-1,3-dihydro-2H-isoindol-2-yl)piperidine-1-carboxylate A solution of tert-butyl 4-(5-nitro-1-oxo-1,3-dihydro-2H-isoindol-2-yl)piperidine-1-carboxylate in dichloromethane was added to a slurry of palladium on carbon in dichloromethane. The reaction was placed under a balloon atmosphere of hydrogen and allowed to stir at ambient temperature for 15 hours. The reaction was then filtered over a pad of CELITE® and concentrated in vacuo. The crude material was purified via MPLC (10% MeOH/DCM isocratic) to obtain the title compound.

Step C: tert-butyl 4-[1-oxo-5-(1H-tetrazol-1-yl)-1,3-dihydro-2H-isoindol-2-yl]piperidine-1-carboxylate The title compound was prepared from tert-butyl 4-(5-amino-1-oxo-1,3-dihydro-2H-isoindol-2-yl)piperidine-1-carboxylate according to the procedure outlined for the synthesis of INTERMEDIATE 28.

Step D: 2-(piperidin-4-yl)-5-(1H-tetrazol-1-yl)-2,3-dihydro-1H-isoindol-1-one tert-Butyl 4-(5-amino-1-oxo-1,3-dihydro-2H-isoindol-2-yl)piperidine-1-carboxylate (50 mg, 0.14 mmol) was diluted in 1:1 mixture of trifluoroacetic acid and DCM (5 mL) and allowed to stir at ambient temperature for one hour. The reaction was then concentrated in vacuo to yield the TFA salt of the title compound which was used without further purification.

Step E: 2-{1-[(2R)-2-hydroxy-2-(4-methyl-1-oxo-1,3-dihydro-2-benzofuran-5-yl)ethyl]piperidin-4-yl}-5-(1H-tetrazol-1-yl)-2,3-dihydro-1H-isoindol-1-one The TFA salt of 2-(piperidin-4-yl)-5-(1H-tetrazol-1-yl)-2,3-dihydro-1H-isoindol-1-one (30 mg, 0.13 mmol) was diluted in ethanol (3 mL) and then was treated with triethylamine (20 µL, 0.151 mmol) for 15 minutes. After 15 minutes, 4-methyl-5-[(2R)-oxiran-2-yl]-2-benzofuran-1(3H)-one was added and the reaction mixture was heated to reflux for three hours. Once cooled, the reaction was concentrated in vacuo and purified via reverse-phase HPLC (TMC Pro-Pac C18; 10-100% 0.1% trifluoroacetic acid in acetonitrile/0.1% trifluoroacetic acid in water gradient) to afford the title compound. $^1$H NMR (500 MHz, DMSO-$d_6$): 10.2 (s, 1H), 8.25 (s, 1H), 8.1 (m, 1H), 7.8 (m, 2H), 6.4 (s, 1H), 5.4 (m, 3H), 4.6 (m, 3H), 4.4 (m, 1H), 3.9 (m, 1H) 3.7 (m, 1H) 2.6 (s, 3H). LC-MS (IE, m/z): 475.

The following Thallium Flux Assay and/or the Electrophysiology Assay were performed on each of the final product compounds in the Examples unless otherwise noted in an Example.

Thallium Flux Assay

Cell Culture Conditions—HEK293 cells stably expressing hROMK (hK$_{ir}$1.1) were grown at 37° C. in a 10% CO$_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./CO$_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 mL water. Store at 4° C.
  FluxOR™ Chloride-free Buffer (Component E)—5× Concentrate
  Potassium sulfate ($K_2SO_4$) Concentrate (Component F)—125 mM in water. Store at 4° C.
  Thallium sulfate ($Tl_2SO_4$) Concentrate (Component G)—50 mM in water. Store at 4° C.
  DMSO (dimethyl sulfoxide, Component H)—1 mL (100%)

Reagent Preparation: FluxOR Working Solutions
  1000× FluxOR™ Reagent: Reconstitute a vial of component A in 100 μl DMSO; Mix well; Store 10 μl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 mL of 1× FluxOR™ Assay Buffer; 1 mL of reconstituted component D; Store at 4° C.
  Loading Buffer (per microplate): 10 μl 1000× FluxOR™ Reagent; 100 μl component C; 10 mL Probenecid/Assay Buffer
  Compound Buffer (per microplate): 20 mL Probenecid/Assay Buffer; 0.3 mM ouabain (10 mM ouabain in water can be stored in amber bottle/aluminum foil at room temperature); Test compound
  1× FluxOR™ Chloride-Free Buffer: Prepare 1× working solution in water. Can be stored at room temperature
  Stimulant Buffer (prepared at 5× final concentration in 1× FluxOR™Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer± test compound followed by 30 min incubation at ambient temperature, where the Thallium/Potassium stimulant is added to the microplate.

Step Protocol
1. Seed HEK-hKir1.1 cells (50 μl at 20,000 cells/well) in 384-well PDL coated Microplates
2. Allow cells to adhere overnight in humidified 37° C./10% $CO_2$ incubator
3. Completely remove cell growth media from microplate and replace with 25 μl loading buffer
4. Incubate Microplate at room temperature, protected form light, for 90 min
5. Remove loading buffer and replace with 25 μl 1× Assay Buffer±test compound.
6. Incubate microplate at room temperature, protected from light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—The fluorescence intensity of wells containing 3 μM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay.

Alternatively, the control could be another compound (outside the scope of Formula I) that has an $IC_{50}$ potency in this assay of less than 1 μM.

Electrophysiology Assay

Block of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066) for approximately 6 min at 37° C. and suspended in 10 mL of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/mL amphotericin B for 4 min. Amphotericin B (Sigma A-4888) was prepared as a 40 mg/mL solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Data collected for compounds in the Examples of the present invention using the Thallium Flux Assay and the Electrophysiology Assay are shown in the Table below. All of the tested final product compounds in the Examples (stereoisomeric mixtures and individual stereoisomers) had $IC_{50}$ potencies less than 1 µM in one or both of the Thallium Flux Assay and the Electrophysiology Assay.

TABLE

| Example No. | Thallium Flux $IC_{50}$ (µM) | |
|---|---|---|
| 1 | 0.01 | Electrophysiology $IC_{50}$(µM): 0.04 |
| 2 | 0.60 | |
| 3 | 0.50 | |
| 4 | 0.32 | |
| 5 | 0.02 | |
| 6 | 0.04 | |
| 7 | 0.01 | |
| 8 | 0.46 | |
| 9 | 0.03 | |
| 10 | 0.06 | |
| 11 | 0.03 | |
| 12 | 1.0 | Electrophysiology $IC_{50}$(µM): 0.12 |
| 13 | 0.35 | |
| 14 | 0.07 | |
| 15 | 0.45 | |
| 16 | 0.05 | |
| 17 | 0.03 | |
| 18 | 0.95 | |
| 19 | 0.05 | |
| 20 | 0.07 | |
| 21 | 0.15 | |
| 22 | 0.02 | |
| 23 | 0.72 | |
| 24 | 0.15 | |
| 25 | 0.03 | |
| 26 | 0.07 | |
| 27 | 0.03 | |
| 28 | 0.03 | |
| 29 | 1.23 | Electrophysiology $IC_{50}$(µM): 0.24 |
| 30 | 0.12 | |
| 31 | 0.10 | |
| 32 | 0.48 | |
| 33 | 0.06 | |
| 34 | 0.23 | |
| 35 | 0.06 | |
| 36 | 0.45 | |
| 37 | 0.10 | |
| 38 | 1.0 | |
| 39 | 0.31 | |
| 40 | 1.32 | Electrophysiology $IC_{50}$(µM): 0.63 |
| 41 | 0.07 | |
| 42 | 0.10 | |
| 43 B | 0.18 | |
| 44 A | 0.57 | |
| 44 B | 0.26 | |
| 45 | 0.45 | |
| 46 A | 0.52 | |
| 46 B | 0.65 | |
| 47 A | 0.16 | |
| 47 B | 0.18 | |
| 48 A | 0.08 | |
| 48 B | 0.10 | |
| 49 | 0.15 | |
| 50 A | 0.10 | |
| 50 B | 0.93 | |
| 51 | 0.39 | |
| 52 | 0.38 | |
| 53 | 0.19 | |
| 54 A | 0.76 | |
| 54 B | 0.34 | |
| 55 | 0.53 | |
| 56 | 0.71 | |
| 57 | 0.32 | |
| 58 A | 0.54 | |
| 58 B | 0.87 | |
| 59 | 0.09 | |
| 60 | 0.18 | |
| 61 | 0.23 | |
| 62 | 0.37 | |
| 63 | 0.86 | |
| 64 | 0.47 | |
| 65 | 0.11 | |
| 66 | 0.22 | |
| 67 | 0.36 | |
| 68 | 0.63 | |
| 69 A | 0.88 | |
| 69 B | 0.49 | |
| 70 | 0.76 | |
| 71 | 0.28 | |
| 72 | 0.08 | |
| 73 | 0.27 | |
| 74 | 0.63 | |
| 75 | 0.39 | |
| 76 | 0.43 | |
| 77 | 0.53 | |
| 78 | 0.56 | |
| 79 | 0.37 | |
| 80 | 0.97 | |
| 81 A | 0.62 | |
| 81 B | 0.16 | |
| 82 | 0.25 | |
| 83 | 0.72 | |
| 84 | 0.19 | |
| 85 | 0.37 | |
| 86 | 0.98 | |
| 87 | 0.84 | |
| 88 | 0.03 | |
| 89 | 0.26 | |
| 90 A | 0.74 | |
| 90 B | 0.28 | |
| 91 | 0.13 | |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneuously hypertensive rats (SHR):

Spontaneously hypertensive rats (SHR, male, 6 months, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. Example numbers 22, 28, 59 and 65 were evaluated at PO, QD doses at one or more doses within the range of 0.3 to 10 mg/kg and resulted in typical reductions in daily (24 h) mean systolic blood pressure ranging from 6 mmHg to 24 mmHg at the doses used by the last day of the studies.

The Spontaneously Hypertensive Rat Assay is well known and often used in the art as an experimental model simulating human hypertension (see, e.g., Lerman, L. O., et al., *J Lab Clin Med,* 2005; 146: 160-173).

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I:

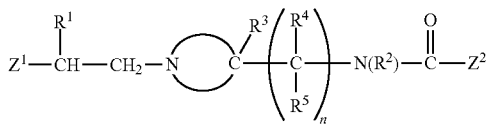

or a pharmaceutically acceptable salt thereof wherein:

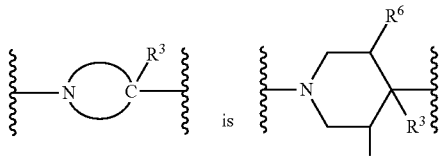

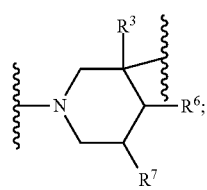

m is the integer zero or 1;
n is the integer zero or 1;
one of the dashed lines a, b or c represents a —CH$_2$— or —CH$_2$—CH$_2$— bridge, and the other dashed lines are absent;
$R^1$ is —H, —OC$_{1-3}$alkyl or —OH;
$R^2$ is —H or —C$_{1-3}$alkyl;
$R^3$ is —H, —F, —C$_{1-3}$alkyl or phenyl;
or, when n is zero, $R^2$ and $R^3$ are joined together to represent —(CH$_2$)$_{(q)}$— and form a 4-6 member ring with the nitrogen and carbon to which each is attached;
q is the integer 2, 3 or 4;
$R^4$ and $R^5$ are each independently —H or —C$_{1-3}$alkyl, or $R^4$ and $R^5$ are joined together with the carbon to which they are attached to form C$_{3-6}$cycloalkyl;
$R^6$ is —H, —C$_{1-3}$alkyl, —OH, —OC$_{1-3}$alkyl or —F, or is di-fluoro that replaces two hydrogens on the carbon to which it is attached;
$R^7$ is —H, —C$_{1-3}$alkyl, —OH, —OC$_{1-3}$alkyl or —F, or is di-fluoro that replaces two hydrogens on the carbon to which it is attached;
$Z^1$ is

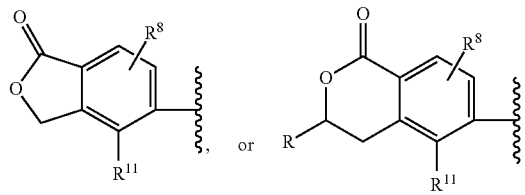

R is —H or —C$_{1-4}$alkyl;
$R^8$ is —H, —F, —Cl, —C$_{1-6}$alkyl, —C$_{3-6}$cycloalkyl or —OC$_{1-6}$alkyl;
$R^9$ is —H, —F, —Cl, —CN, —C$_{1-6}$alkyl, —C$_{3-6}$cycloalkyl or —OC$_{1-6}$alkyl; or when $R^{10}$ is —H, then $R^9$ can be 1H-tetrazol-1-yl;
$R^{10}$ is —H, —Cl, —F, —CN, —C$_{1-6}$alkyl, —C$_{3-6}$cycloalkyl or —OC$_{1-4}$alkyl;
$R^{11}$ is —H, —Cl, —F, —CN, —C$_{1-4}$alkyl, —C$_{3-6}$cycloalkyl or —OC$_{1-4}$alkyl;
$R^{11a}$ is —H, —Cl, —F, —CN, —C$_{1-4}$alkyl, —C$_{3-6}$cycloalkyl or —OC$_{1-4}$alkyl;
provided that $R^9$ and $R^{10}$ are not both —H; and
provided that one and only one of $R^9$, $R^{10}$ or $R^{11a}$ is —CN;
$Z^2$ is

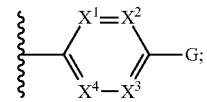

$X^1$, $X^2$, $X^3$ and $X^4$ are each independently C(R$^a$) or N, provided that one or two of $X^1$, $X^2$, $X^3$ and $X^4$ must be N and the others are C(R$^a$);
each $R^a$ is independently —H or —C$_{1-3}$alkyl;
G is —OC$_{1-3}$alkyl, —CN or a 5-membered heteroaryl;
$R^{8a}$ is —H, —F, —Cl, —C$_{1-6}$alkyl, —C$_{3-6}$cycloalkyl or —OC$_{1-6}$alkyl;
$R^{12}$ is —H, —C$_{1-3}$alkyl, —OC$_{1-3}$alkyl, —SO$_2$C$_{1-3}$alkyl or halo;
$R^{13}$ is —H, —C$_{1-3}$alkyl, —OC$_{1-3}$alkyl, halo, —NO$_2$, —CN or a 5-membered heteroaryl;
$R^{14}$ is —H, —C$_{1-3}$alkyl, —OC$_{1-3}$alkyl, halo, —NO$_2$, —CN or a 5-membered heteroaryl;
provided that only one of $R^{13}$ and $R^{14}$ is —CN, —NO$_2$ or the 5-membered heteroaryl and the other is —H, —C$_{1-3}$alkyl, —OC$_{1-3}$alkyl or halo;
$R^{15}$ is —H, —C$_{1-3}$alkyl, —OC$_{1-3}$alkyl, —SO$_2$C$_{1-3}$alkyl or halo;

$R^{15a}$ is —H, —$C_{1-3}$alkyl, —O$C_{1-3}$alkyl, —SO$_2C_{1-3}$alkyl or halo;

or $R^2$ and $R^{15}$ are joined together and represent —CH$_2$— to form the bicyclic fused ring system

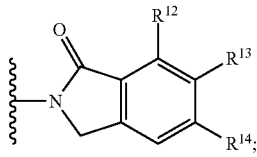

and $R^{16}$ is —H, —Cl, —F, —CN, —$C_{1-4}$alkyl, —$C_{3-6}$cycloalkyl or —O$C_{1-4}$alkyl.

2. The compound of claim 1 or a pharmaceutically acceptable salt thereof wherein $R^1$ is —H or —OH, $R^2$ is —H or —CH$_3$ and $R^3$ is —H, —$C_{1-3}$alkyl or phenyl.

3. The compound of claim 2 or a pharmaceutically acceptable salt thereof wherein $R^6$ is —H, —F or —OCH$_3$ and $R^7$ is —H, —F or —OCH$_3$.

4. The compound of claim 1 having structural Formula II or a pharmaceutically acceptable salt thereof:

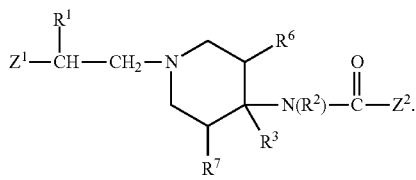

5. The compound of claim 2 having structural Formula IIa or a pharmaceutically acceptable salt thereof:

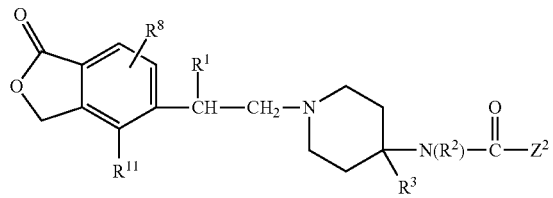

wherein $R^1$ is —H or —OH;

$R^2$ is —H or —CH$_3$, or $R^2$ and $R^{15}$ are joined together and represent —CH$_2$— to form the bicyclic fused ring system

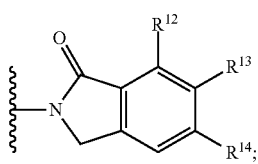

and $R^3$ is —H or —$C_{1-3}$alkyl.

6. The compound of claim 5 or a pharmaceutically acceptable salt thereof wherein: $Z^2$ is

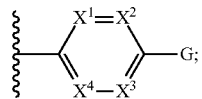

G is —CN or 1H-tetrazol-1-yl; when $R^2$ and $R^{15}$ are joined together and represent —CH$_2$— then $R^{14}$ is —NO$_2$; and when $R^2$ and $R^{15}$ are not joined together, then one of $R^{13}$ and $R^{14}$ is —CN or a 5-membered heteroaryl and the other is —H, —$C_{1-3}$alkyl, —O$C_{1-3}$alkyl or halo.

7. The compound of claim 1 having structural Formula III or a pharmaceutically acceptable salt thereof:

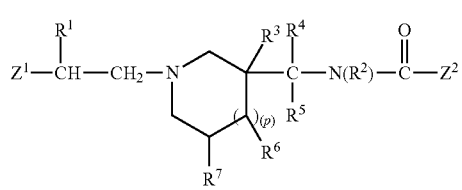

wherein p is an integer selected from 0 (zero) or 1 (one).

8. The compound of claim 7 having structural Formula IIIa or a pharmaceutically acceptable salt thereof:

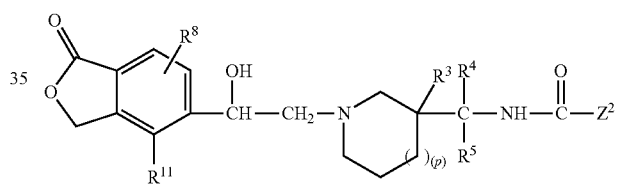

wherein $R^3$ is —H, —$C_{1-3}$alkyl or phenyl; $R^4$ and $R^5$ are each independently —H or —$C_{1-3}$alkyl, or $R^4$ and $R^5$ are joined together with the carbon to which they are attached to form $C_{3-6}$cycloalkyl.

9. The compound of claim 8 or a pharmaceutically acceptable salt thereof wherein $Z^2$ is;

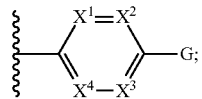

and G is 1H-tetrazol-1-yl.

10. A compound or a pharmaceutically acceptable salt thereof that is:

N-Methyl-N-(1-(2-(4-methyl-1-oxo-1,3-dihydroisobenzofuran-5-yl)ethyl)piperidin-4-yl)-1-oxo-1,3-dihydroisobenzofuran-5-carboxamide;

N-(1-(2-(4-Methyl-1-oxo-1,3-dihydroisobenzofuran-5-yl)ethyl)piperidin-4-yl)-6-(1H-tetrazol-1-yl)nicotinamide;

(S)-N-(1-(2-(3-methyl-1-oxoisochroman-6-yl)ethyl)piperidin-4-yl)-1-oxo-1,3-dihydroisobenzofuran-5-carboxamide;

4-Cyano-3-methoxy-N-(1-(2-(4-methyl-1-oxo-1,3-dihydroisobenzofuran-5-yl)ethyl)piperidin-4-yl)benzamide;
N-(1-(2-Hydroxy-2-(4-methyl-1-oxo-1,3-dihydroisobenzofuran-5-yl)ethyl)piperidin-4-yl)-1-oxo-1,3-dihydroisobenzofuran-5-carboxamide;
4-Cyano-N-(1-(2-hydroxy-2-(4-methyl-1-oxo-1,3-dihydroisobenzofuran-5-yl)ethyl)piperidin-4-yl)-3-methoxybenzamide;
3-Cyano-4-methoxy-N-(1-(2-(4-methyl-1-oxo-1,3-dihydroisobenzofuran-5-yl)ethyl)piperidin-4-yl)benzamide;
3-Cyano-N-(1-(2-hydroxy-2-(4-methyl-1-oxo-1,3-dihydroisobenzofuran-5-yl)ethyl)piperidin-4-yl)-4-methoxybenzamide;
4-Cyano-3-fluoro-N-(1-(2-(4-methyl-1-oxo-1,3-dihydroisobenzofuran-5-yl)ethyl)piperidin-4-yl)benzamide;
N-(1-(2-(3-Cyano-4-fluoro-2-methylphenyl)-2-hydroxyethyl)piperidin-4-yl)-1-oxo-1,3-dihydroisobenzofuran-5-carboxamide;
4-Cyano-N-(1-(2-(3-cyano-4-fluoro-2-methylphenyl)-2-hydroxyethyl)piperidin-4-yl)-3-methoxybenzamide;
N-(1-(2-(4-Methyl-1-oxo-1,3-dihydroisobenzofuran-5-yl)ethyl)piperidin-4-yl)-2-(1H-tetrazol-1-yl)isonicotinamide;
4-Cyano-3-fluoro-N-(1-(2-hydroxy-2-(4-methyl-1-oxo-1,3-dihydroisobenzofuran-5-yl)ethyl)piperidin-4-yl)benzamide;
5-Cyano-4-fluoro-2-methoxy-N-(1-(2-(4-methyl-1-oxo-1,3-dihydroisobenzofuran-5-yl)ethyl)piperidin-4-yl)benzamide;
5-Cyano-2-fluoro-4-methyl-N-(1-(2-(4-methyl-1-oxo-1,3-dihydroisobenzofuran-5-yl)ethyl)piperidin-4-yl)benzamide;
5-Cyano-4-methyl-N-(1-(2-(4-methyl-1-oxo-1,3-dihydroisobenzofuran-5-yl)ethyl)piperidin-4-yl)picolinamide;
(R)-5-Cyano-4-fluoro-N-(1-(2-hydroxy-2-(4-methyl-1-oxo-1,3-dihydroisobenzofuran-5-yl)ethyl)piperidin-4-yl)-2-methoxybenzamide;
(S)-5-Cyano-4-fluoro-N-(1-(2-hydroxy-2-(4-methyl-1-oxo-1,3-dihydroisobenzofuran-5-yl)ethyl)piperidin-4-yl)-2-methoxybenzamide;
(R)-5-cyano-N-(1-(2-hydroxy-2-(4-methyl-1-oxo-1,3-dihydroisobenzofuran-5-yl)ethyl)piperidin-4-yl)-4-methylpicolinamide;
(S)-5-cyano-N-(1-(2-hydroxy-2-(4-methyl-1-oxo-1,3-dihydroisobenzofuran-5-yl)ethyl)piperidin-4-yl)-4-methylpicolinamide;
(R)-6-Cyano-N-(1-(2-hydroxy-2-(4-methyl-1-oxo-1,3-dihydroisobenzofuran-5-yl)ethyl)piperidin-4-yl)nicotinamide;
(R)-4-Cyano-N-(1-(2-hydroxy-2-(4-methyl-1-oxo-1,3-dihydroisobenzofuran-5-yl)ethyl)piperidin-4-yl)-3-methylbenzamide;
(R)-4-Cyano-2-ethoxy-N-(1-(2-hydroxy-2-(4-methyl-1-oxo-1,3-dihydroisobenzofuran-5-yl)ethyl)piperidin-4-yl)benzamide;
(R)-4-Cyano-N-(1-(2-hydroxy-2-(4-methyl-1-oxo-1,3-dihydroisobenzofuran-5-yl)ethyl)piperidin-4-yl)benzamide;
(R)-5-Cyano-N-(1-(2-hydroxy-2-(4-methyl-1-oxo-1,3-dihydroisobenzofuran-5-yl)ethyl)piperidin-4-yl)picolinamide;
4-Cyano-N-(1-(2-(4-methyl-1-oxo-1,3-dihydroisobenzofuran-5-yl)ethyl)piperidin-4-yl)-2-(methylsulfonyl)benzamide;
N-(1-(2-(4-Methyl-1-oxo-1,3-dihydroisobenzofuran-5-yl)ethyl)piperidin-4-yl)-3-(1H-tetrazol-1-yl)benzamide;
N-(1-(2-(4-Methyl-1-oxo-1,3-dihydroisobenzofuran-5-yl)ethyl)piperidin-4-yl)-4-(1H-pyrazol-1-yl)benzamide;
4-Cyano-N-(1-(2-(4-methyl-1-oxo-1,3-dihydroisobenzofuran-5-yl)ethyl)piperidin-4-yl)thiophene-2-carboxamide;
5-Cyano-N-(3-((R)-2-hydroxy-2-(4-methyl-1-oxo-1,3-dihydroisobenzofuran-5-yl)ethyl)-3-azabicyclo[3.1.0]hexan-6-yl)picolinamide;
(R)-N-(1-(2-Hydroxy-2-(4-methyl-1-oxo-1,3-dihydroisobenzofuran-5-yl)ethyl)piperidin-4-yl)-4-(1H-tetrazol-1-yl)benzamide;
(R)-N-(1-(2-Hydroxy-2-(4-methyl-1-oxo-1,3-dihydroisobenzofuran-5-yl)ethyl)piperidin-4-yl)-4-(isoxazol-3-yl)benzamide;
(R)-N-(1-(2-Hydroxy-2-(4-methyl-1-oxo-1,3-dihydroisobenzofuran-5-yl)ethyl)piperidin-4-yl)-3-(1H-tetrazol-1-yl)benzamide;
(R)-N-(1-(2-Hydroxy-2-(4-methyl-1-oxo-1,3-dihydroisobenzofuran-5-yl)ethyl)piperidin-4-yl)-4-(1H-pyrazol-1-yl)benzamide;
5-Cyano-N-((trans)-3-fluoro-1-((R)-2-hydroxy-2-(4-methyl-1-oxo-1,3-dihydroisobenzofuran-5-yl)ethyl)piperidin-4-yl)picolinamide;
(R)-N-(1-(2-Hydroxy-2-(4-methyl-1-oxo-1,3-dihydroisobenzofuran-5-yl)ethyl)piperidin-4-yl)-4-(1H-pyrazol-3-yl)benzamide;
(R)-5-Cyano-N-(1-(2-hydroxy-2-(4-methyl-1-oxo-1,3-dihydroisobenzofuran-5-yl)ethyl)-4-methylpiperidin-4-yl)picolinamide;
(R)-5-Cyano-N-(1-(2-hydroxy-2-(4-methyl-1-oxo-1,3-dihydroisobenzofuran-5-yl)ethyl)piperidin-4-yl)-6-methylpicolinamide;
(R)-4-Cyano-N-(1-(2-hydroxy-2-(4-methyl-1-oxo-1,3-dihydroisobenzofuran-5-yl)ethyl)piperidin-4-yl)isoquinoline-1-carboxamide;
5-Cyano-N-((cis)-3-fluoro-1-((R)-2-hydroxy-2-(4-methyl-1-oxo-1,3-dihydroisobenzofuran-5-yl)ethyl)piperidin-4-yl)picolinamide;
5-Cyano-N-((cis)-3-fluoro-1-((R)-2-hydroxy-2-(4-methyl-1-oxo-1,3-dihydroisobenzofuran-5-yl)ethyl)piperidin-4-yl)-6-methylpicolinamide;
(R)-4-Cyano-2-fluoro-N-(1-(2-hydroxy-2-(4-methyl-1-oxo-1,3-dihydroisobenzofuran-5-yl)ethyl)piperidin-4-yl)benzamide;
6-Cyano-N-((cis)-3-fluoro-1-((R)-2-hydroxy-2-(4-methyl-1-oxo-1,3-dihydroisobenzofuran-5-yl)ethyl)piperidin-4-yl)nicotinamide;
4-Cyano-N-((cis)-3-fluoro-1-((R)-2-hydroxy-2-(4-methyl-1-oxo-1,3-dihydroisobenzofuran-5-yl)ethyl)piperidin-4-yl)-3-methylbenzamide;
5-Cyano-N-((cis)-3-fluoro-1-((R)-2-hydroxy-2-(4-methyl-1-oxo-1,3-dihydroisobenzofuran-5-yl)ethyl)piperidin-4-yl)-4-methylpicolinamide;
(R)-N-(1-(2-Hydroxy-2-(4-methyl-1-oxo-1,3-dihydroisobenzofuran-5-yl)ethyl)piperidin-4-yl)-6-(1H-tetrazol-1-yl)nicotinamide;
N-((cis)-3-Fluoro-1-((R)-2-hydroxy-2-(4-methyl-1-oxo-1,3-dihydroisobenzofuran-5-yl)ethyl)piperidin-4-yl)-6-(1H-tetrazol-1-yl)nicotinamide;

(R)-N-(1-(2-Hydroxy-2-(4-methyl-1-oxo-1,3-dihydroisobenzofuran-5-yl)ethyl)-4-methylpiperidin-4-yl)-6-(1H-tetrazol-1-yl)nicotinamide;
(R)-5-(2-(1-(6-(1H-Tetrazol-1-yl)picolinoyl)-1,7-diazaspiro[3.5]nonan-7-yl)-1-hydroxyethyl)-4-methylisobenzofuran-1(3H)-one;
(R)-N-(1-(2-Hydroxy-2-(4-methyl-1-oxo-1,3-dihydroisobenzofuran-5-yl)ethyl)piperidin-4-yl)-5-(1H-tetrazol-1-yl)picolinamide;
N-((cis)-1-((R)-2-Hydroxy-2-(4-methyl-1-oxo-1,3-dihydroisobenzofuran-5-yl)ethyl)-3-methoxypiperidin-4-yl)-6-(1H-tetrazol-1-yl)nicotinamide;
(R)-5-(2-(1-(5-(1H-Tetrazol-1-yl)picolinoyl)-1,7-diazaspiro[3.5]nonan-7-yl)-1-hydroxyethyl)-4-methylisobenzofuran-1(3H)-one;
N-(3-((R)-2-Hydroxy-2-(4-methyl-1-oxo-1,3-dihydroisobenzofuran-5-yl)ethyl)-3-azabicyclo[3.1.0]hexan-6-yl)-5-(1H-tetrazol-1-yl)picolinamide;
(R)-4-Cyano-N-(1-(2-hydroxy-2-(4-methyl-1-oxo-1,3-dihydroisobenzofuran-5-yl)ethyl)piperidin-4-yl)-3-methoxybenzamide;
N-((cis)-3-fluoro-1-((R)-2-hydroxy-2-(4-methyl-1-oxo-1,3-dihydroisobenzofuran-5-yl)ethyl)piperidin-4-yl)-5-(1H-tetrazol-1-yl)picolinamide;
(R)-N-(1-(2-Hydroxy-2-(4-methyl-1-oxo-1,3-dihydroisobenzofuran-5-yl)ethyl)piperidin-4-yl)-4-methyl-5-(1H-tetrazol-1-yl)picolinamide;
(R)-N-(1-(2-Hydroxy-2-(4-methyl-1-oxo-1,3-dihydroisobenzofuran-5-yl)ethyl)-4-methylpiperidin-4-yl)-5-(1H-tetrazol-1-yl)picolinamide;
N-((S)-1-((R)-2-Hydroxy-2-(4-methyl-1-oxo-1,3-dihydroisobenzofuran-5-yl)ethyl)pyrrolidin -3-yl)-5-(1H-tetrazol-1-yl)picolinamide;
N-((R)-1-((R)-2-Hydroxy-2-(4-methyl-1-oxo-1,3-dihydroisobenzofuran-5-yl)ethyl)pyrrolidin -3-yl)-5-(1H-tetrazol-1-yl)picolinamide;
(R)-N-(1-(2-Hydroxy-2-(4-methyl-1-oxo-1,3-dihydroisobenzofuran-5-yl)ethyl)-4-methylpiperidin-4-yl)-4-methyl-5-(1H-tetrazol-1-yl)picolinamide;
(R)-N-(1-(2-Hydroxy-2-(4-methyl-1-oxo-1,3-dihydroisobenzofuran-5-yl)ethyl)piperidin-4-yl)-5-(1H-tetrazol-1-yl)pyrazine-2-carboxamide;
(R)-N-(1-(2-Hydroxy-2-(4-methyl-1-oxo-1,3-dihydroisobenzofuran-5-yl)ethyl)piperidin-4-yl)-6-(1H-tetrazol-1-yl)pyridazine-3-carboxamide;
(R)-N-(1-(2-Hydroxy-2-(4-methyl-1-oxo-1,3-dihydroisobenzofuran-5-yl)ethyl)piperidin-4-yl)benzo[c][1,2,5]oxadiazole-5-carboxamide;
N-((1-((R)-2-Hydroxy-2-(4-methyl-1-oxo-1,3-dihydroisobenzofuran-5-yl)ethyl)-3-methylpiperidin-3-yl)methyl)-5-(1H-tetrazol-1-yl)picolinamide;
N-((1-((R)-2-Hydroxy-2-(4-methyl-1-oxo-1,3-dihydroisobenzofuran-5-yl)ethyl)-3-phenylpyrrolidin-3-yl)methyl)-5-(1H-tetrazol-1-yl)picolinamide;
N-((1-((R)-2-Hydroxy-2-(4-methyl-1-oxo-1,3-dihydroisobenzofuran-5-yl)ethyl)-3-methylpyrrolidin-3-yl)methyl)-5-(1H-tetrazol-1-yl)picolinamide;
N-(1-(1-((R)-2-Hydroxy-2-(4-methyl-1-oxo-1,3-dihydroisobenzofuran-5-yl)ethyl)pyrrolidin-3-yl)cyclobutyl)-5-(1H-tetrazol-1-yl)picolinamide;
(R)-N-(1-(2-Hydroxy-2-(4-methyl-1-oxo-1,3-dihydroisobenzofuran-5-yl)ethyl)-4-methylpiperidin-4-yl)-6-(1H-tetrazol-1-yl)pyridazine-3-carboxamide;
(R)-N-(1-(2-Hydroxy-2-(4-methyl-1-oxo-1,3-dihydroisobenzofuran-5-yl)ethyl)-4-methylpiperidin-4-yl)-5-(1H-tetrazol-1-yl)pyrazine-2-carboxamide;
(R)-N-(1-(2-Hydroxy-2-(4-methyl-1-oxo-1,3-dihydroisobenzofuran-5-yl)ethyl)piperidin-4-yl)-6-(1H-pyrazol-1-yl)nicotinamide;
(R)-N-(1-(2-Hydroxy-2-(4-methyl-1-oxo-1,3-dihydroisobenzofuran-5-yl)ethyl)piperidin-4-yl)-4-(1H-1,2,4-triazol-1-yl)benzamide;
(R)-N-(1-(2-Hydroxy-2-(4-methyl-1-oxo-1,3-dihydroisobenzofuran-5-yl)ethyl)piperidin-4-yl)-4-(thiazol-2-yl)benzamide;
N-(8-((R)-2-Hydroxy-2-(4-methyl-1-oxo-1,3-dihydroisobenzofuran-5-yl)ethyl)-8-azabicyclo[3.2.1]octan-3-yl)-5-(1H-tetrazol-1-yl)picolinamide;
(R)-N-(1-(2-Hydroxy-2-(4-methyl-1-oxo-1,3-dihydroisobenzofuran-5-yl)ethyl)-4-methylpiperidin-4-yl)benzo[c][1,2,5]oxadiazole-5-carboxamide;
(R)-N-(1-(2-Hydroxy-2-(4-methyl-1-oxo-1,3-dihydroisobenzofuran-5-yl)ethyl)piperidin-4-yl)-3-methyl-4-(1H-tetrazol-1-yl)benzamide;
(R)-N-(1-(2-Hydroxy-2-(4-methyl-1-oxo-1,3-dihydroisobenzofuran-5-yl)ethyl)piperidin-4-yl)-8-(1H-tetrazol-1-yl)quinoline-5-carboxamide;
N-(2-(1-((R)-2-Hydroxy-2-(4-methyl-1-oxo-1,3-dihydroisobenzofuran-5-yl)ethyl)piperidin-3-yl)propan-2-yl)-6-(1H-tetrazol-1-yl)nicotinamide;
N-((1-((R)-2-Hydroxy-2-(4-methyl-1-oxo-1,3-dihydroisobenzofuran-5-yl)ethyl)-3-phenylpyrrolidin-3-yl)methyl)-6-(1H-tetrazol-1-yl)nicotinamide;
N-(8-((R)-2-Hydroxy-2-(4-methyl-1-oxo-1,3-dihydroisobenzofuran-5-yl)ethyl)-8-azabicyclo[3.2.1]octan-3-yl)-6-(1H-tetrazol-1-yl)nicotinamide;
N-((1-((R)-2-Hydroxy-2-(4-methyl-1-oxo-1,3-dihydroisobenzofuran-5-yl)ethyl)-3-methylpiperidin-3-yl)methyl)-6-(1H-tetrazol-1-yl)nicotinamide;
N-((1-((R)-2-Hydroxy-2-(4-methyl-1-oxo-1,3-dihydroisobenzofuran-5-yl)ethyl)-3-methylpyrrolidin-3-yl)methyl)-6-(1H-tetrazol-1-yl)nicotinamide;
N-((1-((R)-2-Hydroxy-2-(4-methyl-1-oxo-1,3-dihydroisobenzofuran-5-yl)ethyl)pyrrolidin-3-yl)methyl)-4-methyl-5-(1H-tetrazol-1-yl)picolinamide;
N-((1-((R)-2-Hydroxy-2-(4-methyl-1-oxo-1,3-dihydroisobenzofuran-5-yl)ethyl)pyrrolidin-3-yl)methyl)-5-(1H-tetrazol-1-yl)picolinamide;
N-((1-((R)-2-Hydroxy-2-(4-methyl-1-oxo-1,3-dihydroisobenzofuran-5-yl)ethyl)pyrrolidin-3-yl)methyl)-6-(1H-tetrazol-1-yl)picolinamide;
(R)-2-(1-(2-Hydroxy-2-(4-methyl-1-oxo-1,3-dihydroisobenzofuran-5-yl)ethyl)piperidin-4-yl)-5-nitroisoindolin-1-one;
N-((1-((R)-2-Hydroxy-2-(4-methyl-1-oxo-1,3-dihydroisobenzofuran-5-yl)ethyl)pyrrolidin-3-yl)methyl)benzo[c][1,2,5]oxadiazole-5-carboxamide;
N-(1-(1-((R)-2-Hydroxy-2-(4-methyl-1-oxo-1,3-dihydroisobenzofuran-5-yl)ethyl)pyrrolidin -3-yl)cyclobutyl)-6-(1H-tetrazol-1-yl)nicotinamide;
(R)-2-(1-(2-Hydroxy-2-(4-methyl-1-oxo-1,3-dihydroisobenzofuran-5-yl)ethyl)piperidin-4-yl)-5-(1H-tetrazol-1-yl)isoindolin-1-one;

or a stereisomer thereof.

11. The compound of claim 1 or a pharmaceutically acceptable salt thereof that is

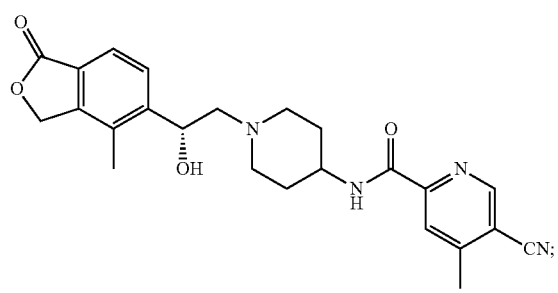

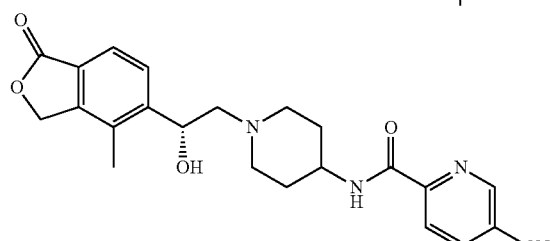

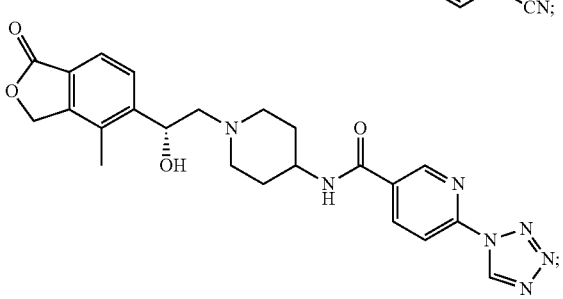

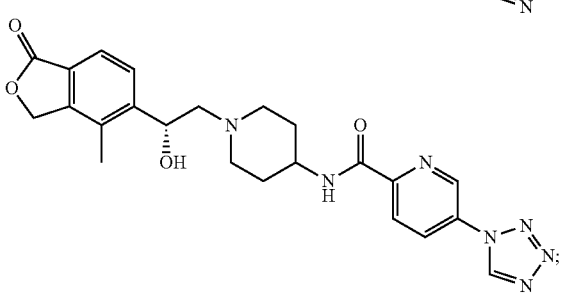

or

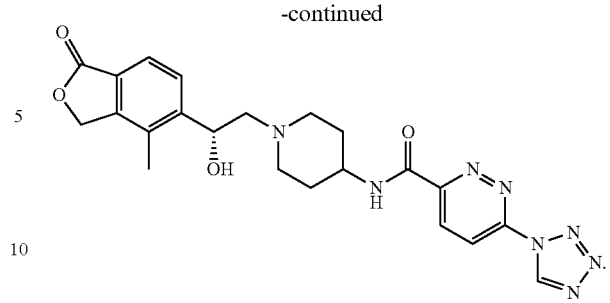

12. A pharmaceutical composition comprised of a compound of claim 1 or a pharmaceutically acceptable salt thereof and a pharmaceutically acceptable carrier.

13. A compound of claim 1 of Formula I wherein $Z^2$ is

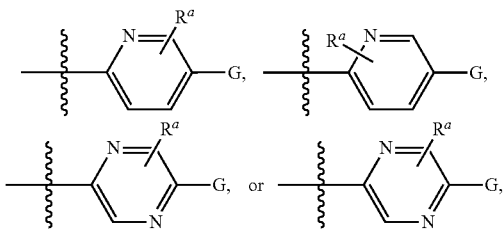

wherein $R^a$ is —H, —CH$_3$, or —C$_{1-3}$alkyl, or a pharmaceutically acceptable salt thereof.

14. A compound that is:
N-(1-(2-(4-Methyl-1-oxo-1,3-dihydroisobenzofuran-5-yl)ethyl)piperidin-4-yl)-1-oxo-1,3-dihydroisobenzofuran-5-carboxamide;

N-(1-(2-(4-Methyl-1-oxo-1,3-dihydroisobenzofuran-5-yl)ethyl)piperidin-4-yl)benzo[c][1,2,5]oxadiazole-5-carboxamide; or 3-Cyano-4-fluoro-N-(1-(2-(4-methyl-1-oxo-1,3-dihydroisobenzofuran-5-yl)ethyl)piperidin-4-yl)benzamide;

or a pharmaceutically acceptable salt thereof.

\* \* \* \* \*